(12) United States Patent
O'Shannessy

(10) Patent No.: US 9,139,656 B2
(45) Date of Patent: Sep. 22, 2015

(54) TEM-1 DIAGNOSTIC ANTIBODIES

(71) Applicant: Morphotek, Inc., Exton, PA (US)

(72) Inventor: Daniel John O'Shannessy, Schwenksville, PA (US)

(73) Assignee: Morphotek, Inc., Exton, PA (US)

( * ) Notice: Subject to any disclaimer, the term of this patent is extended or adjusted under 35 U.S.C. 154(b) by 118 days.

(21) Appl. No.: 13/804,730

(22) Filed: Mar. 14, 2013

(65) Prior Publication Data

US 2013/0260393 A1  Oct. 3, 2013

Related U.S. Application Data

(60) Provisional application No. 61/618,235, filed on Mar. 30, 2012.

(51) Int. Cl.
| | |
|---|---|
| *C07K 16/30* | (2006.01) |
| *G01N 33/53* | (2006.01) |
| *G01N 33/68* | (2006.01) |
| *C07K 16/28* | (2006.01) |

(52) U.S. Cl.
CPC ............ *C07K 16/30* (2013.01); *C07K 16/2851* (2013.01); *G01N 33/6893* (2013.01); *C07K 2317/92* (2013.01); *C07K 2319/30* (2013.01)

(58) Field of Classification Search
None
See application file for complete search history.

(56) References Cited

FOREIGN PATENT DOCUMENTS

| WO | WO 94/11023 A1 | 5/1994 |
|---|---|---|
| WO | WO 2006/017759 A2 | 2/2006 |
| WO | WO 2008/124570 A1 | 10/2008 |
| WO | WO 2010/118203 A2 | 10/2010 |

OTHER PUBLICATIONS

Cline, "Perspectives for Gene Therapy: Inserting New Genetic Information Into Mammalian Cells by Physical Techniques and Viral Vectors", Pharmac. Ther., 1985, 29, 69-92.
Gadi, "In vivo sensitization of ovarian tumors to chemotherapy by expression of *E. coli* purine nucleoside phosphorylase in a small fraction of cells" Gene Therapy, Oct. 2000, 7, 1738-1743.
Hanahan, D and Weinberg, R., "The Hallmarks of Cancer", Cell Press, Jan. 7, 2000, 100, 57-70.
Karlin, S. and Altschul, S., "Applications and statistics for multiple high-scoring segments in molecular sequences", Proc. Natl. Acad. Sci. USA, Jun. 1993, 90, 5873-5877.
Karlin, S. and Altschul, S., "Methods for assessing the statistical significance of molecular sequence features by using general scoring schemes", Proc. Natl. Acad., Mar. 1990, 2264-2268.
Okayama, H. and Berg, P., "A cDNA Cloning Vector That Permits Expression of cDNA Inserts in Mammalian Cells", Molecular and Cellular Biology, Feb. 1983, 3(2), 280-289.
Rettig, et al, "Identification of endosialin, a cell surface glycoprotein of vascular endothelial cells in human cancer", Proc. Nan. Acad. Sci. USA, Nov. 1992, 89, 10832-10836.
St. Croix, et al, "Genes Expressed in Human Tumor Endothelium", Science, Aug. 18, 2000, 289, 1197-1202.
Yancopoulos, et al, "Vascular-specific growth factors and blood vessel formation", Nature, Sep. 14, 2000, 407, 242-248.

*Primary Examiner* — Sean Aeder
*Assistant Examiner* — Julie Wu
(74) *Attorney, Agent, or Firm* — Baker & Hostetler LLP

(57) ABSTRACT

Described herein are antibodies, and antigen-binding fragments thereof, that are specific for tumor endothelial marker 1 (TEM-1), related polynucleotides, expression vectors, and cells that express the described antibodies. Also provided are methods of using the described antibodies, and antigen-binding fragments thereof, and related kits. Provided herein are also methods for diagnosing TEM-1-expressing cancers (such as melanoma, sarcoma, bladder cancer, gastric cancer, hepatocellular cancer, or colon cancer) using the described antibodies, and antigen-binding fragments thereof. The methods involve determining the amount of TEM-1 in a biological sample derived from a subject and comparing this level with the level of TEM-1 in a known standard or reference sample.

12 Claims, 6 Drawing Sheets

SEQUENCE LISTING

```
<160> NUMBER OF SEQ ID NOS: 161

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Ser Leu Leu Asp Ser Asp Gly Asn Thr Tyr
1               5                   10

<210> SEQ ID NO 2
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Val Ser
1

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 3

Met Gln Ala Thr His Ala Pro Phe Thr
1               5

<210> SEQ ID NO 4
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ser Pro Val Gln Ser Leu Phe Leu Leu Leu Trp Ile Leu Gly
1               5                   10                  15

Thr Lys Gly Asp Val Val Leu Thr Gln Thr Pro Ser Ile Leu Ser Ala
                20                  25                  30

Thr Ile Gly Gln Ser Val Ser Ile Ser Cys Arg Ser Ser Gln Ser Leu
            35                  40                  45

Leu Asp Ser Asp Gly Asn Thr Tyr Leu Tyr Trp Phe Leu Gln Arg Pro
50                  55                  60

Gly Gln Ser Pro Gln Arg Leu Ile Tyr Leu Val Ser Asn Leu Gly Ser
65                  70                  75                  80

Gly Val Pro Asn Arg Phe Ser Gly Ser Gly Ser Gly Thr Asp Phe Thr
                85                  90                  95

Leu Lys Ile Ser Gly Val Glu Ala Gly Asp Leu Gly Val Tyr Tyr Cys
            100                 105                 110

Met Gln Ala Thr His Ala Pro Phe Thr Phe Gly Ser Gly Thr Lys Leu
        115                 120                 125

Glu Ile Lys
        130

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Phe Asp Phe Lys Thr Tyr Ala
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Ser Thr Lys Gly His Asn Tyr Ala Thr
1               5                   10

<210> SEQ ID NO 7
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 7

Thr Val Ala Gly Tyr Asn Phe Asp Tyr
1               5

<210> SEQ ID NO 8
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Val Leu Leu Glu Leu Val Ser Val Ile Ala Leu Phe Gln Gly Val
1               5                   10                  15

His Cys Glu Val Gln Leu Val Glu Ser Gly Gly Gly Leu Val Gln Pro
            20                  25                  30

Lys Gly Ser Leu Lys Leu Ser Cys Ala Ala Ser Gly Phe Asp Phe Lys
        35                  40                  45

Thr Tyr Ala Met Ser Trp Val Arg Gln Ala Pro Gly Lys Gly Leu Asp
    50                  55                  60

Trp Ile Val Thr Ile Ser Thr Lys Gly His Asn Tyr Ala Thr Leu Tyr
65                  70                  75                  80

Ala Asp Ser Val Lys Glu Arg Phe Thr Ile Ser Arg Asp Asp Ser Gln
                85                  90                  95

Ser Met Val Tyr Leu Gln Met Asn Asn Leu Lys Thr Glu Asp Thr Ala
            100                 105                 110

Leu Tyr Tyr Cys Thr Val Ala Gly Tyr Asn Phe Asp Tyr Trp Gly Gln
        115                 120                 125

Gly Val Met Val Thr Val Ser Ser
    130                 135

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Ser Val Gly Ile Asn
1               5

<210> SEQ ID NO 10
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Ala Ser
1

<210> SEQ ID NO 11
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 11

Leu Gln Tyr Gly Ser Leu Pro Phe Thr
1               5

<210> SEQ ID NO 12
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Glu Ser His Thr Arg Val Phe Ile Phe Leu Leu Leu Trp Leu Ser
1               5                   10                  15

Gly Gly Asp Gly Glu Thr Val Met Thr Gln Ser Pro Thr Ser Met Pro
            20                  25                  30

Thr Ser Ile Gly Glu Arg Val Thr Leu Asn Cys Lys Ala Ser Gln Ser
        35                  40                  45

Val Gly Ile Asn Val Asp Trp Tyr Gln Gln Thr Pro Gly Gln Ser Pro
    50                  55                  60

Lys Leu Leu Ile Tyr Thr Ala Ser Asn Arg His Thr Gly Val Pro Asp
65                  70                  75                  80

Arg Phe Ala Gly Ser Gly Ser Gly Arg Asp Phe Thr Leu Thr Ile Ser
                85                  90                  95

Asn Val Glu Ala Glu Asp Leu Val Val Tyr Tyr Cys Leu Gln Tyr Gly
            100                 105                 110

Ser Leu Pro Phe Thr Phe Gly Ala Gly Thr Lys Leu Glu Leu Lys
        115                 120                 125

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Phe Thr Phe Ser Asn Phe Asp
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Thr Tyr Asp Gly Ser Arg Thr
1               5

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
```

```
                                    peptide

<400> SEQUENCE: 15

Ala Arg His Gly Ser Ser Tyr Tyr Trp Phe Phe Asp Phe
1               5                   10

<210> SEQ ID NO 16
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Asp Ile Arg Leu Ser Leu Ala Phe Leu Val Leu Phe Ile Lys Asp
1               5                   10                  15

Val Gln Cys Glu Val Gln Leu Val Glu Ser Gly Gly Leu Val Gln
            20                  25                  30

Pro Gly Arg Ser Met Ile Leu Ser Cys Ala Ala Ser Gly Phe Thr Phe
        35                  40                  45

Ser Asn Phe Asp Met Ala Trp Val Arg Gln Ala Pro Lys Met Gly Leu
    50                  55                  60

Glu Trp Val Ala Thr Ile Thr Tyr Asp Gly Ser Arg Thr Asn Tyr Arg
65                  70                  75                  80

Asp Ser Val Lys Gly Arg Phe Thr Ile Ser Arg Asp Ser Ala Lys Asn
                85                  90                  95

Thr Leu Tyr Leu Gln Met Asp Ser Leu Thr Ser Glu Asp Thr Ala Thr
            100                 105                 110

Tyr Tyr Cys Ala Arg His Gly Ser Ser Tyr Tyr Trp Phe Phe Asp Phe
        115                 120                 125

Trp Gly Pro Gly Thr Met Val Thr Val Ser Ser
        130                 135

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

His Ser Val Gly Thr Asn
1               5

<210> SEQ ID NO 18
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Ala Ser
1

<210> SEQ ID NO 19
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 19

Gln Gln Thr Gln Ser Trp Pro Leu Thr
1               5

<210> SEQ ID NO 20
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Val Phe Lys Phe Gln Ile Leu Gly Leu Leu Leu Phe Trp Ile Ser
1               5                   10                  15

Ala Ser Arg Gly Asp Ile Val Leu Thr Gln Ser Pro Thr Thr Leu Ser
            20                  25                  30

Val Thr Pro Gly Glu Thr Val Ser Leu Ser Cys Arg Ala Ser His Ser
        35                  40                  45

Val Gly Thr Asn Leu His Trp Tyr Gln Gln Lys Thr Asn Glu Ser Pro
    50                  55                  60

Arg Leu Leu Ile Lys Asp Ala Ser Gln Ser Met Ser Gly Ile Pro Ser
65                  70                  75                  80

Arg Phe Ser Ala Ser Gly Ser Gly Thr Asp Phe Thr Leu Asn Ile Lys
                85                  90                  95

Asn Val Glu Phe Asp Asp Val Ser Ser Tyr Phe Cys Gln Gln Thr Gln
            100                 105                 110

Ser Trp Pro Leu Thr Phe Gly Ser Gly Thr Lys Leu Glu Ile Lys
        115                 120                 125

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Phe Thr Phe Arg Asn Tyr Tyr
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Gly Ser Gly Gly Asp Phe Thr
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 23

Ala Arg Ala Tyr Gly Tyr Phe Asp Tyr
1               5

<210> SEQ ID NO 24
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Asp Ile Arg Leu Ser Leu Ala Phe Leu Val Leu Phe Ile Glu Asp
1               5                   10                  15

Val Gln Cys Glu Val Gln Leu Val Glu Ser Gly Gly Gly Leu Val Gln
            20                  25                  30

Pro Gly Arg Ser Met Lys Leu Ser Cys Ala Ala Ser Gly Phe Thr Phe
        35                  40                  45

Arg Asn Tyr Tyr Met Ala Trp Val Arg Gln Ala Pro Thr Arg Gly Leu
    50                  55                  60

Glu Trp Val Ala Ser Thr Gly Ser Gly Gly Asp Phe Thr Tyr Tyr Arg
65                  70                  75                  80

Asp Ser Val Lys Gly Arg Phe Thr Ile Ser Arg Asp Thr Ala Glu Asn
                85                  90                  95

Thr Leu Tyr Leu Gln Met Asp Ser Leu Arg Ser Glu Asp Thr Ala Thr
            100                 105                 110

Tyr Tyr Cys Ala Arg Ala Tyr Gly Tyr Phe Asp Tyr Trp Gly Gln Gly
        115                 120                 125

Val Arg Val Thr Val Ser Ser
    130                 135

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Ser Leu Leu Tyr Asn Glu Asn Asn Lys Asn Tyr
1               5                   10

<210> SEQ ID NO 26
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Trp Ala Ser
1

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                                peptide

<400> SEQUENCE: 27

Gln Gln Tyr Phe Arg Phe Pro Arg Thr
1               5

<210> SEQ ID NO 28
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Glu Ser Gln Thr Gln Val Leu Met Ser Leu Leu Leu Trp Val Ala
1               5                   10                  15

Gly Ser Cys Gly Asp Ile Val Met Thr Gln Thr Pro Ser Ser Gln Ala
            20                  25                  30

Val Ser Ala Gly Glu Lys Val Thr Met Ser Cys Thr Ser Gly Gln Ser
        35                  40                  45

Leu Leu Tyr Asn Glu Asn Asn Lys Asn Tyr Leu Ala Trp Tyr Gln Leu
    50                  55                  60

Lys Pro Gly Gln Ser Pro Arg Leu Leu Ile Tyr Trp Ala Ser Thr Arg
65                  70                  75                  80

Glu Ser Gly Val Pro Asp Arg Phe Ile Gly Ser Gly Ser Gly Thr Tyr
                85                  90                  95

Phe Thr Leu Thr Ile Ser Ser Val Gln Ala Glu Asp Leu Ala Val Tyr
            100                 105                 110

Tyr Cys Gln Gln Tyr Phe Arg Phe Pro Arg Thr Phe Gly Gly Gly Thr
        115                 120                 125

Lys Leu Glu Leu Lys
    130

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Phe Ser Leu Thr Asn Tyr Asn
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ile Trp Ser Gly Gly Ser Ala
1               5

<210> SEQ ID NO 31
<211> LENGTH: 12
<212> TYPE: PRT
<213> ORGANISM: Artificial Sequence
<220> FEATURE:
```

<223> OTHER INFORMATION: Description of Artificial Sequence: Synthetic
    peptide

<400> SEQUENCE: 31

Thr Arg Asp Gln Leu Gly Gly Trp Tyr Phe Asp Phe
1               5                   10

<210> SEQ ID NO 32
<211> LENGTH: 137
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 32

Met Ala Val Leu Gly Leu Leu Leu Cys Leu Val Thr Phe Pro Ser Cys
1               5                   10                  15

Ala Leu Ser Gln Val Gln Leu Lys Glu Ser Gly Pro Gly Leu Val Gln
            20                  25                  30

Pro Ser Gln Thr Leu Ser Leu Thr Cys Thr Val Ser Gly Phe Ser Leu
        35                  40                  45

Thr Asn Tyr Asn Ile His Trp Val Arg Gln Pro Pro Gly Lys Gly Leu
    50                  55                  60

Glu Trp Met Gly Ala Ile Trp Ser Gly Gly Ser Ala Asp Tyr Asp Ser
65                  70                  75                  80

Ala Leu Lys Ser Arg Leu Ser Ile Ser Arg Asp Thr Ser Lys Ser Gln
                85                  90                  95

Val Phe Leu Lys Met Asp Asn Leu Gln Thr Glu Asp Thr Ala Ile Tyr
            100                 105                 110

Tyr Cys Thr Arg Asp Gln Leu Gly Gly Trp Tyr Phe Asp Phe Trp Gly
        115                 120                 125

Pro Gly Thr Lys Val Thr Val Ser Ser
    130                 135

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 33

Lys Ser Leu Leu Ser Ile Glu Gly Ile Asn Ser
1               5                   10

<210> SEQ ID NO 34
<211> LENGTH: 3
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 34

Arg Met Ser
1

<210> SEQ ID NO 35
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 35

Ala Gln Phe Leu Glu Phe Pro Phe Thr
1               5

<210> SEQ ID NO 36
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Lys Phe Pro Ala Gln Phe Leu Gly Leu Met Val Leu Cys Phe Pro
1               5                   10                  15

Gly Ala Thr Gly Asp Asn Val Leu Thr Gln Ala Pro Leu Ala Val Ser
            20                  25                  30

Val Thr Pro Gly Glu Ser Ala Ser Ile Ser Cys Arg Ser Ser Lys Ser
        35                  40                  45

Leu Leu Ser Ile Glu Gly Ile Asn Ser Leu Tyr Trp Tyr Leu Gln Lys
    50                  55                  60

Pro Gly Lys Ser Pro Gln Leu Leu Leu Phe Arg Met Ser Asn Leu Ala
65                  70                  75                  80

Ser Gly Val Pro Asp Arg Phe Ser Gly Ser Gly Ser Glu Thr Asp Phe
                85                  90                  95

Thr Leu Lys Ile Ser Gln Val Glu Thr Glu Asp Val Gly Val Tyr Tyr
            100                 105                 110

Cys Ala Gln Phe Leu Glu Phe Pro Phe Thr Phe Gly Ser Gly Thr Lys
        115                 120                 125

Leu Glu Ile Lys
    130

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Phe Ser Phe Ser Asp Tyr Tyr
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Ser Tyr Asp Gly Ser Gly Ser
1               5

<210> SEQ ID NO 39
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 39

Ala Arg Gly Gly Gly Leu Asp Tyr
1               5

<210> SEQ ID NO 40
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Asp Ile Arg Leu Ser Leu Val Phe Leu Val Leu Phe Ile Lys Gly
1               5                   10                  15

Val Gln Cys Glu Val Gln Leu Val Glu Ser Asp Gly Gly Leu Val Gln
            20                  25                  30

Pro Gly Arg Ser Leu Lys Leu Ser Cys Ala Ala Ser Gly Phe Ser Phe
        35                  40                  45

Ser Asp Tyr Tyr Met Ala Trp Val Arg Gln Ala Pro Thr Lys Gly Leu
    50                  55                  60

Glu Trp Val Ala Thr Ile Ser Tyr Asp Gly Ser Gly Ser Tyr Tyr Arg
65                  70                  75                  80

Asp Ser Val Lys Gly Arg Phe Thr Val Ser Arg Asp Asn Ala Lys Thr
                85                  90                  95

Thr Leu Tyr Leu Gln Met Asp Ser Leu Arg Ser Glu Asp Thr Ala Thr
            100                 105                 110

Tyr Tyr Cys Ala Arg Gly Gly Gly Leu Asp Tyr Trp Gly Gln Gly Val
        115                 120                 125

Met Val Thr Val Ser Ser
        130

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Ser Leu Leu Tyr Asn Lys Asn Lys Lys Asn Tyr
1               5                   10

<210> SEQ ID NO 42
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Trp Ala Ser
1

<210> SEQ ID NO 43
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Gln Tyr Tyr Thr Phe Pro Thr
1               5

<210> SEQ ID NO 44
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Glu Ser Gln Thr Gln Val Leu Met Ser Leu Leu Leu Trp Val Ser
1               5                   10                  15

Gly Thr Cys Gly Asp Ile Val Met Thr Gln Thr Pro Ser Ser Gln Ala
            20                  25                  30

Val Ser Ala Gly Ala Lys Val Thr Leu Ser Cys Lys Ser Ser Gln Ser
        35                  40                  45

Leu Leu Tyr Asn Lys Asn Lys Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Ile Gly Ser Gly Ser Gly Thr Asp
                85                  90                  95

Phe Thr Leu Thr Ile Ser Ser Val Gln Ala Glu Asp Leu Ala Ile Tyr
            100                 105                 110

Tyr Cys Gln Gln Tyr Tyr Thr Phe Pro Thr Phe Gly Ala Gly Thr Lys
        115                 120                 125

Leu Glu Leu Lys
    130

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Phe Thr Phe Ser Asp Tyr Asn
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ile Ser Tyr Asn Gly Ser Glu Ile
1               5

<210> SEQ ID NO 47
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Arg His Trp Arg Glu Tyr Tyr Ser Ser Tyr Ser Ser Tyr Val Met
1               5                   10                  15
Asp Ala

<210> SEQ ID NO 48
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Asp Ile Arg Leu Ser Leu Val Phe Leu Val Leu Phe Met Lys Gly
1               5                   10                  15

Val Gln Cys Glu Val Gln Leu Val Glu Phe Gly Gly Gly Leu Val Gln
            20                  25                  30

Pro Gly Arg Ser Leu Lys Leu Ser Cys Ala Ala Ser Gly Phe Thr Phe
        35                  40                  45

Ser Asp Tyr Asn Leu Ala Trp Val Arg Gln Ala Pro Lys Lys Gly Leu
    50                  55                  60

Glu Trp Val Ala Thr Ile Ser Tyr Asn Gly Ser Glu Ile Tyr Tyr Arg
65                  70                  75                  80

Asp Ser Val Lys Gly Arg Phe Thr Ile Ser Arg Asp Asn Ala Lys Asn
                85                  90                  95

Thr Leu Tyr Leu Gln Met Asp Ser Leu Arg Ser Glu Asp Thr Ala Thr
            100                 105                 110

Tyr Tyr Cys Ala Arg His Trp Arg Glu Tyr Tyr Ser Ser Tyr Ser Ser
        115                 120                 125

Tyr Val Met Asp Ala Trp Gly Gln Gly Ala Ser Val Thr Val Ser Ser
    130                 135                 140

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Ser Leu Leu Gly Ser Lys Gly Ile Asn Phe
1               5                   10

<210> SEQ ID NO 50
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Met Ser
1
```

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ala Gln Phe Leu Glu Tyr Pro Asn Ser
1               5

<210> SEQ ID NO 52
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Lys Phe Pro Ala Gln Phe Leu Gly Leu Ile Val Leu Cys Ile Pro
1               5                   10                  15

Gly Ala Thr Gly Asp Ile Val Leu Thr Gln Ala Pro Leu Ser Val Ser
                20                  25                  30

Val Thr Pro Gly Glu Ser Ala Ser Ile Ser Cys Arg Ser Ser Lys Ser
            35                  40                  45

Leu Leu Gly Ser Lys Gly Ile Asn Phe Leu Tyr Trp Tyr Leu Gln Lys
        50                  55                  60

Pro Gly Lys Ser Pro Gln Leu Leu Ile Tyr Arg Met Ser Asn Leu Ala
65                  70                  75                  80

Ser Gly Val Pro Asp Arg Phe Ser Gly Ser Gly Ser Glu Thr Asp Phe
                85                  90                  95

Ile Leu Lys Ile Ser Lys Val Glu Thr Glu Asp Val Gly Val Tyr Tyr
            100                 105                 110

Cys Ala Gln Phe Leu Glu Tyr Pro Asn Ser Phe Gly Ala Gly Thr Lys
        115                 120                 125

Leu Glu Leu Lys
    130

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Phe Ser Leu Thr Asn Tyr Asn
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Met Trp Ser Gly Gly Asn Thr

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Arg Asp Ser Gly Tyr Gly Glu Gly Arg Leu Asp Tyr
1               5                   10

<210> SEQ ID NO 56
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Ala Val Arg Val Leu Leu Leu Cys Leu Val Thr Phe Pro Thr Cys
1               5                   10                  15

Ala Leu Ser Gln Val Gln Leu Met Glu Ser Gly Pro Gly Leu Val Gln
            20                  25                  30

Pro Ser Glu Thr Leu Ser Leu Thr Cys Thr Val Ser Gly Phe Ser Leu
        35                  40                  45

Thr Asn Tyr Asn Ile His Trp Val Arg Gln Pro Pro Gly Lys Gly Leu
    50                  55                  60

Glu Trp Met Gly Leu Met Trp Ser Gly Gly Asn Thr Asp Tyr Asn Ser
65                  70                  75                  80

Ala Leu Lys Ser Arg Leu Thr Ile Ser Arg Asp Thr Ser Lys Asn Gln
                85                  90                  95

Val Phe Leu Lys Met Asn Ser Leu Gln Ser Glu Asp Thr Thr Thr Tyr
            100                 105                 110

Tyr Cys Ala Arg Asp Ser Gly Tyr Gly Glu Gly Arg Leu Asp Tyr Trp
        115                 120                 125

Gly Gln Gly Val Met Val Thr Val Ser Ser
    130                 135

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

His Ser Val Gly Thr Asn
1               5

<210> SEQ ID NO 58
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Tyr Val Ser
1

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Gln Thr Gln Ser Trp Pro Leu Thr
1               5

<210> SEQ ID NO 60
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Val Phe Lys Phe Gln Ile Leu Gly Leu Leu Leu Phe Trp Ile Ser
1               5                   10                  15

Ala Ser Arg Gly Asp Ile Val Leu Thr Gln Ser Pro Thr Thr Leu Ser
            20                  25                  30

Val Thr Pro Gly Glu Thr Val Ser Leu Ser Cys Arg Ala Ser His Ser
        35                  40                  45

Val Gly Thr Asn Leu His Trp Tyr Gln Gln Lys Pro Asn Glu Ser Pro
    50                  55                  60

Arg Leu Leu Ile Lys Tyr Val Ser Gln Ser Asn Ser Gly Ile Pro Ser
65                  70                  75                  80

Arg Phe Ser Ala Ser Gly Ser Gly Thr Asp Phe Thr Leu Asn Ile Lys
                85                  90                  95

Asn Val Glu Phe Asn Asp Val Ser Ser Tyr Phe Cys Gln Gln Thr Gln
            100                 105                 110

Ser Trp Pro Leu Thr Phe Gly Ala Gly Thr Lys Leu Glu Ile Lys
        115                 120                 125

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Phe Thr Phe Arg Asn Tyr Tyr
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Thr Gly Thr Gly Gly Asp Phe Thr
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ala Arg Ala Tyr Gly Tyr Phe Asp Tyr
1               5

<210> SEQ ID NO 64
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Asp Ile Arg Leu Ser Leu Ala Phe Leu Val Leu Phe Ile Lys Gly
1               5                   10                  15

Val Gln Cys Glu Val Gln Leu Val Glu Ser Gly Gly Gly Leu Val Gln
            20                  25                  30

Pro Gly Arg Ser Met Lys Leu Ser Cys Ser Ala Ser Gly Phe Thr Phe
        35                  40                  45

Arg Asn Tyr Tyr Met Ala Trp Val Arg Gln Ala Pro Thr Arg Gly Leu
    50                  55                  60

Glu Trp Val Ala Ser Thr Gly Thr Gly Gly Asp Phe Thr Tyr Tyr Arg
65                  70                  75                  80

Asp Ser Val Lys Gly Arg Phe Thr Ile Ser Arg Asp Thr Ala Glu Asn
                85                  90                  95

Thr Leu Tyr Leu Gln Met Asp Ser Leu Arg Ser Glu Asp Thr Ala Thr
            100                 105                 110

Tyr Tyr Cys Ala Arg Ala Tyr Gly Tyr Phe Asp Tyr Trp Gly Gln Gly
        115                 120                 125

Val Lys Val Thr Val Ser Ser
    130                 135

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

His Ser Val Gly Thr Asn
1               5

<210> SEQ ID NO 66
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Tyr Val Ser

```
<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Gln Thr Gln Ser Trp Pro Leu Thr
1               5

<210> SEQ ID NO 68
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Val Phe Lys Phe Gln Ile Leu Gly Leu Leu Phe Trp Ile Ser
1               5                   10                  15

Ala Ser Arg Gly Asp Ile Val Leu Thr Gln Ser Pro Thr Thr Leu Ser
            20                  25                  30

Val Thr Pro Gly Glu Thr Val Ser Leu Ser Cys Arg Ala Ser His Ser
        35                  40                  45

Val Gly Thr Asn Leu His Trp Tyr Gln Gln Lys Thr Asn Glu Ser Pro
50                  55                  60

Arg Leu Leu Ile Lys Tyr Val Ser Gln Ser Asn Ser Gly Ile Pro Ser
65                  70                  75                  80

Arg Phe Ser Ala Ser Gly Ser Gly Thr Asp Phe Thr Leu Asn Ile Lys
                85                  90                  95

Asp Val Glu Phe Asp Asp Val Ser Ser Tyr Phe Cys Gln Gln Thr Gln
            100                 105                 110

Ser Trp Pro Leu Thr Phe Gly Ser Gly Thr Lys Leu Glu Ile Lys
        115                 120                 125

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Phe Ile Phe Arg Asn Tyr Tyr
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Thr Gly Thr Gly Gly Asp Phe Thr
1               5
```

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ala Arg Ala Tyr Gly Tyr Phe Asp Tyr
1               5

<210> SEQ ID NO 72
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met Asp Ile Arg Leu Ser Leu Ala Phe Leu Val Leu Phe Ile Lys Gly
1               5                   10                  15

Val Gln Cys Glu Val Gln Leu Val Glu Ser Gly Gly Gly Leu Val Gln
            20                  25                  30

Pro Gly Arg Ser Met Lys Leu Ser Cys Ser Ala Ser Gly Phe Ile Phe
        35                  40                  45

Arg Asn Tyr Tyr Met Ala Trp Val Arg Gln Ala Pro Thr Lys Gly Leu
    50                  55                  60

Glu Trp Val Ala Ser Thr Gly Thr Gly Gly Asp Phe Thr Tyr Tyr Arg
65                  70                  75                  80

Asp Ser Val Lys Gly Arg Phe Thr Ile Ser Arg Asp Thr Ala Glu Ser
                85                  90                  95

Thr Leu Tyr Leu Gln Met Asp Ser Leu Lys Ser Glu Asp Thr Ala Thr
            100                 105                 110

Tyr Tyr Cys Ala Arg Ala Tyr Gly Tyr Phe Asp Tyr Trp Gly Gln Gly
        115                 120                 125

Val Lys Val Thr Val Ser Ser
    130                 135

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Asn Ile Tyr Lys Tyr
1               5

<210> SEQ ID NO 74
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Asn Ile Asn
1

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Tyr Gln Tyr Asn Ser Gly Arg Ala
1               5

<210> SEQ ID NO 76
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Ala Pro Val Gln Leu Leu Gly Leu Leu Leu Leu Cys Leu Arg Ala
1               5                   10                  15

Met Arg Cys Asp Ile Gln Met Thr Gln Ser Pro Ser Leu Leu Ser Ala
                20                  25                  30

Ser Glu Gly Asp Arg Val Thr Leu Ser Cys Lys Ala Ser Gln Asn Ile
        35                  40                  45

Tyr Lys Tyr Leu Asn Trp Tyr Gln Gln Lys Leu Gly Glu Ala Pro Lys
    50                  55                  60

Leu Leu Ile Tyr Asn Ile Asn Asn Leu Gln Thr Gly Ile Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Val Ala Thr Tyr Tyr Cys Tyr Gln Tyr Asn Ser
            100                 105                 110

Gly Arg Ala Phe Gly Gly Gly Thr Lys Leu Glu Leu Lys
        115                 120                 125

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Phe Thr Phe Ser Asp Tyr Trp
1               5

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ile Arg Asn Lys Leu Asn Asn Tyr Val Thr
1               5                   10

```
<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Arg Ile Gln Arg Val Ile Thr Thr Gly Glu Tyr Phe Asp Tyr
1               5                   10                  15

<210> SEQ ID NO 80
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Asp Leu Arg Leu Thr Tyr Val Phe Ile Val Ala Ile Leu Lys Gly
1               5                   10                  15

Val Leu Cys Glu Val Lys Leu Glu Ser Gly Gly Gly Leu Val Gln
                20                  25                  30

Pro Gly Met Ser Val Lys Leu Ser Cys Ala Thr Ser Gly Phe Thr Phe
            35                  40                  45

Ser Asp Tyr Trp Met Glu Trp Val Arg Gln Ala Pro Gly Lys Gly Leu
        50                  55                  60

Glu Trp Val Ala Glu Ile Arg Asn Lys Leu Asn Asn Tyr Val Thr Asn
65                  70                  75                  80

Tyr Gly Lys Pro Val Arg Gly Arg Phe Thr Ile Ser Arg Asp Asp Ser
                85                  90                  95

Lys Ser Ile Val Tyr Leu Gln Val Asn Ser Ile Arg Ser Glu Asp Thr
            100                 105                 110

Gly Ile Tyr Tyr Cys Thr Arg Ile Gln Arg Val Ile Thr Thr Gly Glu
        115                 120                 125

Tyr Phe Asp Tyr Trp Gly Gln Gly Val Met Val Thr Val Ser Ser
    130                 135                 140

<210> SEQ ID NO 81
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
cagagtctct tagatagtga tggaaacacc tat                               33

<210> SEQ ID NO 82
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82 ttggtatcc                                                          9

<210> SEQ ID NO 83
```

```
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
atgcaagcta cccatgctcc attcacg                                         27

<210> SEQ ID NO 84
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
atgagtcctg tccagtccct gttttatta ttgctttgga ttctgggaac caaaggtgat      60
gttgtgctga cccagactcc atccatattg tctgctacca ttggacaatc ggtctccatc    120
tcttgcaggt caagtcagag tctcttagat agtgatggaa acacctattt atattggttc    180
ctacagaggc caggccagtc tccacagcgt ctaatttatt tggtatccaa cctgggatct    240
ggggtcccca acaggttcag tggcagtggg tcaggaacag atttcacact caaaatcagt    300
ggggtggagg ctggagattt gggagtttat tactgcatgc aagctaccca tgctccattc    360
acgttcggct cagggacgaa gttggaaata aaa                                 393

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ggatttgact tcaaaactta tgcc                                            24

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ataagcacta agggtcataa ttatgcaaca                                      30

<210> SEQ ID NO 87
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
actgtggcag ggtataattt tgattac                                         27

<210> SEQ ID NO 88
<211> LENGTH: 408
<212> TYPE: DNA
```

<213> ORGANISM: Artificial Sequence
<220> FEATURE:
<223> OTHER INFORMATION: Description of Artificial Sequence: Synthetic
      polynucleotide

<400> SEQUENCE: 88

```
atggttctcc tggagttggt ttccgtgatt gctcttttc aaggcgtgca ttgtgaggtg      60
cagcttgttg agtctggtgg agggctggtg cagcctaaag ggtcattgaa actctcatgt    120
gcagcctctg gatttgactt caaaacttat gccatgagct gggtccgcca ggctccagga    180
aagggtctgg attggattgt taccataagc actaagggtc ataattatgc aacactttat    240
gctgactcag tgaaagagag attcaccatc tccagagatg attcacaaag catggtttac    300
ttgcaaatga caacttgaa aactgaggac acagccttgt attactgtac tgtggcaggg    360
tataattttg attactgggg ccaaggagtc atggtcacag tctcctca                408
```

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89

```
cagagcgtgg gtattaat                                                   18
```

<210> SEQ ID NO 90
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90

```
acggcatcc                                                              9
```

<210> SEQ ID NO 91
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91

```
ctgcaatatg gctcccttcc gttcacg                                         27
```

<210> SEQ ID NO 92
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92

```
atggagtcac atactagggt cttcatattc ctgctgctct ggttgtctgg aggtgatggg     60
gaaactgtga tgacccagtc tcccacatcc atgcccacat caataggaga gagggtcacc    120
ctgaactgca aggccagtca gagcgtgggt attaatgtag actggtacca acagacacca    180
gggcagtctc cgaaactgct gatatatacg gcatccaacc ggcacactgg ggtccctgat    240
```

```
cgcttcgcag gcagtgggtc tgggagagat ttcactctca ccatcagcaa cgtggaggct      300
gaagacctgg ttgtttatta ctgtctgcaa tatggctccc ttccgttcac gtttggagct      360
gggaccaagc tggagctgaa a                                                 381

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
ggattcactt tcagtaactt tgac                                              24

<210> SEQ ID NO 94
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
attacttatg atggcagtag aact                                              24

<210> SEQ ID NO 95
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
gcaagacatg gaagctccta ctactggttc tttgacttc                              39

<210> SEQ ID NO 96
<211> LENGTH: 417
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
atggacatca ggctcagctt ggctttcctt gtccttttca taaaagatgt ccagtgtgag       60
gtgcagctgg tggagtctgg gggaggcttg gtgcagcctg gaaggtccat gatactctcc      120
tgtgcagcct caggattcac tttcagtaac tttgacatgg cctgggtccg ccaggctcca      180
aagatgggtc tggagtgggt cgcaaccatt acttatgatg gcagtagaac taactatcga      240
gactccgtga agggccgatt cactatctcc agagatagtg caaagaacac cctatacctg      300
caaatggaca gtctgacgtc tgaggacacg gccacttatt actgtgcaag acatggaagc      360
tcctactact ggttctttga cttctggggc ccaggaacca tggtcaccgt gtcctca         417

<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 97
catagtgttg gcacaaat 18

<210> SEQ ID NO 98
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98 gatgcctca 9

<210> SEQ ID NO 99
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
caacagactc aaagttggcc cctcacg 27

<210> SEQ ID NO 100
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
atggtgttca aatttcagat ccttggactt ctgcttttct ggatttcagc ctctagaggg      60
gacatcgtgt tgactcagtc tccaaccacc ctgtctgtga ctccaggaga gacagtcagt     120
ctttcctgca gggctagtca tagtgttggc acaaatctac actggtatca gcaaaaaaca     180
aatgagtccc caaggcttct catcaaggat gcctcacagt ccatgtccgg gatcccctcc     240
aggttcagtg ccagtggatc aggacagat tttactctca acatcaaaaa tgtggagttt      300
gatgatgtct cgagttattt ttgtcaacag actcaaagtt ggccccctca cgttcggttct     360 gggaccaagc tggagatcaa a 381

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ggattcactt tcagaaacta ttac 24

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102

```
actggtagtg gtggtgattt cact                                              24
```

<210> SEQ ID NO 103
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103

```
gcaagggcct atggatactt tgattac                                           27
```

<210> SEQ ID NO 104
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104

```
atggacatca ggctcagttt ggctttcctt gtccttttca tagaagatgt ccagtgtgag       60
gtgcagctgg tggagtctgg gggaggccta gtgcagcctg gaaggtccat gaaactctcc     120
tgtgcagcct caggattcac tttcagaaac tattacatgg cctgggtccg ccaggctcca     180 acgagggggtc tggagtgggt cgcatccact ggtagtggtg gtgatttcac ttactatcga    240
gactccgtga agggccgatt cactatctcc agagatactg cagaaaacac cctataccta     300
caaatggaca gtctgaggtc tgaggacacg gccacgtatt actgtgcaag ggcctatgga     360
tactttgatt actggggcca aggagtcagg gtcacagtct cctca                     405
```

<210> SEQ ID NO 105
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105

```
cagagtcttt tatacaatga aaacaataag aactac                                36
```

<210> SEQ ID NO 106
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106

```
tgggcatcc                                                               9
```

<210> SEQ ID NO 107
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107

```
cagcaatatt ttaggtttcc tcggacg                                           27
```

<210> SEQ ID NO 108
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
atggaatcac agacacaggt cctcatgtcc ctgctgctct gggtagctgg ttcctgtggg      60
gacattgtga tgacccagac tccatcctcc caggctgtgt cagcagggga gaaggtcact     120
atgagctgca cgtccggtca gagtctttta tacaatgaaa acaataagaa ctacttggcc     180
tggtaccagc tgaaaccggg gcagtctcct agactgctga tctactgggc atccactagg     240
gaatctgggg tccctgatcg cttcataggc agtggatctg ggacgtattt cactctgacc     300
atcagcagtg tgcaggcaga agacctggct gtttattact gccagcaata ttttaggttt     360
cctcggacgt tcggtggagg caccaagctg gaattgaaa                            399

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ggattctcac taaccaacta taat                                             24

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
atttggagtg gtggaagtgc a                                                21

<210> SEQ ID NO 111
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
accagagatc aactgggagg ctggtacttt gacttc                                36

<210> SEQ ID NO 112
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112
atggctgtcc tggggctgtt gctctgcctg gtgacatttc caagctgtgc cctgtcccag      60
gtgcagctga aggagtcagg acctggtctg gtgcagccct cacagaccct gtccctcacc     120

| | |
|---|---|
| tgcactgtct ctggattctc actaaccaac tataatatac actgggttcg acagcctcca | 180 |
| ggaaagggtc tggagtggat gggagcaatt tggagtggtg aaagtgcaga ttatgattca | 240 |
| gctctcaaat cccgactgag catcagcagg gacacctcca agagccaagt tttcttgaaa | 300 |
| atggacaatc tgcaaactga agacacagcc atttactact gtaccagaga tcaactggga | 360 |
| ggctggtact ttgacttctg gggcccagga accaaggtca ccgtgtcctc a | 411 |

<210> SEQ ID NO 113
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113

| | |
|---|---|
| aagagtctgc taagtattga gggcattaat tcc | 33 |

<210> SEQ ID NO 114
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114

| | |
|---|---|
| cggatgtcc | 9 |

<210> SEQ ID NO 115
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115

| | |
|---|---|
| gcacagtttc tagaatttcc attcacg | 27 |

<210> SEQ ID NO 116
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116

| | |
|---|---|
| atgaagtttc ctgctcagtt tcttggactg atggtgctct gttttcctgg agccactggg | 60 |
| gataatgtgt tgactcaagc tccactcgct gtttctgtca ctcctggaga gtcagcttcc | 120 |
| atctcctgca ggtctagtaa gagtctgcta agtattgagg cattaattc cttgtattgg | 180 |
| taccttcaga agccaggaaa gtctcctcag ctcctgcttt tcggatgtc caaccttgcc | 240 |
| tcaggagttc cagacaggtt tagtggcagt gggtcagaaa cagattttac actgaaaatc | 300 |
| agtcaggtgg agactgagga tgttggcgtt tattactgtg cacagtttct agaatttcca | 360 |
| ttcacgttcg gctcagggac gaagttggaa ataaaa | 396 |

<210> SEQ ID NO 117
<211> LENGTH: 24
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 117
ggattcagtt tcagtgacta ttac                                              24

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
attagttatg atggtagtgg tagt                                              24

<210> SEQ ID NO 119
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gcaagagggg gtggtcttga ttac                                              24

<210> SEQ ID NO 120
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120
atggacatca ggctcagctt ggttttcctt gtccttttca taaaggtgt ccagtgtgag        60 gtgcagctgg tggagtctga tggaggctta gtgcagcctg gaaggtccct aaaactctcc     120
tgtgcagcct caggattcag tttcagtgac tattacatgg cctgggtccg ccaggctcca     180
acgaaggggc tggagtgggt cgcaaccatt agttatgatg gtagtggtag ttactatcga     240
gactccgtga agggccgatt cactgtctcc agagataatg caaaaaccac cctatacctg     300
caaatggaca gtctgaggtc tgaggacacg gccacttatt actgtgcaag agggggtggt     360
cttgattact ggggccaagg agtcatggtc acagtctcct ca                        402

<210> SEQ ID NO 121
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
cagagtcttt tatacaataa aaacaaaaag aactac                                 36

<210> SEQ ID NO 122
<211> LENGTH: 9
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 122 tgggcatcc                                                                  9

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
cagcagtact ataccttcc cacc                                                 24

<210> SEQ ID NO 124
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
atggaatcac agacacaggt cctcatgtcc ctgctgctct gggtatctgg tacctgtggg         60
gacattgtga tgacccagac tccatcctcc caggctgtgt cagcagggc gaaggtcact         120 ttgagctgca gtccagtca gagtctttta tacaataaaa acaaaaagaa ctacttggcc         180
tggtaccagc agaaaccagg gcagtctcct aaactgctga tctactgggc atccactagg         240
gaatctgggg tccctgatcg cttcataggc agtggatctg ggacagattt cactctgacc         300
atcagcagtg tgcaggcaga agacctggct atttattact gccagcagta ctataccttt         360 cccaccttg gggctgggac caagctggaa ctgaaa                                   396

<210> SEQ ID NO 125
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ggattcactt tcagtgacta taat                                               24

<210> SEQ ID NO 126
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
attagttata atggtagtga aatt                                               24

<210> SEQ ID NO 127
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 127
gcaagacatt ggcgggaata ctatagcagt tattcctcct atgttatgga tgcc    54

<210> SEQ ID NO 128
<211> LENGTH: 432
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128
atggacatca ggctcagctt ggttttcctt gtcctttta tgaaaggtgt ccagtgtgag    60
gtgcagctgg tggagtttgg gggaggctta gtgcagcctg gaaggtccct gaaactctcc   120
tgtgcagcct caggattcac tttcagtgac tataatttgg cctgggtccg ccaggctcca   180
aagaagggtc tggagtgggt cgcaaccatt agttataatg gtagtgaaat ttactatcga   240
gactccgtga agggccgatt caccatctcc agagataatg caaaaaacac cctatatctg   300
cagatggaca gtctgaggtc tgaggacacg gccacttatt actgtgcaag acattggcgg   360
gaatactata gcagttattc ctcctatgtt atggatgcct ggggtcaagg agcttcagtc   420
actgtctcct ca                                                      432

<210> SEQ ID NO 129
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
aagagtcttc taggtagtaa gggcatcaat ttc                                33

<210> SEQ ID NO 130
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130 cggatgtcc                                                            9

<210> SEQ ID NO 131
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
gcacagtttc tagaatatcc gaactcg                                       27

<210> SEQ ID NO 132
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132

```
atgaagtttc ctgctcagtt tcttggactg atagtgctct gtattcctgg agccactggg      60
gatattgtgt tgactcaagc tccactctct gtttctgtca ctcctggaga gtcagcttcc     120
atctcctgca ggtctagtaa gagtcttcta ggtagtaagg gcatcaattt cttgtattgg     180
taccttcaga agccaggaaa gtctcctcag ctcctgatat atcggatgtc aaccttgcc     240
tcaggagttc cagacaggtt tagtggtagt gggtcagaaa cagattttat actgaagatc     300
agtaaggtgg agactgagga tgttggcgtt tattactgtg cacagtttct agaatatccg     360
aactcgtttg gagctgggac caagttggaa ctgaaa                                396
```

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 133

```
gggttctcgc taaccaacta taac                                              24
```

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 134

```
atgtggagtg gtggaaacac a                                                 21
```

<210> SEQ ID NO 135
<211> LENGTH: 39
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 135

```
gccagagatt ctggttacgg agagggtcgt cttgattac                              39
```

<210> SEQ ID NO 136
<211> LENGTH: 414
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 136

```
atggctgtcc gggtactgtt gctctgcctg gtgacatttc aacctgtgc cctgtcccag       60
gtgcagctga tggagtcagg acctggcctg gtgcagccct cagagaccct gtccctcacc     120
tgcactgtct ctgggttctc gctaaccaac tataacattc actgggttcg acagcctcca     180
gggaaaggtc tggagtggat gggactaatg tggagtggtg gaaacacaga ttataattca     240
gctctcaaat cccgactgac catcagcagg gacacctcca agaaccaagt ttttcttaaaa     300
atgaacagtt tgcaaagtga agacacaacc acttactact gtgccagaga ttctggttac     360
ggagagggtc gtcttgatta ctggggccaa ggcgtcatgg tcacagtctc ctca            414
```

```
<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
catagtgttg gcacaaat                                                   18

<210> SEQ ID NO 138
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138 tatgtctca                                                              9

<210> SEQ ID NO 139
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
caacagactc aaagttggcc cctcacg                                         27

<210> SEQ ID NO 140
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140
atggtgttca aatttcagat ccttggactt ctgcttttct ggatttcagc ctctagaggg     60
gacatcgtgc tgactcagtc tccaaccacc ctgtctgtga ctccaggaga gacagtcagt    120
ctttcctgca gggctagcca tagtgttggc acaaatctac actggtatca gcaaaaacca    180
aatgagtctc caaggcttct catcaagtat gtctcacagt ccaattccgg gatcccctcc    240
aggttcagtg ccagtggatc agggacagat tttactctca acatcaaaaa tgtggaattt    300
aatgatgtct caagttattt ttgtcaacag actcaaagtt ggcccctcac gttcggtgct    360
gggaccaagc tggagatcaa a                                              381

<210> SEQ ID NO 141
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
ggattcactt tcagaaatta ttac                                            24
```

<210> SEQ ID NO 142
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 142
actggtactg gtggtgattt cact                                          24

<210> SEQ ID NO 143
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 143
gcaagggcct atgggtactt tgattac                                       27

<210> SEQ ID NO 144
<211> LENGTH: 405
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 144
atggacatca ggctcagttt ggctttcctt gtccttttca taaaaggtgt ccagtgtgag    60
gtgcagctgg tggagtctgg gggaggctta gtgcagcctg gaaggtccat gaaactctcc   120
tgttcagcct caggattcac tttcagaaat tattacatgg cctgggtccg ccaggctcca   180
acgaggggtc tggagtgggt cgcatccact ggtactggtg gtgatttcac ttactatcga   240
gactccgtga agggccgatt cactatctcc agagatactg cagaaaacac cctatactta   300
caaatggaca gtctgaggtc tgaggacacg gccacttatt actgtgcaag ggcctatggg   360
tactttgatt actggggcca aggagtcaag gtcacagtct cctca                   405

<210> SEQ ID NO 145
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 145
catagtgttg gcacaaat                                                 18

<210> SEQ ID NO 146
<211> LENGTH: 9
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 146 tatgtctca                                                            9

<210> SEQ ID NO 147
<211> LENGTH: 27

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
caacagactc aaagttggcc cctcacg                                          27

<210> SEQ ID NO 148
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 148
atggtgttca aatttcagat ccttggactt ctgcttttct ggatttcagc ctctagaggg      60
gacatcgtgc tgactcagtc tccaaccacc ctgtctgtga ctccaggaga gacagtcagt     120
ctttcctgca gggctagcca tagtgttggc acaaatctac actggtatca gcaaaaaaca     180
aatgagtctc caaggcttct catcaagtat gtctcacagt ccaattccgg gatcccctcc     240
aggttcagtg ccagtggatc agggacagat tttactctca acatcaaaga tgtggagttt     300
gatgatgtct caagttattt ttgtcaacag actcaaagtt ggccccctca cgttcggttct     360 gggaccaagc tggagatcaa a                                               381

<210> SEQ ID NO 149
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
ggattcattt tcagaaacta ttac                                             24

<210> SEQ ID NO 150
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
actggtactg gtggtgattt cact                                             24

<210> SEQ ID NO 151
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
gcaagggcct atgggtactt tgattac                                          27

<210> SEQ ID NO 152
<211> LENGTH: 405
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 152
atggacatca ggctcagttt ggctttcctt gtccttttca taaaaggtgt ccagtgtgag    60
gtgcagctgg tggagtctgg gggaggctta gtgcagcctg gaaggtccat gaaactctcc   120
tgttcagcct caggattcat tttcagaaac tattacatgg cctgggtccg ccaggctcca   180
acgaagggtc tggagtgggt cgcatccact ggtactggtg gtgatttcac ttactatcga   240
gactccgtga agggccgatt cactatctcc agagatactg cagaaagcac cctatactta   300
caaatggaca gtctgaagtc tgaggacacg gccacttatt actgtgcaag ggcctatggg   360
tactttgatt actggggcca aggagtcaag gtcacagtct cctca                   405

<210> SEQ ID NO 153
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
cagaatatct acaagtac                                                  18

<210> SEQ ID NO 154
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154 aatataaat                                                             9

<210> SEQ ID NO 155
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
tatcagtata acagtgggcg ggcg                                           24

<210> SEQ ID NO 156
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 156
atggctccag tacaacttct agggcttttg ctgctctgcc tccgagccat gagatgtgac    60
atccagatga cccagtctcc ttcactcctg tcagcatctg agggagacag agtcactctc   120
agctgcaaag caagtcagaa tatctacaag tacttaaact ggtatcagca aaagcttgga   180
gaagctccca aactcctgat atataatata ataatttgc aaacgggcat cccatcaagg    240
ttcagtggca gtggatctgg tacagatttc acacttacca tcagcagcct gcagcctgaa   300
```

```
gacgttgcca catattactg ctatcagtat aacagtgggc gggcgttcgg aggaggcacc    360
aagctggaat tgaaa                                                    375
```

<210> SEQ ID NO 157
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157

```
ggattcactt tcagtgacta ctgg                                           24
```

<210> SEQ ID NO 158
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158

```
attagaaata aacttaataa ttatgtaaca                                     30
```

<210> SEQ ID NO 159
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159

```
acaaggatac aacgggttat tactacgggg gaatactttg attac                    45
```

<210> SEQ ID NO 160
<211> LENGTH: 429
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 160

```
atggacttgc gactgactta tgtctttatt gttgctattt taaaaggtgt cttgtgtgag    60
gtgaaactgg aggaatctgg gggaggtttg gtgcaacctg gaatgtccgt gaaactctct   120
tgtgcaacct ctggattcac tttcagtgac tactggatgg agtgggtccg ccaggctcca   180
gggaaggggc tagaatgggt agctgaaatt agaataaaac ttaataatta tgtaacaaat   240
tatgggaagc ctgtgagagg cagattcacc atctcaagag atgattccaa agtatagtc    300 tacctgcagg tgaacagcat aagatctgaa gatactggta tttattactg tacaaggata   360
caacgggtta ttactacggg ggaatacttt gattactggg ccaagggggt catggtcaca   420
gtctcctca                                                           429
```

<210> SEQ ID NO 161
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

```
<400> SEQUENCE: 161

His His His His His His
1               5
```

TEM-1 DIAGNOSTIC ANTIBODIES

CROSS-REFERENCE TO RELATED APPLICATIONS

This application claims the benefit of U.S. Appl. No. 61/618,235, filed Mar. 30, 2012, the contents of which are incorporated herein by reference in their entirety.

TECHNICAL FIELD

The disclosure provided herein relates to rat monoclonal antibodies specific for TEM-1 and methods of producing and using the described antibodies.

BACKGROUND

Angiogenesis is a regulated process involving the formation of new blood vessels. It plays an essential role in normal growth, embryonic development, wound healing, and other physiological processes (Yancopoulos et al. (2000) Nature 407(6801):242-8). Moreover, de novo angiogenesis is involved in several disease states including cancer, where the formation of new "embryonic-like" blood vessels (referred to as neovascularization herein) appear that differ from normal vasculature with regards to structure and function (Hanahan and Weinberg (2000) Cell 100(1):57-70). A number of in vivo and in vitro studies have demonstrated biological differences between normal and disease-associated vasculature as determined using various model systems of angiogenesis offering the ability to develop novel anti-angiogenic compounds that can selectively inhibit vessel formation of the embryonic-type, tumor-associated endothelial-type for therapy of neovascular disease.

In light of these opportunities for therapy, an intense search for potential targets that can specifically inhibit tumor and other neovascular disease-associated endothelial cell growth and function is ongoing. In an attempt to identify such targets, strategies have been designed to identify cell surface antigens of tumor stroma as well as isolate specific proteins or RNA that are expressed in neovascular endothelial cells (Rettig et al. (1992) PNAS 89(22):10832-6; St. Croix et al. (2000) Science 289: 1197-1202). These strategies have identified a cell surface protein called tumor endothelial marker 1 (TEM-1), also known as endosialin or CD248. TEM-1 is expressed on tumor-associated pericytes, tumor stromal cells and directly on a subset of malignant cells. Pericytes are specialized cells that support the formation of blood vessels that support blood to tumors for their growth and survival. Expression of TEM-1 in tumors has been observed by several independent laboratories and experiments, and blocking endosialin function has been shown to inhibit tumor growth and metastasis.

In cancer it is believed that neovascularization is important to supply tumors with blood, providing nutrients to support largely uncontrolled growth. Thus, proteins, such as TEM-1, that are differentially associated with tumor vasculature have become potential therapeutic targets for the treatment of cancer. The development of antibodies that can specifically target TEM-1 offers the ability to treat these diseases. It is also understood that earlier detection of cancer improves survival rates and quality of life. To improve the likelihood of early detection and effective treatment, a need exists for non-invasive methods for detecting cancers, monitoring existing cancers, and assessing therapeutic efficacy.

SUMMARY

Provided herein are antibodies that bind to TEM-1. Also described are related polynucleotides capable of encoding the provided antibodies, cells expressing the provided antibodies, as well as associated vectors and detectable antibody labels. In addition, methods of using the provided antibodies are described. For example, the provided antibodies may be used to diagnose cancer; monitor cancer progression, regression, or stable disease; to determine whether or not a patient should be treated for cancer, or to determine whether or not a subject is afflicted with TEM-1-expressing cancer and thus may be amenable to treatment with a TEM-1-specific anti-cancer therapeutic.

TEM-1-Specific Antibodies

Described herein are isolated antibodies and antigen-binding fragments specific for TEM-1. In some embodiments, the antibodies or antigen-binding fragments are rat IgG, or derivatives thereof. In some embodiments the described antibodies are capable of binding to TEM-1 with a dissociation constant of $1 \times 10^{-8}$ M or less. Table 1 provides a summary of the antibodies described herein:

TABLE 1

Summary of TEM-1-specific antibodies

| | | Light Chain Sequences (SEQ ID NOs) | | | Heavy Chain Sequences (SEQ ID NOs) | | | ATCC |
| | Rat | | | | | | | Accession |
| Designation | Isotype | CDR 1 | CDR 2 | CDR 3 | CDR 1 | CDR 2 | CDR 3 | Number |
|---|---|---|---|---|---|---|---|---|
| 7D3 | IgG2a/κ | 1 | 2 | 3 | 5 | 6 | 7 | PTA-12538 |
| 7H12 | IgG1/κ | 9 | 10 | 11 | 13 | 14 | 15 | PTA-12545 |
| 9A5 | IgG2a/κ | 17 | 18 | 19 | 21 | 22 | 23 | PTA-12542 |
| 10H8 | IgG2a/κ | 25 | 26 | 27 | 29 | 30 | 31 | PTA-12546 |
| 11D1 | IgG2a/κ | 33 | 34 | 35 | 37 | 38 | 39 | PTA-12541 |
| 14G3 | IgG2a/κ | 41 | 42 | 43 | 45 | 46 | 47 | PTA-12539 |
| 15D10 | IgG2a/κ | 49 | 50 | 51 | 53 | 54 | 55 | PTA-12543 |
| 15F8 | IgG2a/κ | 57 | 58 | 59 | 61 | 62 | 63 | PTA-12540 |
| 16D2 | IgG2a/κ | 65 | 66 | 67 | 69 | 70 | 71 | PTA-12544 |
| 9G5 | IgG1/κ | 73 | 74 | 75 | 77 | 78 | 79 | PTA-12547 |

In addition to the described antibodies, also provided are polynucleotide sequences capable of encoding the described antibodies. Vectors comprising the described polynucleotides are also provided, as are cells expressing the antibodies provided herein. Also described are cells capable of expressing the disclosed vectors. These cells may be mammalian cells (such as CHO-K1 cells), insect cells (such as Sf7 cells), yeast cells, plant cells, or bacteria cells (such as *E. coli*). The described antibodies may also be produced by hybridoma cells, as described herein.

Methods of Using TEM-1-Specific Antibodies

Methods of using the described antibodies are also disclosed. For example, these antibodies may be useful for detecting the presence of TEM-1 in a biological sample, such as blood or serum; for quantifying the amount of TEM-1 in a biological sample, such as blood or serum; for diagnosing TEM-1-expressing cancer; determining a method of treating a subject afflicted with cancer; or monitoring the progression of cancer in a subject. In some embodiments, TEM-1-expressing cancer may be melanoma, sarcoma, bladder cancer, gastric cancer, hepatocellular cancer, or colon cancer. The described methods may be carried out before the subject receives treatment for TEM-1-expressing cancer, such as treatment with MORAb-004. Furthermore, the described methods may be carried out after the subject receives treatment for TEM-1-expressing cancer, such as treatment with MORAb-004. In this regard, the methods described herein may be carried out using one or more antibodies, or an antigen-binding fragment thereof, that does not compete with MORAb-004 for binding to TEM-1, such as antibodies 9G5 and 15F8.

The described methods of detecting TEM-1 in a biological sample include exposing the biological sample to one or more of the TEM-1-specific antibodies described herein.

The described methods of diagnosing TEM-1-expressing cancer in a subject also involve exposing the biological sample to one or more of the TEM-1-specific antibodies described herein; however, the methods also include quantifying the amount of TEM-1 present in the sample; comparing the amount of TEM-1 present in the sample to a known standard or reference sample; and determining whether the subject's TEM-1 levels fall within the levels of TEM-1 associated with cancer.

The methods for treating a subject afflicted with TEM-1-expressing cancer provided herein are similar to those for diagnosing TEM-1-expressing cancer, but differ in that the former includes the further step of administering to the subject, or prescribing, a treatment for the cancer. In some embodiments, the treatment for cancer may be a TEM-1-specific antibody, such as MORAb-004.

Also described herein are methods of monitoring TEM-1-expressing cancer in a subject. The described methods include exposing the biological sample to one or more of the TEM-1-specific antibodies described herein; quantifying the amount of TEM-1 present in the sample that is bound by the antibody, or antigen-binding fragment thereof; comparing the amount of TEM-1 present in the sample to either a known standard or reference sample or the amount of TEM-1 in a similar sample previously obtained from the subject; and determining whether the subject's TEM-1 levels are indicative of cancer progression, regression or stable disease based on the difference in the amount of TEM-1 in the compared samples.

The samples obtained, or derived from, subjects are biological samples such as urine, blood, serum, plasma, saliva, ascites, circulating cells, circulating tumor cells, cells that are not tissue associated, tissues, surgically resected tumor tissue, biopsies, fine needle aspiration samples, or histological preparations.

The described antibodies may be labeled for use with the described methods, or other methods known to those skilled in the art. For example, the antibodies described herein, or antigen-binding fragments thereof, may be labeled with a radiolabel, a fluorescent label, an epitope tag, biotin, a chromophore label, an ECL label, an enzyme, ruthenium, $^{111}$In-DOTA, $^{111}$In-diethylenetriaminepentaacetic acid (DTPA), horseradish peroxidase, alkaline phosphatase and beta-galactosidase, or poly-histidine or similar such labels known in the art.

Kits

Described herein are kits including the disclosed antibodies. The described kits may be used to carry out the methods of using the antibodies provided herein, or other methods known to those skilled in the art. In some embodiments the described kits may include the antibodies described herein and reagents for use in detecting the presence of TEM-1 in a biological sample. Accordingly, the described kits may include one or more of the antibodies, or an antigen-binding fragment(s) thereof, described herein and a vessel for containing the antibody or fragment when not in use, instructions for use of the antibody or fragment, the antibody or fragment affixed to a solid support, or detectably labeled forms of the antibody or fragment, as described herein.

DETAILED DESCRIPTION OF ILLUSTRATIVE EMBODIMENTS

Figure 1:
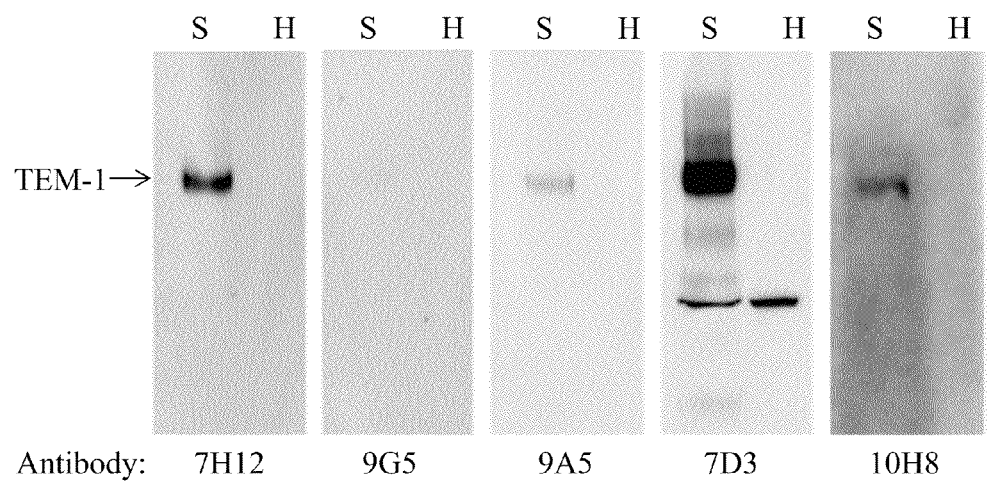
FIG. 1—Depicted are Western blots of cell lysates from either aortic smooth muscle cells (S), which are known to express TEM-1, or human umbilical vein endothelial cells (H), which do not express TEM-1. The blots were probed separately with the indicated monoclonal rat antibody specific for TEM-1.
Figure 1:
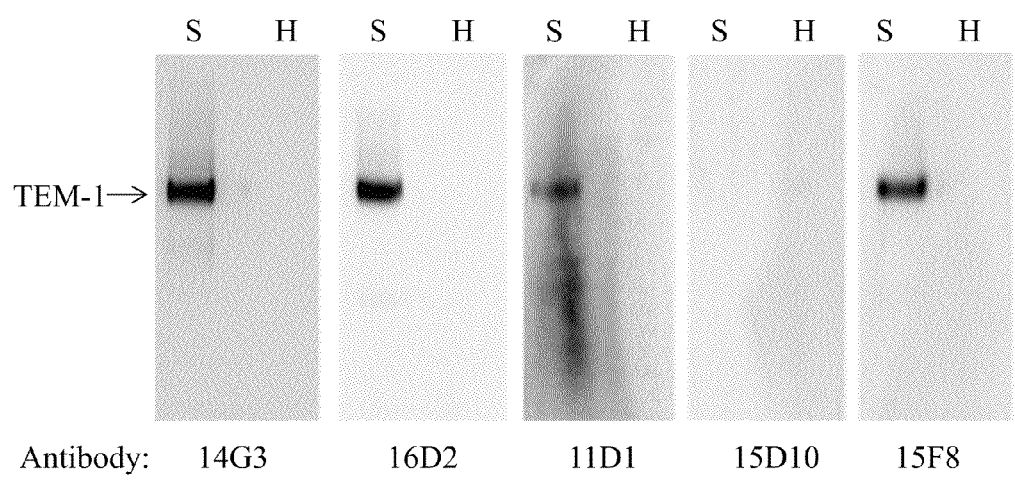

The following description characterizes antibodies, and antigen-binding fragments thereof, that specifically bind to TEM-1. Also described are related polynucleotides capable of encoding these antibodies, and antigen-binding fragments, cells expressing the antibodies, and antigen-binding fragments, as well as associated vectors and detectable antibody labels. In addition, methods of using the antibodies, and antigen-binding fragments, are described. For example, the provided antibodies, and antigen-binding fragments, may be used to detect TEM-1 in a biological sample, diagnose TEM-1-expressing cancer; monitor TEM-1-expressing cancer progression, regression, or stable disease; to determine whether or not a patient should be treated for cancer, or to determine whether or not a subject is afflicted with TEM-1-expressing cancer and thus may be amenable to treatment with a therapeutic agent directed against TEM-1. In some embodiments TEM-1-expressing cancer includes melanoma, sarcoma, bladder cancer, gastric cancer, hepatocellular cancer, or colon cancer.

DEFINITIONS

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of up to ±10% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

"Isolated" means a biological component (such as a nucleic acid, peptide or protein) has been substantially separated, produced apart from, or purified away from other biological components of the organism in which the component naturally occurs, i.e., other chromosomal and extrachromosomal DNA and RNA, and proteins. Nucleic acids, peptides and proteins that have been "isolated" thus include nucleic acids and proteins purified by standard purification methods. "Isolated" nucleic acids, peptides and proteins that can be part of a composition and still be isolated if such composition is not part of the native environment of the nucleic acid, peptide, or protein. The term also embraces nucleic acids, peptides and proteins prepared by recombinant expression in a host cell as well as chemically synthesized nucleic acids.

"Polynucleotide," synonymously referred to as "nucleic acid molecule," "nucleotides" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

The meaning of "substantially the same" can differ depending on the context in which the term is used. Because of the natural sequence variation likely to exist among heavy and light chains and the genes encoding them, one would expect to find some level of variation within the amino acid sequences or the genes encoding the antibodies or antigen-binding fragments described herein, with little or no impact on their unique binding properties (e.g., specificity and affinity). Such an expectation is due in part to the degeneracy of the genetic code, as well as to the evolutionary success of conservative amino acid sequence variations, which do not appreciably alter the nature of the encoded protein. Accordingly, in the context of nucleic acid sequences, "substantially the same" means at least 65% identity between two or more sequences. Preferably, the term refers to at least 70% identity between two or more sequences, more preferably at least 75% identity, more preferably at least 80% identity, more preferably at least 85% identity, more preferably at least 90% identity, more preferably at least 91% identity, more preferably at least 92% identity, more preferably at least 93% identity, more preferably at least 94% identity, more preferably at least 95% identity, more preferably at least 96% identity, more preferably at least 97% identity, more preferably at least 98% identity, and more preferably at least 99% or greater identity. Such identity may be determined using nBLAST algorithm (Altschul et al., (1990) Proc. Natl. Acad. Sci. USA 87:2264-8; Karlin and Altschul (1993) Proc. Natl. Acad. Sci. USA 90:5873-7).

The degree of variation that may occur within the amino acid sequence of a protein without having a substantial effect on protein function is much lower than that of a nucleic acid sequence, since the same degeneracy principles do not apply to amino acid sequences. Accordingly, in the context of an antibody or antigen-binding fragment, "substantially the same" means antibodies or antigen-binding fragments having 90%, 91%, 92%, 93%, 94%, 95%, 96%, 97%, 98%, or 99% identity to the antibodies or antigen-binding fragments described. Other embodiments include TEM-1 specific antibodies, or antigen-binding fragments, that have framework, scaffold, or other non-binding regions that do not share significant identity with the antibodies and antigen-binding fragments described herein, but do incorporate one or more CDRs or other sequences needed to confer binding that are 90%, 91%, 92%, 93%, 94%, 95%, 96%, 97%, 98%, or 99% identical to such sequences described herein.

A "vector" is a replicon, such as plasmid, phage, cosmid, or virus in which another nucleic acid segment may be operably inserted so as to bring about the replication or expression of the segment.

A "clone" is a population of cells derived from a single cell or common ancestor by mitosis. A "cell line" is a clone of a primary cell that is capable of stable growth in vitro for many generations. In some examples provided herein, cells are transformed by transfecting the cells with DNA.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression or production of an antibody or antigen-binding fragment thereof may be within the cytoplasm of the cell, or into the extracellular milieu such as the growth medium of a cell culture.

The terms "treating" or "treatment" refer to any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, neurological examination, or psychiatric evaluations.

"Antibody" refers to all isotypes of immunoglobulins (IgG, IgA, IgE, IgM, IgD, and IgY) including various monomeric, polymeric and chimeric forms, unless otherwise specified.

Antigen-binding fragments are any proteinaceous structure that may exhibit binding affinity for a particular antigen. Some antigen-binding fragments are composed of portions of intact antibodies that retain antigen-binding specificity of the parent antibody molecule. For example, antigen-binding fragments may comprise at least one variable region (either a heavy chain or light chain variable region) or one or more CDRs of an antibody known to bind a particular antigen. Examples of suitable antigen-binding fragments include, without limitation diabodies and single-chain molecules as well as Fab, F(ab')2, Fc, Fabc, and Fv molecules, single chain (Sc) antibodies, individual antibody light chains, individual antibody heavy chains, chimeric fusions between antibody chains or CDRs and other proteins, protein scaffolds, heavy chain monomers or dimers, light chain monomers or dimers, dimers consisting of one heavy and one light chain, and the like. All antibody isotypes may be used to produce antigen-binding fragments. Additionally, antigen-binding fragments may include non-antibody proteinaceous frameworks that may successfully incorporate polypeptide segments in an orientation that confers affinity for a given antigen of interest, such as protein scaffolds. Antigen-binding fragments may be recombinantly produced or produced by enzymatic or chemical cleavage of intact antibodies. The phrase "an antibody or antigen-binding fragment thereof" may be used to denote that a given antigen-binding fragment incorporates one or more amino acid segments of the antibody referred to in the phrase.

"Specific binding" when used in the context of antibodies, or antibody fragments, represents binding via domains encoded by immunoglobulin genes or fragments of immunoglobulin genes to one or more epitopes of a protein of interest, without preferentially binding other molecules in a sample containing a mixed population of molecules. Typically, an antibody binds to a cognate antigen with a $K_d$ of less than about $1 \times 10^{-8}$ M, as measured by a surface plasmon resonance assay or a cell binding assay. Phrases such as "[antigen]-specific" antibody (e.g., TEM-1-specific antibody) are meant to convey that the recited antibody specifically binds the recited antigen.

The term "subject" refers to human and non-human animals, including all vertebrates, e.g., mammals and non-mammals, such as non-human primates, mice, rabbits, sheep, dogs, cats, horses, cows, chickens, amphibians, and reptiles. In many embodiments of the described methods, the subject is a human.

The term "sample" as used herein refers to a collection of similar fluids, cells, or tissues (e.g., surgically resected tumor tissue, biopsies, including fine needle aspiration), isolated from a subject, as well as fluids, cells, or tissues present within a subject. In some embodiments the sample is a biological fluid. Biological fluids are typically liquids at physiological temperatures and may include naturally occurring fluids present in, withdrawn from, expressed or otherwise extracted from a subject or biological source. Certain biological fluids derive from particular tissues, organs or localized regions and certain other biological fluids may be more globally or systemically situated in a subject or biological source. Examples of biological fluids include blood, serum and serosal fluids, plasma, lymph, urine, saliva, cystic fluid, tear drops, feces, sputum, mucosal secretions of the secretory tissues and organs, vaginal secretions, ascites fluids such as those associated with non-solid tumors, fluids of the pleural, pericardial, peritoneal, abdominal and other body cavities, fluids collected by bronchial lavage and the like. Biological fluids may also include liquid solutions contacted with a subject or biological source, for example, cell and organ culture medium including cell or organ conditioned medium, lavage fluids and the like. The term "sample," as used herein, encompasses materials removed from a subject or materials present in a subject.

A "known standard" may be a solution having a known amount or concentration of TEM-1, where the solution may be a naturally occurring solution, such as a sample from a patient known to have early, moderate, late, progressive, or static cancer, or the solution may be a synthetic solution such as buffered water having a known amount of TEM-1 diluted therein. The known standards, described herein may include TEM-1 isolated from a subject, recombinant or purified TEM-1 protein, or a value of TEM-1 concentration associated with a disease condition.

A "reference sample" is a sample that may be compared against another sample, such as a test sample, to allow for characterization of the compared sample. The reference sample will have some characterized property that serves as the basis for comparison with the test sample. For instance, a reference sample may be used as a benchmark for TEM-1 levels that are indicative of a subject having cancer. The reference sample does not necessarily have to be analyzed in parallel with the test sample, thus in some instances the reference sample may be a numerical value or range previously determined to characterize a given condition, such as TEM-1 levels that are indicative of cancer in a subject. The term also includes samples used for comparative purposes that are known to be associated with a physiologic state or disease condition, such as TEM-1-expressing cancer, but that have an unknown amount of TEM-1.

The term "progression," as used in the context of progression of TEM-1-expressing cancer, includes the change of a cancer from a less severe to a more severe state. This may include an increase in the number or severity of tumors, the degree of metastasis, the speed with which the cancer is growing or spreading, and the like. For example, "the progression of colon cancer" includes the progression of such a cancer from a less severe to a more severe state, such as the progression from stage I to stage II, from stage II to stage III, etc.

The term "regression," as used in the context of regression of TEM-1-expressing cancer, includes the change of a cancer from a more severe to a less severe state. This could include a decrease in the number or severity of tumors, the degree of metastasis, the speed with which the cancer is growing or spreading, and the like. For example, "the regression of colon cancer" includes the regression of such a cancer from a more severe to a less severe state, such as the progression from stage III to stage II, from stage II to stage I, etc.

The term "stable" as used in the context of stable TEM-1-expressing cancer, is intended to describe a disease condition that is not, or has not, changed significantly enough over a clinically relevant period of time to be considered a progressing cancer or a regressing cancer.

The terms "colon cancer" and "colorectal cancer" are used interchangeably herein.

The embodiments described herein are not limited to particular methods, reagents, compounds, compositions or biological systems, which can, of course, vary.

TEM-1-Specific Antibodies and Antigen-Binding Fragments

Described herein are isolated monoclonal antibodies or antigen-binding fragments that specifically bind TEM-1. The general structure of an antibody molecule comprises an antigen binding domain, which includes heavy and light chains, and the Fc domain, which serves a variety of functions, including complement fixation and binding antibody receptors.

The described antibodies or antigen-binding fragments include all isotypes, IgA, IgD, IgE, IgG and IgM, and synthetic multimers of the four-chain immunoglobulin structure. The described antibodies or antigen-binding fragments also include the IgY isotype generally found in hen or turkey serum and hen or turkey egg yolk.

The antibodies or antigen-binding fragments disclosed in the examples section are derived from rats. Similar antibodies may be derived from any species by recombinant means. For example, the antibodies or antigen-binding fragments may be mouse, goat, horse, swine, bovine, chicken, rabbit, camelid, donkey, human, or chimeric versions thereof. For use in administration to humans, non-human derived antibodies or antigen-binding fragments may be genetically or structurally altered to be less antigenic upon administration to a human patient.

In some embodiments, the antibodies or antigen-binding fragments are chimeric. As used herein, the term "chimeric" refers to an antibody, or antigen-binding fragment thereof, having at least some portion of at least one variable domain derived from the antibody amino acid sequence of a non-human mammal, a rodent, or a reptile, while the remaining portions of the antibody, or antigen-binding fragment thereof, are derived from a human. For example, a chimeric antibody may comprise a rat antigen binding domain with a human Fc or other such structural domain.

In some embodiments, the antibodies are humanized antibodies. Humanized antibodies may be chimeric immunoglobulins, immunoglobulin chains or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin sequence. The humanized antibody may include at least a portion of an immunoglobulin constant region (Fc), typically that of a human immunoglobulin.

The antibodies or antigen-binding fragments described herein can occur in a variety of forms, but will include one or more of the antibody variable domain segments or CDRs shown in Table 2. The isotypes of the antibodies described in Table 2 are shown in parentheses to describe the constant region of each antibody, which are known to have conserved sequences. DNA sequences corresponding to the amino acid sequences in Table 2 are provided in Table 3.

TABLE 2

Antibody segments of the described antibodies and antigen-binding fragments thereof ("Lc" denotes light chain, "Hc" denotes heavy chain, "VLc" denotes light chain variable domain, and "VHc" denotes heavy chain variable domain).

| Antibody Segment | SEQ ID NO: | Amino Acid Sequence |
|---|---|---|
| Antibody 7D3 (IgG2a/κ) | | |
| Lc CDR 1 | 1 | QSLLDSDGNTY |
| Lc CDR 2 | 2 | LVS |
| Lc CDR 3 | 3 | MQATHAPFT |
| VLc | 4 | MSPVQSLFLLLLWILGTKGDVVLTQTPSILSATIGQSVSISCRSSQSLLDS DGNTYLYWFLQRPGQSPQRLIYLVSNLGSGVPNRFSGSGSGTDFTLKISG VEAGDLGVYYCMQATHAPFTFGSGTKLEIK |
| Hc CDR 1 | 5 | GFDFKTYA |
| Hc CDR 2 | 6 | ISTKGHNYAT |
| Hc CDR 3 | 7 | TVAGYNFDY |
| VHc | 8 | MVLLELVSVIALFQGVHCEVQLVESGGGLVQPKGSLKLSCAASGFDFKT YAMSWVRQAPGKGLDWIVTISTKGHNYATLYADSVKERFTISRDDSQS MVYLQMNNLKTEDTALYYCTVAGYNFDYWGQGVMVTVSS |
| Antibody 7H12 (IgG1/κ) | | |
| Lc CDR 1 | 9 | QSVGIN |
| Lc CDR 2 | 10 | TAS |
| Lc CDR 3 | 11 | LQYGSLPFT |

TABLE 2-continued

Antibody segments of the described antibodies and antigen-binding fragments thereof ("Lc" denotes light chain, "Hc" denotes heavy chain, "VLc" denotes light chain variable domain, and "VHc" denotes heavy chain variable domain).

| Antibody Segment | SEQ ID NO: | Amino Acid Sequence |
|---|---|---|
| VLc | 12 | MESHTRVFIFLLLWLSGGDGETVMTQSPTSMPTSIGERVTLNCKASQSVGINVDWYQQTPGQSPLLIYTASNRHTGVPDRFAGSGSGRDFTLTISNVEAEDLVVYYCLQYGSLPFTFGAGTKLELK |
| Hc CDR 1 | 13 | GFTFSNFD |
| Hc CDR 2 | 14 | ITYDGSRT |
| Hc CDR 3 | 15 | ARHGSSYYWFFDF |
| VHc | 16 | MDIRLSLAFLVLFIKDVQCEVQLVESGGGLVQPGRSMILSCAASGFTFSNFDMAWVRQAPKMGLEWVATITYDGSRTNYRDSVKGRFTISRDSAKNTLYLQMDSLTSEDTATYYCARHGSSYYWFFDFWGPGTMVTVSS |

Antibody 9A5 (IgG2a/κ)

| | | |
|---|---|---|
| Lc CDR 1 | 17 | HSVGTN |
| Lc CDR 2 | 18 | DAS |
| Lc CDR 3 | 19 | QQTQSWPLT |
| VLc | 20 | MVFKFQILGLLLLFWISASRGDIVLTQSPTTLSVTPGETVSLSCRASHSVGTNLHWYQQKTNESPRLLIKDASQSMSGIPSRFSASGSGTDFTLNIKNVEFDDVSSYFCQQTQSWPLTFGSGTKLEIK |
| Hc CDR 1 | 21 | GFTFRNYY |
| Hc CDR 2 | 22 | TGSGGDFT |
| Hc CDR 3 | 23 | ARAYGYFDY |
| VHc | 24 | MDIRLSLAFLVLFIEDVQCEVQLVESGGGLVQPGRSMKLSCAASGFTFRNYYMAWVRQAPTRGLEWVASTGSGGDFTYYRDSVKGRFTISRDTAENTLYLQMDSLRSEDTATYYCARAYGYFDYWGQGVRVTVSS |

Antibody 10H8 (IgG2a/κ)

| | | |
|---|---|---|
| Lc CDR 1 | 25 | QSLLYNENNKNY |
| Lc CDR 2 | 26 | WAS |
| Lc CDR 3 | 27 | QQYFRFPRT |
| VLc | 28 | MESQTQVLMSLLLWVAGSCGDIVMTQTPSSQAVSAGEKVTMSCTSGQSLLYNENNKNYLAWYQLKPGQSPRLLIYWASTRESGVPDRFIGSGSGTYFTLTISSVQAEDLAVYYCQQYFRFPRTFGGGTKLELK |
| Hc CDR 1 | 29 | GFSLTNYN |
| Hc CDR 2 | 30 | IWSGGSA |
| Hc CDR 3 | 31 | TRDQLGGWYFDF |
| VHc | 32 | MAVLGLLLCLVTFPSCALSQVQLKESGPGLVQPSQTLSLTCTVSGFSLTNYNIHWVRQPPGKGLEWMGAIWSGGSADYDSALKSRLSISRDTSKSQVFLKMDNLQTEDTAIYYCTRDQLGGWYFDFWGPGTKVTVSS |

Antibody 11D1 (IgG2a/κ)

| | | |
|---|---|---|
| Lc CDR 1 | 33 | KSLLSIEGINS |
| Lc CDR 2 | 34 | RMS |
| Lc CDR 3 | 35 | AQFLEFPFT |
| VLc | 36 | MKFPAQFLGLMVLCFPGATGDNVLTQAPLAVSVTPGESASISCRSSKSLLSIEGINSLYWYLQKPGKSPQLLLFRMSNLASGVPDRFSGSGSETDFTLKISQVETEDVGVYYCAQFLEFPFTFGSGTKLEIK |
| Hc CDR 1 | 37 | GFSFSDYY |
| Hc CDR 2 | 38 | ISYDGSGS |
| Hc CDR 3 | 39 | ARGGGLDY |
| VHc | 40 | MDIRLSLVFLVLFIKGVQCEVQLVESDGGLVQPGRSLKLSCAASGFSFSDYYMAWVRQAPTKGLEWVATISYDGSGSYYRDSVKGRFTVSRDNAKTTLYLQMDSLRSEDTATYYCARGGGLDYWGQGVMVTVSS |

Antibody 14G3 (IgG2a/κ)

| | | |
|---|---|---|
| Lc CDR 1 | 41 | QSLLYNKNKKNY |
| Lc CDR 2 | 42 | WAS |
| Lc CDR 3 | 43 | QQYYTFPT |
| VLc | 44 | MESQTQVLMSLLLWVSGTCGDIVMTQTPSSQAVSAGAKVTLSCKSSQSLLYNKNKKNYLAWYQQKPGQSPKLLIYWASTRESGVPDRFIGSGSGTDFTLTISSVQAEDLAIYYCQQYYTFPTFGAGTKLELK |
| Hc CDR 1 | 45 | GFTFSDYN |
| Hc CDR 2 | 46 | ISYNGSEI |
| Hc CDR 3 | 47 | ARHWREYYSSYSSYVMDA |
| VHc | 48 | MDIRLSLVFLVLFMKGVQCEVQLVEFGGGLVQPGRSLKLSCAASGFTFSDYNLAWVRQAPKKGLEWVATISYNGSEIYYRDSVKGRFTISRDNAKNTLYLQMDSLRSEDTATYYCARHWREYYSSYSSYVMDAWGQGASVTVSS |

TABLE 2-continued

Antibody segments of the described antibodies and antigen-binding fragments thereof ("Lc" denotes light chain, "Hc" denotes heavy chain, "VLc" denotes light chain variable domain, and "VHc" denotes heavy chain variable domain).

| Antibody Segment | SEQ ID NO: | Amino Acid Sequence |
|---|---|---|
| \multicolumn{3}{c}{Antibody 15D10 (IgG2a/κ)} |

Antibody 15D10 (IgG2a/κ)

| Antibody Segment | SEQ ID NO: | Amino Acid Sequence |
|---|---|---|
| Lc CDR 1 | 49 | KSLLGSKGINF |
| Lc CDR 2 | 50 | RMS |
| Lc CDR 3 | 51 | AQFLEYPNS |
| VLc | 52 | MKFPAQFLGLIVLCIPGATGDIVLTQAPLSVSVTPGESASISCRSSKSLLGSKGINFLYWYLQKPGKSPQLLIYRMSNLASGVPDRFSGSGSETDFILKISKVETEDVGVYYCAQFLEYPNSFGAGTKLELK |
| Hc CDR 1 | 53 | GFSLTNYN |
| Hc CDR 2 | 54 | MWSGGNT |
| Hc CDR 3 | 55 | ARDSGYGEGRLDY |
| VHc | 56 | MAVRVLLLCLVTFPTCALSQVQLMESGPGLVQPSETLSLTCTVSGFSLTNYNIHWVRQPPGKGLEWMGLMWSGGNTDYNSALKSRLTISRDTSKNQVFLKMNSLQSEDTTTYYCARDSGYGEGRLDYWGQGVMVTVSS |

Antibody 15F8 (IgG2a/κ)

| Antibody Segment | SEQ ID NO: | Amino Acid Sequence |
|---|---|---|
| Lc CDR 1 | 57 | HSVGTN |
| Lc CDR 2 | 58 | YVS |
| Lc CDR 3 | 59 | QQTQSWPLT |
| VLc | 60 | MVFKFQILGLLLFWISASRGDIVLTQSPTTLSVTPGETVSLSCRASHSVGTNLHWYQQKPNESPRLLIKYVSQSNSGIPSRFSASGSGTDFTLNIKNVEFNDVSSYFCQQTQSWPLTFGAGTKLEIK |
| Hc CDR 1 | 61 | GFTFRNYY |
| Hc CDR 2 | 62 | TGTGGDFT |
| Hc CDR 3 | 63 | ARAYGYFDY |
| VHc | 64 | MDIRLSLAFLVLFIKGVQCEVQLVESGGGLVQPGRSMKLSCSASGFTFRNYYMAWVRQAPTRGLEWVASTGTGGDFTYYRDSVKGRFTISRDTAENTLYLQMDSLRSEDTATYYCARAYGYFDYWGQGVKVTVSS |

Antibody16D2 (IgG2a/κ)

| Antibody Segment | SEQ ID NO: | Amino Acid Sequence |
|---|---|---|
| Lc CDR 1 | 65 | HSVGTN |
| Lc CDR 2 | 66 | YVS |
| Lc CDR 3 | 67 | QQTQSWPLT |
| VLc | 68 | MVFKFQILGLLLFWISASRGDIVLTQSPTTLSVTPGETVSLSCRASHSVGTNLHWYQQKTNESPRLLIKYVSQSNSGIPSRFSASGSGTDFTLNIKDVEFDDVSSYFCQQTQSWPLTFGSGTKLEIK |
| Hc CDR 1 | 69 | GFIFRNYY |
| Hc CDR 2 | 70 | TGTGGDFT |
| Hc CDR 3 | 71 | ARAYGYFDY |
| VHc | 72 | MDIRLSLAFLVLFIKGVQCEVQLVESGGGLVQPGRSMKLSCSASGFIFRNYYMAWVRQAPTKGLEWVASTGTGGDFTYYRDSVKGRFTISRDTAESTLYLQMDSLKSEDTATYYCARAYGYFDYWGQGVKVTVSS |

Antibody 9G5 (IgG1/κ)

| Antibody Segment | SEQ ID NO: | Amino Acid Sequence |
|---|---|---|
| Lc CDR 1 | 73 | QNIYKY |
| Lc CDR 2 | 74 | NIN |
| Lc CDR 3 | 75 | YQYNSGRA |
| VLc | 76 | MAPVQLLGLLLLCLRAMRCDIQMTQSPSLLASEGDRVTLSCKASQNIYKYLNWYQQKLGEAPKLLIYNINNLQTGIPSRFSGSGSGTDFTLTISSLQPEDVATYYCYQYNSGRAFGGGTKLELK |
| Hc CDR 1 | 77 | GFTFSDYW |
| Hc CDR 2 | 78 | IRNKLNNYVT |
| Hc CDR 3 | 79 | TRIQRVITTGEYFDY |
| VHc | 80 | MDLRLTYVFIVAILKGVLCEVKLEESGGGLVQPGMSVKLSCATSGFTFSDYWMEWVRQAPGKGLEWVAEIRNKLNNYVTNYGKPVRGRFTISRDDSKSIVYLQVNSIRSEDTGIYYCTRIQRVITTGEYFDYWGQGVMVTVSS |

TABLE 3

DNA sequences encoding the antibody segments of the described antibodies and antigen-binding fragments thereof ("Lc" denotes light chain, "Hc" denotes heavy chain, "VLc" denotes light chain variable domain, and "VHc" denotes heavy chain variable domain).

| Antibody Segment | SEQ ID NO: | Nucleic Acid Sequence |
|---|---|---|
| Antibody 7D3 | | |
| Lc CDR 1 | 81 | cagagtctcttagatagtgatggaaacacctat |
| Lc CDR 2 | 82 | ttggtatcc |
| Lc CDR 3 | 83 | atgcaagctacccatgctccattcacg |
| VLc | 84 | atgagtcctgtccagtccctgttttattattgctttggattctgggaaccaaaggtgatgttgtgctgacccagactccatccatattgtctgctaccattggacaatcggtctccatctcttgcaggtcaagtcagagtctcttagatagtgatggaaacacctatttatattggttcctacagaggccaggccagtctccacagcgtctaatttatttggtatccaacctgggatctggggtccccaacaggttcagtggcagtgggtcaggaacagatttcacactcaaaatcagtggggtggaggctggagatttgggagtttattactgcatgcaagctacccatgctccattcacgttcggctcagggacgaagttggaaataaaa |
| Hc CDR 1 | 85 | ggatttgacttcaaaacttatgcc |
| Hc CDR 2 | 86 | ataagcactaagggtcataattatgcaaca |
| Hc CDR 3 | 87 | actgtggcagggtataattttgattac |
| VHc | 88 | atggttctcctggagttggtttccgtgattgctcttttcaaggcgtgcattgtgaggtgcagcttgttgagtctggtggagggcttggtgcagcctaaagggtcattgaaactctcatgtgcagcctctggatttgacttcaaaacttatgccatgagctgggtccgccaggctccaggaaagggtctggattggattgttaccataagcactaagggtcataattatgcaacactttatgctgactcagtgaaagagagattcaccatctccagagatgattcacaaagcatggtttacttgcaaatgaacaacttgaaaactgaggacacagccttgtattactgtactgtggcagggtataattttgattactggggccaaggagtcatggtcacagtctcctca |
| Antibody 7H12 | | |
| Lc CDR 1 | 89 | cagagcgtgggtattaat |
| Lc CDR 2 | 90 | acggcatcc |
| Lc CDR 3 | 91 | ctgcaaatatggctcccttccgttcacg |
| VLc | 92 | atggagtcacatactagggtcttcatattcctgctgctctggttgtctggaggtgatggggaaactgtgatgacccagtctcccacatccatgcccacatcaataggagagagggtcaccctgaactgcaaggccagtcagagcgtgggtattaatgtagactggtaccaacagacaccagggcagtctccgaaactgctgatatatacggcatccaaccggcacactgggtccctgatcgcttcgcaggcagtgggtctgggagagatttcactctcaccatcagcaacgtggaggctgaagaccggttgttttattactgtctgcaaatatggctcccttccgttcacgtttggagctgggaccaagctggagctgaaa |
| Hc CDR 1 | 93 | ggattcactttcagtaactttgac |
| Hc CDR 2 | 94 | attactatgatggcagtagaact |
| Hc CDR 3 | 95 | gcaagacatggaagctcctactactggttctttgacttc |
| VHc | 96 | atggacatcaggctcagtctggctttccttgtcctttttcataaaagatgtccagtgtgaggtgcagctggtggagtctggggaggcttggtgcagcctggaaggtccatgatactctcctgtgcagcctcaggattcactttcagtaactttgacatggcctgggtccgccaggctccaaagatgggtctggagtgggtcgcaaccattactatgatggcagtagaactaactatcgagactccgtgaagggccgattcactatctccagagatagtgcaaagaacaccctatacctgcaaatggacagtctgacgtctgaggacacggccacttattactgtgcaagacatggaagctcctactactggttctttgacttctggggcccaggaaccatggtcaccgtgtcctca |
| Antibody 9A5 | | |
| Lc CDR 1 | 97 | catagtgttggcacaaat |
| Lc CDR 2 | 98 | gatgcctca |
| Lc CDR 3 | 99 | caacagactcaaagttggcccctcacg |
| VLc | 100 | atggtgttcaaatttcagatccttggacttctgcttttctggatttcagcctctagaggggacatcgtgttgactcagtctccaaccaccctgtctgtgactccaggagagacagtcagtctttcctgcagggctagtcatagtgttggcacaaatctcacactggtatcagcaaaaacaaatgagtccccaaggcttctcatcaaggatgcctcacagtccatgtccgggatccctccaggttcagtgccagtggatcagggacagattttactctcaacatcaaaaatgtggagtttgatgatgtctcgagtatttttgtcaacagactcaaagttggcccctcacgttcggttctgggaccaagctggagatcaaa |
| Hc CDR 1 | 101 | ggattcactttcagaaactattac |
| Hc CDR 2 | 102 | actggtagtggtggtgatttcact |
| Hc CDR 3 | 103 | gcaagggcctatggatactttgattac |
| VHc | 104 | atggacatcaggctcagtttggctttccttgtcctttttcatagaagatgtccagtgtgaggtgcagctggtggagtctggggaggcctagtgcagcctggaaggtccatgaaactctcctgtgcagcctcaggattcactttcagaaactattacatggcctgggtccgccaggctccaacgagggtctggagtgggtcgcatccactggtagtggtggtgatttcacttactatcgagactccgtgaagggccgattcactatctccagagatactgcagaaaacacccctatacctacaaatggacagtctgaggtctgaggacacggccacgtattactgtgcaagggcctatggatactttgattactggggccaaggagtcagggtcacagtctcctca |
| Antibody 10H8 | | |
| Lc CDR 1 | 105 | cagagtcttttatacaatgaaaacaataagaactac |
| Lc CDR 2 | 106 | tgggcatcc |
| Lc CDR 3 | 107 | cagcaatattttaggtttcctcggacg |
| VLc | 108 | atggaatcacagacacaggtcctcatgtccctgctgctctgggtagctggttcctgtggggacattgtgatgacccagactccatcctcccaggctgtgtcagcagggagaaggtcactatgagctgcacgtccggtcagagtcttttatacaatgaaaacaataagaactacttggcctggtaccagcagtgaaaccggggcagtctcctagactgctgatctactgggcatccactagggaatctggggtccctgatcgcttcataggcagtggatctgggacgtatttcactctgaccatcagcagtgtgcaggcagaagacctggctgtttattactgccagcaatattttaggtttcctcggacgttcggtggaggcaccaagctggaattgaaa |

TABLE 3-continued

DNA sequences encoding the antibody segments of the described antibodies and antigen-binding fragments thereof ("Lc" denotes light chain, "Hc" denotes heavy chain, "VLc" denotes light chain variable domain, and "VHc" denotes heavy chain variable domain).

| Antibody Segment | SEQ ID NO: | Nucleic Acid Sequence |
|---|---|---|
| Hc CDR 1 | 109 | ggattctcactaaccaactataat |
| Hc CDR 2 | 110 | atttggagtggtggaagtgca |
| Hc CDR 3 | 111 | accagagatcaactggggaggctggtactttgacttc |
| VHc | 112 | atggctgtcctggggctgttgctctgcctggtgacatttccaagctgtgccctgtcccaggtgcagctgaaggagtc aggacctggtctggtgcagccctcacagaccctgtccctcacctgcactgtctctggattctcactaaccaactata atatacactgggttcgacagcctccaggaaagggtctggagtggatgggagcaatttggagtggtggaagtgca gattatgattcagctctcaaatcccgactgagcatcagcagggacacctccaagagccaagtttcttgaaaatgga caatctgcaaactgaagacacagccatttactactgtaccagagatcaactggggaggctggtactttgacttctggg gcccaggaaccaaggtcaccgtgtcctca |

Antibody 11D1

| Lc CDR 1 | 113 | aagagtctgctaagtattgagggcattaattcc |
| Lc CDR 2 | 114 | cggatgtcc |
| Lc CDR 3 | 115 | gcacagtttctagaatttccattcacg |
| VLc | 116 | atgaagtttcctgctcagtttcttggactgatggtgctctgttttcctggagccactggggataatgtgttgactcaagc tccactcgctgtttctgtcactcctggagagtcagcttccatctccctgcaggtctagtaagagtctgctaagtattgag ggcattaattccttgtattggtaccttcagaagccaggaaagtctcctcagctcctgcttttcggatgtccaaccttgc ctcaggagttccagacaggtttagtggcagtgggtcagaaacagattttacactgaaaatcagtcaggtggagact gaggatgttggcgtttattactgtgcacagtttctagaatttccattcacgttcggctcagggacgaagttggaaataa aa |
| Hc CDR 1 | 117 | ggattcagtttcagtgactattac |
| Hc CDR 2 | 118 | attagttatgatggtagtggtagt |
| Hc CDR 3 | 119 | gcaagagggggtggtcttgattac |
| VHc | 120 | atggacatcaggctcagcttggttttccttgtcctttttcataaaaggtgtccagtgtgaggtgcagctggtggagtctg atggaggcttagtgcagcctggaaggtccctaaaactctcctgtgcagcctcaggattcagtttcagtgactattaca tggcctgggtccgccaggctccaacgaaggggctggagtgggtcgcaaccattagttatgatggtagtggtagtt actatcgagactccgtgaagggccgattcactgtctccagagataatgcaaaaaccaccctatacctgcaaatggaa cagtctgaggtctgaggacacggccacttattactgtgcaagagggggtggtcttgattactggggccaaggagt catggtcacagtctcctca |

Antibody 14G3

| Lc CDR 1 | 121 | cagagtcttttatacaataaaaacaaaaagaactac |
| Lc CDR 2 | 122 | tgggcatcc |
| Lc CDR 3 | 123 | cagcagtactataccttttcccacc |
| VLc | 124 | atggaatcacagacacaggtcctcatgtccctgctgctctgggtatctggtacctgtggggacattgtgatgaccca gactccatcctcccaggctgctgtcagcaggggccaaggtcaatttgagctgcaagtccagtcagagtcttttataca ataaaaacaaaaagaactacttggcctggtaccagcagaaaccagggcagtctcctaaactgctgatctactggg catccactagggaatctggggtccctgatcgcttcataggcagtggatctgggacagatttcactctgaccatcagc agtgtgcaggcagaagacctggctattttattactgccagcagtactataccttttcccaccttttggggctgggaccaa gctgaactgaaa |
| Hc CDR 1 | 125 | ggattcactttcagtgactataat |
| Hc CDR 2 | 126 | attagttataatggtagtgaaatt |
| Hc CDR 3 | 127 | gcaagacattggcgggaatactatagcagttattcctcctatgttatggatgcc |
| VHc | 128 | atggacatcaggctcagcttggttttccttgtccttttttatgaaaggtgtccagtgtgaggtgcagctggtggagtttg ggggaggcttagtgcagcctggaaggtccctgaaactctcctgtgcagcctcaggattcactttcagtgactataat ttggcctgggtccgccaggctccaaagaagggtctggagtgggtcgcaaccattagttataatggtagtgaaattta ctatcgagactccgtgaagggccgattcaccatctccagagataatgcaaaaaacacccctatatctgcagatggac agtctgaggtctgaggacacggccacttattactgtgcaagacattggcgggaatactatagcagttattcctcctat gttatggatgcctggggtcaaggagcttcagtcactgtctcctca |

Antibody 15D10

| Lc CDR 1 | 129 | aagagtcttctaggtagtaagggcatcaatttc |
| Lc CDR 2 | 130 | cggatgtcc |
| Lc CDR 3 | 131 | gcacagtttctagaatatccgaactcg |
| VLc | 132 | atgaagtttcctgctcagtttcttggactgatagtgctctgtattcctggagccactggggatattgtgttgactcaagc tccactctctgtttctgtcactcctggagagtcagcttccatctgcaggtctagtaagagtcttctaggtagtaagg gcatcaatttcttgtattggtaccttcagaagccaggaaagtctcctcagctcctgatatcggatgtccaaccttgc ctcaggagttccagacaggtttagtggcagtgggtcagaaacagattttatactgaagatcagtaaggtggagactg aggatgttggcgtttattactgtgcacagtttctagaatatccgaactcgtttggagctgggaccaagttggaactga aa |
| Hc CDR 1 | 133 | gggttctcgctaaccaactataac |
| Hc CDR 2 | 134 | atgtggagtggtggaaacaca |
| Hc CDR 3 | 135 | gccagagattctggttacgagagggtcgtcttgattac |
| VHc | 136 | atggctgtccgggtactgttgctctgcctggtgacatttccaacctgtgccctgtcccaggtgcagctgatggagtc aggacctggcctggtgcagccctcagagaccctgtccctcacctgcactgtctctgggttctcgctaaccaactata acattcactgggttcgacagcctccagggaaaggtctggagtggatgggactaatgtggagtggtggaaacaca gattataattcagctctcaaatcccgactgaccatcagcagggacacctccaagaaccaagtttcttaaaaatgaa cagtctgcaaagtgaagacacaaccacttactactgtgccagagattctggttacgagagggtcgtcttgattact ggggccaaggcgtcatggtcacagtctcctca |

TABLE 3-continued

DNA sequences encoding the antibody segments of the described antibodies and antigen-binding fragments thereof ("Lc" denotes light chain, "Hc" denotes heavy chain, "VLc" denotes light chain variable domain, and "VHc" denotes heavy chain variable domain).

| Antibody Segment | SEQ ID NO: | Nucleic Acid Sequence |
|---|---|---|
| Antibody 15F8 | | |
| Lc CDR 1 | 137 | catagtgttggcacaaat |
| Lc CDR 2 | 138 | tatgtctca |
| Lc CDR 3 | 139 | caacagactcaaagttggcccctcacg |
| VLc | 140 | atggtgttcaaatttcagatccttggacttctgcttttctggatttcagcctctagagggacatcgtgctgactcagtct ccaaccaccctgtctgtgactccaggagagacagtcagtctttcctgcagggctagccatagtgttggcacaaatct acactggtatcagcaaaaaccaaatgagtctccaaggctatgtctccacagtccaattccgggatcc cctccaggttcagtgccagtggatcagggacagattttactctcaacatcaaaaatgtggaatttaatgatgtctcaa gttatttttgtcaacagactcaaagttggcccctcacgttcggtgctgggaccaagctggagatcaaa |
| Hc CDR 1 | 141 | ggattcactttcagaaattattac |
| Hc CDR 2 | 142 | actggtactggtggtgatttcact |
| Hc CDR 3 | 143 | gcaagggcctatgggtactttgattac |
| VHc | 144 | atggacatcaggctcagtttggctttccttgtccttttcataaaaggtgtccagtgtgaggtgcagctggtggagtctg ggggaggcttagtgcagcctggaaggtccatgaaactctcctgttcagcctcaggattcactttcagaaattattaca tggcctgggtccgccaggctccaacgaagggtctggagtgggtcgcatccactggtactggtggtgatttcactta ctatcgagactccgtgaagggccgattcactatctccagagatactgcagaaaacaccctatacttacaaatggac agtctgaggtctgaggacacggccacttattactgtgcaagggcctatgggtactttgattactggggccaaggag tcaaggtcacagtctcctca |
| Antibody 16D2 | | |
| Lc CDR 1 | 145 | catagtgttggcacaaat |
| Lc CDR 2 | 146 | tatgtctca |
| Lc CDR 3 | 147 | caacagactcaaagttggcccctcacg |
| VLc | 148 | atggtgttcaaatttcagatccttggacttctgcttttctggatttcagcctctagagggacatcgtgctgactcagtct ccaaccaccctgtctgtgactccaggagagacagtcagtctttcctgcagggctagccatagtgttggcacaaatct acactggtatcagcaaaaaacaaatgagtctccaaggcttctcatcaagtatgtctcacagtccaattccgggatcc cctccaggttcagtgccagtggatcagggacagattttactctcaacatcaaagatgtggagtttgatgatgtctcaa gttatttttgtcaacagactcaaagttggcccctcacgttcggttctgggaccaagctggagatcaaa |
| Hc CDR 1 | 149 | ggattcattttcagaaactattac |
| Hc CDR 2 | 150 | actggtactggtggtgatttcact |
| Hc CDR 3 | 151 | gcaagggcctatgggtactttgattac |
| VHc | 152 | atggacatcaggctcagtttggctttccttgtccttttcataaaaggtgtccagtgtgaggtgcagctggtggagtctg ggggaggcttagtgcagcctggaaggtccatgaaactctcctgttcagcctcaggattcattttcagaaactattaca tggcctgggtccgccaggctccaacgaagggtctggagtgggtcgcatccactggtactggtggtgatttcactta ctatcgagactccgtgaagggccgattcactatctccagagatactgcagaaagcacctatacttacaaatggac agtctgaagtctgaggacacggccacttattactgtgcaagggcctatgggtactttgattactggggccaaggagt caaggtcacagtctcctca |
| Antibody 9G5 | | |
| Lc CDR 1 | 153 | cagaatatctacaagtac |
| Lc CDR 2 | 154 | aatataaat |
| Lc CDR 3 | 155 | tatcagtataacagtgggcgggcg |
| VLc | 156 | atggctccagtacaacttctagggcttttgctgctctgcctccgagccatgagatgtgacatccagatgacccagtct ccttcactcctgtcagcatctgagggagacagagtcactctcagctgcaaagcaagtcagaatatctacaagtactt aaaactggtatcagcaaaagcttggagaagctcccaaactcctgatatataatataaatatttgcaaacgggcatcc catcaaggttcagtggcagtggatctggtacagatttcacacttaccatcagcagcctgcagcctgaagacgttgc cacatattactgctatcagtataacagtgggcgggcgttcggaggaggcaccaagctggaattgaaa |
| Hc CDR 1 | 157 | ggattcactttcagtgactactgg |
| Hc CDR 2 | 158 | attagaaataaacttaataattatgtaaca |
| Hc CDR 3 | 159 | acaaggatacaacgggttattactacgggggaatactttgattac |
| VHc | 160 | atggacttgcgactgacttatgtctttattgttgctattttaaaaggtgtcttgtgtgaggtgaaactggaggaatctgg ggagggtttggtgcaacctggaatgtccgtgaaactctcttgtgcaacctctggattcactttcagtgactactggat ggagtgggtccgccaggctccagggaaggggctagaatgggtagctgaaattagaaataaacttaataattatgt aacaaattatgggaagcctgtgagaggcagattcaccatctcaagagatgattccaaaagtatagtctacctgcag gtgaacagcataagatctgaagatactggtatttattactgtacaaggatacaacgggttattactacgggggaatac tttgattactggggccaagggctcatggtcacagtctcctca |

Described herein are isolated antibodies and antigen-binding fragments that specifically bind to TEM-1. In some embodiments, the antibodies or antigen-binding fragments are rat IgG, or derivatives thereof. While the antibodies or antigen-binding fragments may be human, humanized, or chimeric, the antibodies or antigen-binding fragments exemplified herein are derived from rats. In some embodiments, antibodies or antigen-binding fragments may include a light chain CDR1 amino acid sequence substantially the same as, or identical to, SEQ ID NO: 1. In some embodiments, antibodies or antigen-binding fragments may include a light chain CDR2 amino acid sequence substantially the same as, or identical to, SEQ ID NO: 2. In some embodiments, antibodies or antigen-binding fragments may include a light chain CDR3 amino acid sequence substantially the same as, or identical to, SEQ ID NO: 3. In some embodiments, antibodies or antigen-binding fragments may include a heavy chain CDR1 amino acid sequence substantially the same as, or identical to, SEQ ID NO: 5. In some embodiments, antibodies or antigen-binding fragments may include a heavy chain CDR2 amino acid sequence substantially the same as, or identical to, SEQ ID NO: 6. In some embodiments, antibodies or antigen-binding fragments may include a heavy chain CDR3 amino acid sequence substantially the same as, or identical to, SEQ ID NO: 7. The antibodies or antigen-binding fragments may include a light chain having a CDR1 amino acid sequence substantially the same as, or identical to, SEQ ID NO: 1; a CDR2 amino acid sequence substantially the same as, or identical to, SEQ ID NO: 2; and a CDR3 amino acid sequence substantially the same as, or identical to, SEQ ID NO: 3. The antibodies or antigen-binding fragments may include a heavy chain having a CDR1 amino acid sequence substantially the same as, or identical to, SEQ ID NO: 5; a CDR2 amino acid sequence substantially the same as, or identical to, SEQ ID NO: 6; and a CDR3 amino acid sequence substantially the same as, or identical to, SEQ ID NO: 7. The antibodies or antigen-binding fragments may include a light chain having a CDR1 amino acid sequence substantially the same as, or identical to, SEQ ID NO: 1; a CDR2 amino acid sequence substantially the same as, or identical to, SEQ ID NO: 2; and a CDR3 amino acid sequence substantially the same as, or identical to, SEQ ID NO: 3, and also have a heavy chain having a CDR1 amino acid sequence substantially the same as, or identical to, SEQ ID NO: 5; a CDR2 amino acid sequence substantially the same as, or identical to, SEQ ID NO: 6; and a CDR3 amino acid sequence substantially the same as, or identical to, SEQ ID NO: 7.

The described antibodies or antigen-binding fragments may include a light chain variable domain that includes an amino acid sequence substantially the same as, or identical to, SEQ ID NO: 4. In some embodiments, an isolated polynucleotide that includes a sequence substantially the same as, or identical to, SEQ ID NO: 84 may encode this light chain variable domain amino acid sequence. The described antibodies or antigen-binding fragments may include a heavy chain variable domain that includes an amino acid sequence substantially the same as, or identical to, SEQ ID NO: 8. In some embodiments, an isolated polynucleotide that includes a sequence substantially the same as, or identical to, SEQ ID NO: 88 may encode this heavy chain variable domain amino acid sequence. The described antibodies or antigen-binding fragments may include a light and a heavy chain variable domains, wherein the light chain variable domain includes an amino acid sequence substantially the same as, or identical to, SEQ ID NO: 4, and the heavy chain variable domain includes an amino acid sequence substantially the same as, or identical to, SEQ ID NO: 8.

In some embodiments, the antibodies are produced by antibody-producing cells deposited with the American Type Culture Collection (10801 University Blvd., Manassas, Va. 20110-2209) on Feb. 16, 2012 and have been assigned Accession No. PTA-12538. In some embodiments, the antibodies, or antigen-binding fragments thereof, have the binding affinity for TEM-1 of the antibodies produced by the deposited antibody-producing cells. In some embodiments, the disclosed antibodies, or antigen-binding fragments thereof, comprise the light and heavy chain CDRs of the antibodies produced by the deposited antibody-producing cells. In some embodiments, the antibodies, or antigen-binding fragments thereof, comprise the light and heavy chain variable regions of the antibodies produced by the deposited antibody-producing cells.

Also disclosed are isolated polynucleotides that encode antibodies or antigen-binding fragments that specifically bind to TEM-1. In some embodiments, the isolated polynucleotides encode an antibody or antigen-binding fragment thereof having a light chain CDR1 sequence substantially the same as, or identical to, SEQ ID NO: 1, for example SEQ ID NO: 81. In some embodiments, the isolated polynucleotides encode an antibody or antigen-binding fragment thereof having a light chain CDR2 substantially the same as, or identical to, SEQ ID NO: 2, for example SEQ ID NO: 82. In some embodiments, the isolated polynucleotides encode an antibody or antigen-binding fragment thereof having a light chain CDR3 substantially the same as, or identical to, SEQ ID NO: 3, for example SEQ ID NO: 83. In some embodiments, the isolated polynucleotides encode an antibody or antigen-binding fragment thereof having a heavy chain CDR1 substantially the same as, or identical to, SEQ ID NO: 5, for example SEQ ID NO: 85. In some embodiments, the isolated polynucleotides encode an antibody or antigen-binding fragment thereof having a heavy chain CDR2 substantially the same as, or identical to, SEQ ID NO: 6, for example SEQ ID NO: 86. In some embodiments, the isolated polynucleotides encode an antibody or antigen-binding fragment thereof having a heavy chain CDR3 substantially the same as, or identical to, SEQ ID NO: 7, for example SEQ ID NO: 87. The isolated polynucleotides may encode an antibody or antigen-binding fragment thereof having a light chain with a CDR1 substantially the same as, or identical to, SEQ ID NO: 1, for example SEQ ID NO: 81; a CDR2 substantially the same as, or identical to, SEQ ID NO: 2, for example SEQ ID NO: 82; and a CDR3 substantially the same as, or identical to, SEQ ID NO: 3, for example SEQ ID NO: 83. The isolated polynucleotides may encode an antibody or antigen-binding fragment thereof having a heavy chain CDR1 substantially the same as, or identical to, SEQ ID NO: 5, for example SEQ ID NO: 85; a CDR2 substantially the same as, or identical to, SEQ ID NO: 6, for example SEQ ID NO: 86; and a CDR3 substantially the same as, or identical to, SEQ ID NO: 7, for example SEQ ID NO: 87. The isolated polynucleotides may encode an antibody or antigen-binding fragment thereof having a light chain CDR1 substantially the same as, or identical to, SEQ ID NO: 1, for example SEQ ID NO: 81; a CDR2 encoded by a nucleotide sequence substantially the same as, or identical to, SEQ ID NO: 2, for example SEQ ID NO: 82; and a CDR3 encoded by a nucleotide sequence substantially the same as, or identical to, SEQ ID NO: 3, for example SEQ ID NO: 83; and a heavy chain CDR1 substantially the same as, or identical to, SEQ ID NO: 5, for example SEQ ID NO: 85; a CDR2 substantially the same as, or identical to, SEQ ID NO: 6, for example SEQ ID NO: 86; and a CDR3 substantially the same as, or identical to, SEQ ID NO: 7, for example SEQ ID NO: 87. Antigen-binding arrangements of CDRs may also be engineered using antibody-like proteins as CDR scaffolding. Such engineered antigen-binding proteins are within the scope of the disclosure.

Polynucleotides described herein may encode antibodies or antigen-binding fragments that have a light chain variable domain segment that includes an amino acid sequence substantially the same as, or identical to, SEQ ID NO: 4, for example SEQ ID NO: 84. In some embodiments the described isolated polynucleotides may encode antibodies or antigen-binding fragments that have a heavy chain variable domain segment that includes an amino acid sequence substantially the same as, or identical to, SEQ ID NO: 8, for example SEQ ID NO: 88. In some embodiments the described isolated polynucleotides may encode antibodies or antigen-binding fragments that have a light chain variable domain segment that includes an amino acid sequence substantially the same as, or identical to, SEQ ID NO: 4, for example SEQ ID NO: 84; and a heavy chain variable domain segment that includes an amino acid sequence substantially the same as, or identical to, SEQ ID NO: 8, for example SEQ ID NO: 88. The isolated polynucleotides capable of encoding the variable domain segments provided herein may be included on the same, or different, vectors to produce antibodies or antigen-binding fragments.

Described herein are isolated antibodies and antigen-binding fragments that specifically bind to TEM-1. In some embodiments, the antibodies or antigen-binding fragments are rat IgG, or derivatives thereof. While the antibodies or antigen-binding fragments may be human, humanized, or chimeric, the antibodies or antigen-binding fragments exemplified herein are derived from rats. In some embodiments, antibodies or antigen-binding fragments may include a light chain CDR1 amino acid sequence substantially the same as, or identical to, SEQ ID NO: 9. In some embodiments, antibodies or antigen-binding fragments may include a light chain CDR2 amino acid sequence substantially the same as, or identical to, SEQ ID NO: 10. In some embodiments, antibodies or antigen-binding fragments may include a light chain CDR3 amino acid sequence substantially the same as, or identical to, SEQ ID NO: 11. In some embodiments, antibodies or antigen-binding fragments may include a heavy chain CDR1 amino acid sequence substantially the same as, or identical to, SEQ ID NO: 13. In some embodiments, antibodies or antigen-binding fragments may include a heavy chain CDR2 amino acid sequence substantially the same as, or identical to, SEQ ID NO: 14. In some embodiments, antibodies or antigen-binding fragments may include a heavy chain CDR3 amino acid sequence substantially the same as, or identical to, SEQ ID NO: 15. The antibodies or antigen-binding fragments may include a light chain having a CDR1 amino acid sequence substantially the same as, or identical to, SEQ ID NO: 9; a CDR2 amino acid sequence substantially the same as, or identical to, SEQ ID NO: 10; and a CDR3 amino acid sequence substantially the same as, or identical to, SEQ ID NO: 11. The antibodies or antigen-binding fragments may include a heavy chain having a CDR1 amino acid sequence substantially the same as, or identical to, SEQ ID NO: 13; a CDR2 amino acid sequence substantially the same as, or identical to, SEQ ID NO: 14; and a CDR3 amino acid sequence substantially the same as, or identical to, SEQ ID NO: 15. The antibodies or antigen-binding fragments may include a light chain having a CDR1 amino acid sequence substantially the same as, or identical to, SEQ ID NO: 9; a CDR2 amino acid sequence substantially the same as, or identical to, SEQ ID NO: 10; and a CDR3 amino acid sequence substantially the same as, or identical to, SEQ ID NO: 11, and also have a heavy chain having a CDR1 amino acid sequence substantially the same as, or identical to, SEQ ID NO: 13; a CDR2 amino acid sequence substantially the same as, or identical to, SEQ ID NO: 14; and a CDR3 amino acid sequence substantially the same as, or identical to, SEQ ID NO: 15.

The described antibodies or antigen-binding fragments may include a light chain variable domain that includes an amino acid sequence substantially the same as, or identical to, SEQ ID NO: 12. In some embodiments, an isolated polynucleotide that includes a sequence substantially the same as, or identical to, SEQ ID NO: 92 may encode this light chain variable domain amino acid sequence. The described antibodies or antigen-binding fragments may include a heavy chain variable domain that includes an amino acid sequence substantially the same as, or identical to, SEQ ID NO: 16. In some embodiments, an isolated polynucleotide that includes a sequence substantially the same as, or identical to, SEQ ID NO: 96 may encode this heavy chain variable domain amino acid sequence. The described antibodies or antigen-binding fragments may include a light and a heavy chain variable domains, wherein the light chain variable domain includes an amino acid sequence substantially the same as, or identical to, SEQ ID NO: 12, and the heavy chain variable domain includes an amino acid sequence substantially the same as, or identical to, SEQ ID NO: 16.

In some embodiments, the antibodies are produced by antibody-producing cells deposited with the American Type Culture Collection (10801 University Blvd., Manassas, Va. 20110-2209) on Feb. 16, 2012 and have been assigned Accession No. PTA-12545. In some embodiments, the antibodies, or antigen-binding fragments thereof, have the binding affinity for TEM-1 of the antibodies produced by the deposited antibody-producing cells. In some embodiments, the disclosed antibodies, or antigen-binding fragments thereof, comprise the light and heavy chain CDRs of the antibodies produced by the deposited antibody-producing cells. In some embodiments, the antibodies, or antigen-binding fragments thereof, comprise the light and heavy chain variable regions of the antibodies produced by the deposited antibody-producing cells.

Also disclosed are isolated polynucleotides that encode antibodies or antigen-binding fragments that specifically bind to TEM-1. In some embodiments, the isolated polynucleotides encode an antibody or antigen-binding fragment thereof having a light chain CDR1 sequence substantially the same as, or identical to, SEQ ID NO: 9, for example SEQ ID NO: 89. In some embodiments, the isolated polynucleotides encode an antibody or antigen-binding fragment thereof having a light chain CDR2 substantially the same as, or identical to, SEQ ID NO: 10, for example SEQ ID NO: 90. In some embodiments, the isolated polynucleotides encode an antibody or antigen-binding fragment thereof having a light chain CDR3 substantially the same as, or identical to, SEQ ID NO: 11, for example SEQ ID NO: 91. In some embodiments, the isolated polynucleotides encode an antibody or antigen-binding fragment thereof having a heavy chain CDR1 substantially the same as, or identical to, SEQ ID NO: 13, for example SEQ ID NO: 93. In some embodiments, the isolated polynucleotides encode an antibody or antigen-binding fragment thereof having a heavy chain CDR2 substantially the same as, or identical to, SEQ ID NO: 14, for example SEQ ID NO: 94. In some embodiments, the isolated polynucleotides encode an antibody or antigen-binding fragment thereof having a heavy chain CDR3 substantially the same as, or identical to, SEQ ID NO: 15, for example SEQ ID NO: 95. The isolated polynucleotides may encode an antibody or antigen-binding fragment thereof having a light chain with a CDR1 substantially the same as, or identical to, SEQ ID NO: 9, for example SEQ ID NO: 89; a CDR2 substantially the same as, or identical to, SEQ ID NO: 10, for example SEQ ID NO: 90; and a CDR3 substantially the same as, or identical to, SEQ ID NO: 11, for example SEQ ID NO: 91. The isolated polynucleotides may encode an antibody or antigen-binding fragment thereof having a heavy chain CDR1 substantially the same as, or identical to, SEQ ID NO: 13, for example SEQ ID NO: 93; a CDR2 substantially the same as, or identical to, SEQ ID NO: 14, for example SEQ ID NO: 94; and a CDR3 substantially the same as, or identical to, SEQ ID NO: 15, for example SEQ ID NO: 95. The isolated polynucleotides may encode an antibody or antigen-binding fragment thereof having a light chain CDR1 substantially the same as, or identical to, SEQ ID NO: 9, for example SEQ ID NO: 89; a CDR2 encoded by a nucleotide sequence substantially the same as, or identical to, SEQ ID NO: 10, for example SEQ ID NO: 90; and a CDR3 encoded by a nucleotide sequence substantially the same as, or identical to, SEQ ID NO: 11, for example SEQ ID NO: 91; and a heavy chain CDR1 substantially the same as, or identical to, SEQ ID NO: 13, for example SEQ ID NO: 93; a CDR2 substantially the same as, or identical to, SEQ ID NO: 14, for example SEQ ID NO: 94; and a CDR3 substantially the same as, or identical to, SEQ ID NO: 15, for example SEQ ID NO: 95. Antigen-binding arrangements of CDRs may also be engineered using antibody-like proteins as CDR scaffolding. Such engineered antigen-binding proteins are within the scope of the disclosure.

Polynucleotides described herein may encode antibodies or antigen-binding fragments that have a light chain variable domain segment that includes an amino acid sequence substantially the same as, or identical to, SEQ ID NO: 12, for example SEQ ID NO: 92. In some embodiments the described isolated polynucleotides may encode antibodies or antigen-binding fragments that have a heavy chain variable domain segment that includes an amino acid sequence substantially the same as, or identical to, SEQ ID NO: 16, for example SEQ ID NO: 96. In some embodiments the described isolated polynucleotides may encode antibodies or antigen-binding fragments that have a light chain variable domain segment that includes an amino acid sequence substantially the same as, or identical to, SEQ ID NO: 12, for example SEQ ID NO: 92; and a heavy chain variable domain segment that includes an amino acid sequence substantially the same as, or identical to, SEQ ID NO: 16, for example SEQ ID NO: 96. The isolated polynucleotides capable of encoding the variable domain segments provided herein may be included on the same, or different, vectors to produce antibodies or antigen-binding fragments.

Described herein are isolated antibodies and antigen-binding fragments that specifically bind to TEM-1. In some embodiments, the antibodies or antigen-binding fragments are rat IgG, or derivatives thereof. While the antibodies or antigen-binding fragments may be human, humanized, or chimeric, the antibodies or antigen-binding fragments exemplified herein are derived from rats. In some embodiments, antibodies or antigen-binding fragments may include a light chain CDR1 amino acid sequence substantially the same as, or identical to, SEQ ID NO: 17. In some embodiments, antibodies or antigen-binding fragments may include a light chain CDR2 amino acid sequence substantially the same as, or identical to, SEQ ID NO: 18. In some embodiments, antibodies or antigen-binding fragments may include a light chain CDR3 amino acid sequence substantially the same as, or identical to, SEQ ID NO: 19. In some embodiments, antibodies or antigen-binding fragments may include a heavy chain CDR1 amino acid sequence substantially the same as, or identical to, SEQ ID NO: 21. In some embodiments, antibodies or antigen-binding fragments may include a heavy chain CDR2 amino acid sequence substantially the same as, or identical to, SEQ ID NO: 22. In some embodiments, antibodies or antigen-binding fragments may include a heavy chain CDR3 amino acid sequence substantially the same as, or identical to, SEQ ID NO: 23. The antibodies or antigen-binding fragments may include a light chain having a CDR1 amino acid sequence substantially the same as, or identical to, SEQ ID NO: 17; a CDR2 amino acid sequence substantially the same as, or identical to, SEQ ID NO: 18; and a CDR3 amino acid sequence substantially the same as, or identical to, SEQ ID NO: 19. The antibodies or antigen-binding fragments may include a heavy chain having a CDR1 amino acid sequence substantially the same as, or identical to, SEQ ID NO: 21; a CDR2 amino acid sequence substantially the same as, or identical to, SEQ ID NO: 22; and a CDR3 amino acid sequence substantially the same as, or identical to, SEQ ID NO: 23. The antibodies or antigen-binding fragments may include a light chain having a CDR1 amino acid sequence substantially the same as, or identical to, SEQ ID NO: 17; a CDR2 amino acid sequence substantially the same as, or identical to, SEQ ID NO: 18; and a CDR3 amino acid sequence substantially the same as, or identical to, SEQ ID NO: 19, and also have a heavy chain having a CDR1 amino acid sequence substantially the same as, or identical to, SEQ ID NO: 21; a CDR2 amino acid sequence substantially the same as, or identical to, SEQ ID NO: 22; and a CDR3 amino acid sequence substantially the same as, or identical to, SEQ ID NO: 23.

The described antibodies or antigen-binding fragments may include a light chain variable domain that includes an amino acid sequence substantially the same as, or identical to, SEQ ID NO: 20. In some embodiments, an isolated polynucleotide that includes a sequence substantially the same as, or identical to, SEQ ID NO: 100 may encode this light chain variable domain amino acid sequence. The described antibodies or antigen-binding fragments may include a heavy chain variable domain that includes an amino acid sequence substantially the same as, or identical to, SEQ ID NO: 24. In some embodiments, an isolated polynucleotide that includes a sequence substantially the same as, or identical to, SEQ ID NO: 104 may encode this heavy chain variable domain amino acid sequence. The described antibodies or antigen-binding fragments may include a light and a heavy chain variable domains, wherein the light chain variable domain includes an amino acid sequence substantially the same as, or identical to, SEQ ID NO: 20, and the heavy chain variable domain includes an amino acid sequence substantially the same as, or identical to, SEQ ID NO: 24.

In some embodiments, the antibodies are produced by antibody-producing cells deposited with the American Type Culture Collection (10801 University Blvd., Manassas, Va. 20110-2209) on Feb. 16, 2012 and have been assigned Accession No. PTA-12542. In some embodiments, the antibodies, or antigen-binding fragments thereof, have the binding affinity for TEM-1 of the antibodies produced by the deposited antibody-producing cells. In some embodiments, the disclosed antibodies, or antigen-binding fragments thereof, comprise the light and heavy chain CDRs of the antibodies produced by the deposited antibody-producing cells. In some embodiments, the antibodies, or antigen-binding fragments thereof, comprise the light and heavy chain variable regions of the antibodies produced by the deposited antibody-producing cells.

Also disclosed are isolated polynucleotides that encode antibodies or antigen-binding fragments that specifically bind to TEM-1. In some embodiments, the isolated polynucleotides encode an antibody or antigen-binding fragment thereof having a light chain CDR1 sequence substantially the same as, or identical to, SEQ ID NO: 17, for example SEQ ID NO: 97. In some embodiments, the isolated polynucleotides encode an antibody or antigen-binding fragment thereof having a light chain CDR2 substantially the same as, or identical to, SEQ ID NO: 18, for example SEQ ID NO: 98. In some embodiments, the isolated polynucleotides encode an antibody or antigen-binding fragment thereof having a light chain CDR3 substantially the same as, or identical to, SEQ ID NO: 19, for example SEQ ID NO: 99. In some embodiments, the isolated polynucleotides encode an antibody or antigen-binding fragment thereof having a heavy chain CDR1 substantially the same as, or identical to, SEQ ID NO: 21, for example SEQ ID NO: 101. In some embodiments, the isolated polynucleotides encode an antibody or antigen-binding fragment thereof having a heavy chain CDR2 substantially the same as, or identical to, SEQ ID NO: 22, for example SEQ ID NO: 102. In some embodiments, the isolated polynucleotides encode an antibody or antigen-binding fragment thereof having a heavy chain CDR3 substantially the same as, or identical to, SEQ ID NO: 23, for example SEQ ID NO: 103. The isolated polynucleotides may encode an antibody or antigen-binding fragment thereof having a light chain with a CDR1 substantially the same as, or identical to, SEQ ID NO: 17, for example SEQ ID NO: 97; a CDR2 substantially the same as, or identical to, SEQ ID NO: 18, for example SEQ ID NO: 98; and a CDR3 substantially the same as, or identical to, SEQ ID NO: 19, for example SEQ ID NO: 99. The isolated polynucleotides may encode an antibody or antigen-binding fragment thereof having a heavy chain CDR1 substantially the same as, or identical to, SEQ ID NO: 21, for example SEQ ID NO: 101; a CDR2 substantially the same as, or identical to, SEQ ID NO: 22, for example SEQ ID NO: 102; and a CDR3 substantially the same as, or identical to, SEQ ID NO: 23, for example SEQ ID NO: 103. The isolated polynucleotides may encode an antibody or antigen-binding fragment thereof having a light chain CDR1 substantially the same as, or identical to, SEQ ID NO: 17, for example SEQ ID NO: 97; a CDR2 encoded by a nucleotide sequence substantially the same as, or identical to, SEQ ID NO: 18, for example SEQ ID NO: 98; and a CDR3 encoded by a nucleotide sequence substantially the same as, or identical to, SEQ ID NO: 19, for example SEQ ID NO: 99; and a heavy chain CDR1 substantially the same as, or identical to, SEQ ID NO: 21, for example SEQ ID NO: 101; a CDR2 substantially the same as, or identical to, SEQ ID NO: 22, for example SEQ ID NO: 102; and a CDR3 substantially the same as, or identical to, SEQ ID NO: 23, for example SEQ ID NO: 103. Antigen-binding arrangements of CDRs may also be engineered using antibody-like proteins as CDR scaffolding. Such engineered antigen-binding proteins are within the scope of the disclosure.

Polynucleotides described herein may encode antibodies or antigen-binding fragments that have a light chain variable domain segment that includes an amino acid sequence substantially the same as, or identical to, SEQ ID NO: 20, for example SEQ ID NO: 100. In some embodiments the described isolated polynucleotides may encode antibodies or antigen-binding fragments that have a heavy chain variable domain segment that includes an amino acid sequence substantially the same as, or identical to, SEQ ID NO: 24, for example SEQ ID NO: 104. In some embodiments the described isolated polynucleotides may encode antibodies or antigen-binding fragments that have a light chain variable domain segment that includes an amino acid sequence substantially the same as, or identical to, SEQ ID NO: 20, for example SEQ ID NO: 100; and a heavy chain variable domain segment that includes an amino acid sequence substantially the same as, or identical to, SEQ ID NO: 24, for example SEQ ID NO: 104. The isolated polynucleotides capable of encoding the variable domain segments provided herein may be included on the same, or different, vectors to produce antibodies or antigen-binding fragments.

Described herein are isolated antibodies and antigen-binding fragments that specifically bind to TEM-1. In some embodiments, the antibodies or antigen-binding fragments are rat IgG, or derivatives thereof. While the antibodies or antigen-binding fragments may be human, humanized, or chimeric, the antibodies or antigen-binding fragments exemplified herein are derived from rats. In some embodiments, antibodies or antigen-binding fragments may include a light chain CDR1 amino acid sequence substantially the same as, or identical to, SEQ ID NO: 25. In some embodiments, antibodies or antigen-binding fragments may include a light chain CDR2 amino acid sequence substantially the same as, or identical to, SEQ ID NO: 26. In some embodiments, antibodies or antigen-binding fragments may include a light chain CDR3 amino acid sequence substantially the same as, or identical to, SEQ ID NO: 27. In some embodiments, antibodies or antigen-binding fragments may include a heavy chain CDR1 amino acid sequence substantially the same as, or identical to, SEQ ID NO: 29. In some embodiments, antibodies or antigen-binding fragments may include a heavy chain CDR2 amino acid sequence substantially the same as, or identical to, SEQ ID NO: 30. In some embodiments, antibodies or antigen-binding fragments may include a heavy chain CDR3 amino acid sequence substantially the same as, or identical to, SEQ ID NO: 31. The antibodies or antigen-binding fragments may include a light chain having a CDR1 amino acid sequence substantially the same as, or identical to, SEQ ID NO: 25; a CDR2 amino acid sequence substantially the same as, or identical to, SEQ ID NO: 26; and a CDR3 amino acid sequence substantially the same as, or identical to, SEQ ID NO: 27. The antibodies or antigen-binding fragments may include a heavy chain having a CDR1 amino acid sequence substantially the same as, or identical to, SEQ ID NO: 29; a CDR2 amino acid sequence substantially the same as, or identical to, SEQ ID NO: 30; and a CDR3 amino acid sequence substantially the same as, or identical to, SEQ ID NO: 31. The antibodies or antigen-binding fragments may include a light chain having a CDR1 amino acid sequence substantially the same as, or identical to, SEQ ID NO: 25; a CDR2 amino acid sequence substantially the same as, or identical to, SEQ ID NO: 26; and a CDR3 amino acid sequence substantially the same as, or identical to, SEQ ID NO: 27, and also have a heavy chain having a CDR1 amino acid sequence substantially the same as, or identical to, SEQ ID NO: 29; a CDR2 amino acid sequence substantially the same as, or identical to, SEQ ID NO: 30; and a CDR3 amino acid sequence substantially the same as, or identical to, SEQ ID NO: 31.

The described antibodies or antigen-binding fragments may include a light chain variable domain that includes an amino acid sequence substantially the same as, or identical to, SEQ ID NO: 28. In some embodiments, an isolated polynucleotide that includes a sequence substantially the same as, or identical to, SEQ ID NO: 108 may encode this light chain variable domain amino acid sequence. The described antibodies or antigen-binding fragments may include a heavy chain variable domain that includes an amino acid sequence substantially the same as, or identical to, SEQ ID NO: 32. In some embodiments, an isolated polynucleotide that includes a sequence substantially the same as, or identical to, SEQ ID NO: 112 may encode this heavy chain variable domain amino acid sequence. The described antibodies or antigen-binding fragments may include a light and a heavy chain variable domains, wherein the light chain variable domain includes an amino acid sequence substantially the same as, or identical to, SEQ ID NO: 28, and the heavy chain variable domain includes an amino acid sequence substantially the same as, or identical to, SEQ ID NO: 32.

In some embodiments, the antibodies are produced by antibody-producing cells deposited with the American Type Culture Collection (10801 University Blvd., Manassas, Va. 20110-2209) on Feb. 16, 2012 and have been assigned Accession No. PTA-12546. In some embodiments, the antibodies, or antigen-binding fragments thereof, have the binding affinity for TEM-1 of the antibodies produced by the deposited antibody-producing cells. In some embodiments, the disclosed antibodies, or antigen-binding fragments thereof, comprise the light and heavy chain CDRs of the antibodies produced by the deposited antibody-producing cells. In some embodiments, the antibodies, or antigen-binding fragments thereof, comprise the light and heavy chain variable regions of the antibodies produced by the deposited antibody-producing cells.

Also disclosed are isolated polynucleotides that encode antibodies or antigen-binding fragments that specifically bind to TEM-1. In some embodiments, the isolated polynucleotides encode an antibody or antigen-binding fragment thereof having a light chain CDR1 sequence substantially the same as, or identical to, SEQ ID NO: 25, for example SEQ ID NO: 105. In some embodiments, the isolated polynucleotides encode an antibody or antigen-binding fragment thereof having a light chain CDR2 substantially the same as, or identical to, SEQ ID NO: 26, for example SEQ ID NO: 106. In some embodiments, the isolated polynucleotides encode an antibody or antigen-binding fragment thereof having a light chain CDR3 substantially the same as, or identical to, SEQ ID NO: 27, for example SEQ ID NO: 107. In some embodiments, the isolated polynucleotides encode an antibody or antigen-binding fragment thereof having a heavy chain CDR1 substantially the same as, or identical to, SEQ ID NO: 29, for example SEQ ID NO: 109. In some embodiments, the isolated polynucleotides encode an antibody or antigen-binding fragment thereof having a heavy chain CDR2 substantially the same as, or identical to, SEQ ID NO: 30, for example SEQ ID NO: 110. In some embodiments, the isolated polynucleotides encode an antibody or antigen-binding fragment thereof having a heavy chain CDR3 substantially the same as, or identical to, SEQ ID NO: 31, for example SEQ ID NO: 111. The isolated polynucleotides may encode an antibody or antigen-binding fragment thereof having a light chain with a CDR1 substantially the same as, or identical to, SEQ ID NO: 25, for example SEQ ID NO: 105; a CDR2 substantially the same as, or identical to, SEQ ID NO: 26, for example SEQ ID NO: 106; and a CDR3 substantially the same as, or identical to, SEQ ID NO: 27, for example SEQ ID NO: 107. The isolated polynucleotides may encode an antibody or antigen-binding fragment thereof having a heavy chain CDR1 substantially the same as, or identical to, SEQ ID NO: 29, for example SEQ ID NO: 109; a CDR2 substantially the same as, or identical to, SEQ ID NO: 30, for example SEQ ID NO: 110; and a CDR3 substantially the same as, or identical to, SEQ ID NO: 31, for example SEQ ID NO: 111. The isolated polynucleotides may encode an antibody or antigen-binding fragment thereof having a light chain CDR1 substantially the same as, or identical to, SEQ ID NO: 25, for example SEQ ID NO: 105; a CDR2 encoded by a nucleotide sequence substantially the same as, or identical to, SEQ ID NO: 26, for example SEQ ID NO: 106; and a CDR3 encoded by a nucleotide sequence substantially the same as, or identical to, SEQ ID NO: 27, for example SEQ ID NO: 107; and a heavy chain CDR1 substantially the same as, or identical to, SEQ ID NO: 29, for example SEQ ID NO: 109; a CDR2 substantially the same as, or identical to, SEQ ID NO: 30, for example SEQ ID NO: 110; and a CDR3 substantially the same as, or identical to, SEQ ID NO: 31, for example SEQ ID NO: 111. Antigen-binding arrangements of CDRs may also be engineered using antibody-like proteins as CDR scaffolding. Such engineered antigen-binding proteins are within the scope of the disclosure.

Polynucleotides described herein may encode antibodies or antigen-binding fragments that have a light chain variable domain segment that includes an amino acid sequence substantially the same as, or identical to, SEQ ID NO: 28, for example SEQ ID NO: 108. In some embodiments the described isolated polynucleotides may encode antibodies or antigen-binding fragments that have a heavy chain variable domain segment that includes an amino acid sequence substantially the same as, or identical to, SEQ ID NO: 32, for example SEQ ID NO: 112. In some embodiments the described isolated polynucleotides may encode antibodies or antigen-binding fragments that have a light chain variable domain segment that includes an amino acid sequence substantially the same as, or identical to, SEQ ID NO: 28, for example SEQ ID NO: 108; and a heavy chain variable domain segment that includes an amino acid sequence substantially the same as, or identical to, SEQ ID NO: 32, for example SEQ ID NO: 112. The isolated polynucleotides capable of encoding the variable domain segments provided herein may be included on the same, or different, vectors to produce antibodies or antigen-binding fragments.

Described herein are isolated antibodies and antigen-binding fragments that specifically bind to TEM-1. In some embodiments, the antibodies or antigen-binding fragments are derived from rat IgG, or derivatives thereof. While the antibodies or antigen-binding fragments may be human, humanized, or chimeric, the antibodies or antigen-binding fragments exemplified herein are derived from rats. In some embodiments, antibodies or antigen-binding fragments may include a light chain CDR1 amino acid sequence substantially the same as, or identical to, SEQ ID NO: 33. In some embodiments, antibodies or antigen-binding fragments may include a light chain CDR2 amino acid sequence substantially the same as, or identical to, SEQ ID NO: 34. In some embodiments, antibodies or antigen-binding fragments may include a light chain CDR3 amino acid sequence substantially the same as, or identical to, SEQ ID NO: 35. In some embodiments, antibodies or antigen-binding fragments may include a heavy chain CDR1 amino acid sequence substantially the same as, or identical to, SEQ ID NO: 37. In some embodiments, antibodies or antigen-binding fragments may include a heavy chain CDR2 amino acid sequence substantially the same as, or identical to, SEQ ID NO: 38. In some embodiments, antibodies or antigen-binding fragments may include a heavy chain CDR3 amino acid sequence substantially the same as, or identical to, SEQ ID NO: 39. The antibodies or antigen-binding fragments may include a light chain having a CDR1 amino acid sequence substantially the same as, or identical to, SEQ ID NO: 33; a CDR2 amino acid sequence substantially the same as, or identical to, SEQ ID NO: 34; and a CDR3 amino acid sequence substantially the same as, or identical to, SEQ ID NO: 35. The antibodies or antigen-binding fragments may include a heavy chain having a CDR1 amino acid sequence substantially the same as, or identical to, SEQ ID NO: 37; a CDR2 amino acid sequence substantially the same as, or identical to, SEQ ID NO: 38; and a CDR3 amino acid sequence substantially the same as, or identical to, SEQ ID NO: 39. The antibodies or antigen-binding fragments may include a light chain having a CDR1 amino acid sequence substantially the same as, or identical to, SEQ ID NO: 33; a CDR2 amino acid sequence substantially the same as, or identical to, SEQ ID NO: 34; and a CDR3 amino acid sequence substantially the same as, or identical to, SEQ ID NO: 35, and also have a heavy chain having a CDR1 amino acid sequence substantially the same as, or identical to, SEQ ID NO: 37; a CDR2 amino acid sequence substantially the same as, or identical to, SEQ ID NO: 38; and a CDR3 amino acid sequence substantially the same as, or identical to, SEQ ID NO: 39.

The described antibodies or antigen-binding fragments may include a light chain variable domain that includes an amino acid sequence substantially the same as, or identical to, SEQ ID NO: 36. In some embodiments, an isolated polynucleotide that includes a sequence substantially the same as, or identical to, SEQ ID NO: 116 may encode this light chain variable domain amino acid sequence. The described antibodies or antigen-binding fragments may include a heavy chain variable domain that includes an amino acid sequence substantially the same as, or identical to, SEQ ID NO: 40. In some embodiments, an isolated polynucleotide that includes a sequence substantially the same as, or identical to, SEQ ID NO: 120 may encode this heavy chain variable domain amino acid sequence. The described antibodies or antigen-binding fragments may include a light and a heavy chain variable domains, wherein the light chain variable domain includes an amino acid sequence substantially the same as, or identical to, SEQ ID NO: 36, and the heavy chain variable domain includes an amino acid sequence substantially the same as, or identical to, SEQ ID NO: 40.

In some embodiments, the antibodies are produced by antibody-producing cells deposited with the American Type Culture Collection (10801 University Blvd., Manassas, Va. 20110-2209) on Feb. 16, 2012 and have been assigned Accession No. PTA-12541. In some embodiments, the antibodies, or antigen-binding fragments thereof, have the binding affinity for TEM-1 of the antibodies produced by the deposited antibody-producing cells. In some embodiments, the disclosed antibodies, or antigen-binding fragments thereof, comprise the light and heavy chain CDRs of the antibodies produced by the deposited antibody-producing cells. In some embodiments, the antibodies, or antigen-binding fragments thereof, comprise the light and heavy chain variable regions of the antibodies produced by the deposited antibody-producing cells.

Also disclosed are isolated polynucleotides that encode antibodies or antigen-binding fragments that specifically bind to TEM-1. In some embodiments, the isolated polynucleotides encode an antibody or antigen-binding fragment thereof having a light chain CDR1 sequence substantially the same as, or identical to, SEQ ID NO: 33, for example SEQ ID NO: 113. In some embodiments, the isolated polynucleotides encode an antibody or antigen-binding fragment thereof having a light chain CDR2 substantially the same as, or identical to, SEQ ID NO: 34, for example SEQ ID NO: 114. In some embodiments, the isolated polynucleotides encode an antibody or antigen-binding fragment thereof having a light chain CDR3 substantially the same as, or identical to, SEQ ID NO: 35, for example SEQ ID NO: 115. In some embodiments, the isolated polynucleotides encode an antibody or antigen-binding fragment thereof having a heavy chain CDR1 substantially the same as, or identical to, SEQ ID NO: 37, for example SEQ ID NO: 117. In some embodiments, the isolated polynucleotides encode an antibody or antigen-binding fragment thereof having a heavy chain CDR2 substantially the same as, or identical to, SEQ ID NO: 38, for example SEQ ID NO: 118. In some embodiments, the isolated polynucleotides encode an antibody or antigen-binding fragment thereof having a heavy chain CDR3 substantially the same as, or identical to, SEQ ID NO: 39, for example SEQ ID NO: 119. The isolated polynucleotides may encode an antibody or antigen-binding fragment thereof having a light chain with a CDR1 substantially the same as, or identical to, SEQ ID NO: 33, for example SEQ ID NO: 113; a CDR2 substantially the same as, or identical to, SEQ ID NO: 34, for example SEQ ID NO: 114; and a CDR3 substantially the same as, or identical to, SEQ ID NO: 35, for example SEQ ID NO: 115. The isolated polynucleotides may encode an antibody or antigen-binding fragment thereof having a heavy chain CDR1 substantially the same as, or identical to, SEQ ID NO: 37, for example SEQ ID NO: 117; a CDR2 substantially the same as, or identical to, SEQ ID NO: 38, for example SEQ ID NO: 118; and a CDR3 substantially the same as, or identical to, SEQ ID NO: 39, for example SEQ ID NO: 119. The isolated polynucleotides may encode an antibody or antigen-binding fragment thereof having a light chain CDR1 substantially the same as, or identical to, SEQ ID NO: 33, for example SEQ ID NO: 113; a CDR2 encoded by a nucleotide sequence substantially the same as, or identical to, SEQ ID NO: 34, for example SEQ ID NO: 114; and a CDR3 encoded by a nucleotide sequence substantially the same as, or identical to, SEQ ID NO: 35, for example SEQ ID NO: 115; and a heavy chain CDR1 substantially the same as, or identical to, SEQ ID NO: 37, for example SEQ ID NO: 117; a CDR2 substantially the same as, or identical to, SEQ ID NO: 38, for example SEQ ID NO: 118; and a CDR3 substantially the same as, or identical to, SEQ ID NO: 39, for example SEQ ID NO: 119. Antigen-binding arrangements of CDRs may also be engineered using antibody-like proteins as CDR scaffolding. Such engineered antigen-binding proteins are within the scope of the disclosure.

Polynucleotides described herein may encode antibodies or antigen-binding fragments that have a light chain variable domain segment that includes an amino acid sequence substantially the same as, or identical to, SEQ ID NO: 36, for example SEQ ID NO: 116. In some embodiments the described isolated polynucleotides may encode antibodies or antigen-binding fragments that have a heavy chain variable domain segment that includes an amino acid sequence substantially the same as, or identical to, SEQ ID NO: 40, for example SEQ ID NO: 120. In some embodiments the described isolated polynucleotides may encode antibodies or antigen-binding fragments that have a light chain variable domain segment that includes an amino acid sequence substantially the same as, or identical to, SEQ ID NO: 36, for example SEQ ID NO: 116; and a heavy chain variable domain segment that includes an amino acid sequence substantially the same as, or identical to, SEQ ID NO: 40, for example SEQ ID NO: 120. The isolated polynucleotides capable of encoding the variable domain segments provided herein may be included on the same, or different, vectors to produce antibodies or antigen-binding fragments.

Described herein are isolated antibodies and antigen-binding fragments that specifically bind to TEM-1. In some embodiments, the antibodies or antigen-binding fragments are derived from rat IgG, or derivatives thereof. While the antibodies or antigen-binding fragments may be human, humanized, or chimeric, the antibodies or antigen-binding fragments exemplified herein are derived from rats. In some embodiments, antibodies or antigen-binding fragments may include a light chain CDR1 amino acid sequence substantially the same as, or identical to, SEQ ID NO: 41. In some embodiments, antibodies or antigen-binding fragments may include a light chain CDR2 amino acid sequence substantially the same as, or identical to, SEQ ID NO: 42. In some embodiments, antibodies or antigen-binding fragments may include a light chain CDR3 amino acid sequence substantially the same as, or identical to, SEQ ID NO: 43. In some embodiments, antibodies or antigen-binding fragments may include a heavy chain CDR1 amino acid sequence substantially the same as, or identical to, SEQ ID NO: 45. In some embodiments, antibodies or antigen-binding fragments may include a heavy chain CDR2 amino acid sequence substantially the same as, or identical to, SEQ ID NO: 46. In some embodiments, antibodies or antigen-binding fragments may include a heavy chain CDR3 amino acid sequence substantially the same as, or identical to, SEQ ID NO: 47. The antibodies or antigen-binding fragments may include a light chain having a CDR1 amino acid sequence substantially the same as, or identical to, SEQ ID NO: 41; a CDR2 amino acid sequence substantially the same as, or identical to, SEQ ID NO: 42; and a CDR3 amino acid sequence substantially the same as, or identical to, SEQ ID NO: 43. The antibodies or antigen-binding fragments may include a heavy chain having a CDR1 amino acid sequence substantially the same as, or identical to, SEQ ID NO: 45; a CDR2 amino acid sequence substantially the same as, or identical to, SEQ ID NO: 46; and a CDR3 amino acid sequence substantially the same as, or identical to, SEQ ID NO: 47. The antibodies or antigen-binding fragments may include a light chain having a CDR1 amino acid sequence substantially the same as, or identical to, SEQ ID NO: 41; a CDR2 amino acid sequence substantially the same as, or identical to, SEQ ID NO: 42; and a CDR3 amino acid sequence substantially the same as, or identical to, SEQ ID NO: 43, and also have a heavy chain having a CDR1 amino acid sequence substantially the same as, or identical to, SEQ ID NO: 45; a CDR2 amino acid sequence substantially the same as, or identical to, SEQ ID NO: 46; and a CDR3 amino acid sequence substantially the same as, or identical to, SEQ ID NO: 47.

The described antibodies or antigen-binding fragments may include a light chain variable domain that includes an amino acid sequence substantially the same as, or identical to, SEQ ID NO: 44. In some embodiments, an isolated polynucleotide that includes a sequence substantially the same as, or identical to, SEQ ID NO: 124 may encode this light chain variable domain amino acid sequence. The described antibodies or antigen-binding fragments may include a heavy chain variable domain that includes an amino acid sequence substantially the same as, or identical to, SEQ ID NO: 48. In some embodiments, an isolated polynucleotide that includes a sequence substantially the same as, or identical to, SEQ ID NO: 128 may encode this heavy chain variable domain amino acid sequence. The described antibodies or antigen-binding fragments may include a light and a heavy chain variable domains, wherein the light chain variable domain includes an amino acid sequence substantially the same as, or identical to, SEQ ID NO: 44, and the heavy chain variable domain includes an amino acid sequence substantially the same as, or identical to, SEQ ID NO: 48.

In some embodiments, the antibodies are produced by antibody-producing cells deposited with the American Type Culture Collection (10801 University Blvd., Manassas, Va. 20110-2209) on Feb. 16, 2012 and have been assigned Accession No. PTA-12539. In some embodiments, the antibodies, or antigen-binding fragments thereof, have the binding affinity for TEM-1 of the antibodies produced by the deposited antibody-producing cells. In some embodiments, the disclosed antibodies, or antigen-binding fragments thereof, comprise the light and heavy chain CDRs of the antibodies produced by the deposited antibody-producing cells. In some embodiments, the antibodies, or antigen-binding fragments thereof, comprise the light and heavy chain variable regions of the antibodies produced by the deposited antibody-producing cells.

Also disclosed are isolated polynucleotides that encode antibodies or antigen-binding fragments that specifically bind to TEM-1. In some embodiments, the isolated polynucleotides encode an antibody or antigen-binding fragment thereof having a light chain CDR1 sequence substantially the same as, or identical to, SEQ ID NO: 41, for example SEQ ID NO: 121. In some embodiments, the isolated polynucleotides encode an antibody or antigen-binding fragment thereof having a light chain CDR2 substantially the same as, or identical to, SEQ ID NO: 42, for example SEQ ID NO: 122. In some embodiments, the isolated polynucleotides encode an antibody or antigen-binding fragment thereof having a light chain CDR3 substantially the same as, or identical to, SEQ ID NO: 43, for example SEQ ID NO: 123. In some embodiments, the isolated polynucleotides encode an antibody or antigen-binding fragment thereof having a heavy chain CDR1 substantially the same as, or identical to, SEQ ID NO: 45, for example SEQ ID NO: 125. In some embodiments, the isolated polynucleotides encode an antibody or antigen-binding fragment thereof having a heavy chain CDR2 substantially the same as, or identical to, SEQ ID NO: 46, for example SEQ ID NO: 126. In some embodiments, the isolated polynucleotides encode an antibody or antigen-binding fragment thereof having a heavy chain CDR3 substantially the same as, or identical to, SEQ ID NO: 47, for example SEQ ID NO: 127. The isolated polynucleotides may encode an antibody or antigen-binding fragment thereof having a light chain with a CDR1 substantially the same as, or identical to, SEQ ID NO: 41, for example SEQ ID NO: 121; a CDR2 substantially the same as, or identical to, SEQ ID NO: 42, for example SEQ ID NO: 122; and a CDR3 substantially the same as, or identical to, SEQ ID NO: 43, for example SEQ ID NO: 123. The isolated polynucleotides may encode an antibody or antigen-binding fragment thereof having a heavy chain CDR1 substantially the same as, or identical to, SEQ ID NO: 45, for example SEQ ID NO: 125; a CDR2 substantially the same as, or identical to, SEQ ID NO: 46, for example SEQ ID NO: 126; and a CDR3 substantially the same as, or identical to, SEQ ID NO: 47, for example SEQ ID NO: 127. The isolated polynucleotides may encode an antibody or antigen-binding fragment thereof having a light chain CDR1 substantially the same as, or identical to, SEQ ID NO: 41, for example SEQ ID NO: 121; a CDR2 encoded by a nucleotide sequence substantially the same as, or identical to, SEQ ID NO: 42, for example SEQ ID NO: 122; and a CDR3 encoded by a nucleotide sequence substantially the same as, or identical to, SEQ ID NO: 43, for example SEQ ID NO: 123; and a heavy chain CDR1 substantially the same as, or identical to, SEQ ID NO: 45, for example SEQ ID NO: 125; a CDR2 substantially the same as, or identical to, SEQ ID NO: 46, for example SEQ ID NO: 126; and a CDR3 substantially the same as, or identical to, SEQ ID NO: 47, for example SEQ ID NO: 127. Antigen-binding arrangements of CDRs may also be engineered using antibody-like proteins as CDR scaffolding. Such engineered antigen-binding proteins are within the scope of the disclosure.

Polynucleotides described herein may encode antibodies or antigen-binding fragments that have a light chain variable domain segment that includes an amino acid sequence substantially the same as, or identical to, SEQ ID NO: 44, for example SEQ ID NO: 124. In some embodiments the described isolated polynucleotides may encode antibodies or antigen-binding fragments that have a heavy chain variable domain segment that includes an amino acid sequence substantially the same as, or identical to, SEQ ID NO: 48, for example SEQ ID NO: 128. In some embodiments the described isolated polynucleotides may encode antibodies or antigen-binding fragments that have a light chain variable domain segment that includes an amino acid sequence substantially the same as, or identical to, SEQ ID NO: 44, for example SEQ ID NO: 124; and a heavy chain variable domain segment that includes an amino acid sequence substantially the same as, or identical to, SEQ ID NO: 48, for example SEQ ID NO: 128. The isolated polynucleotides capable of encoding the variable domain segments provided herein may be included on the same, or different, vectors to produce antibodies or antigen-binding fragments.

Described herein are isolated antibodies and antigen-binding fragments that specifically bind to TEM-1. In some embodiments, the antibodies or antigen-binding fragments are derived from rat IgG, or derivatives thereof. While the antibodies or antigen-binding fragments may be human, humanized, or chimeric, the antibodies or antigen-binding fragments exemplified herein are derived from rats. In some embodiments, antibodies or antigen-binding fragments may include a light chain CDR1 amino acid sequence substantially the same as, or identical to, SEQ ID NO: 49. In some embodiments, antibodies or antigen-binding fragments may include a light chain CDR2 amino acid sequence substantially the same as, or identical to, SEQ ID NO: 50. In some embodiments, antibodies or antigen-binding fragments may include a light chain CDR3 amino acid sequence substantially the same as, or identical to, SEQ ID NO: 51. In some embodiments, antibodies or antigen-binding fragments may include a heavy chain CDR1 amino acid sequence substantially the same as, or identical to, SEQ ID NO: 53. In some embodiments, antibodies or antigen-binding fragments may include a heavy chain CDR2 amino acid sequence substantially the same as, or identical to, SEQ ID NO: 54. In some embodiments, antibodies or antigen-binding fragments may include a heavy chain CDR3 amino acid sequence substantially the same as, or identical to, SEQ ID NO: 55. The antibodies or antigen-binding fragments may include a light chain having a CDR1 amino acid sequence substantially the same as, or identical to, SEQ ID NO: 49; a CDR2 amino acid sequence substantially the same as, or identical to, SEQ ID NO: 50; and a CDR3 amino acid sequence substantially the same as, or identical to, SEQ ID NO: 51. The antibodies or antigen-binding fragments may include a heavy chain having a CDR1 amino acid sequence substantially the same as, or identical to, SEQ ID NO: 53; a CDR2 amino acid sequence substantially the same as, or identical to, SEQ ID NO: 54; and a CDR3 amino acid sequence substantially the same as, or identical to, SEQ ID NO: 55. The antibodies or antigen-binding fragments may include a light chain having a CDR1 amino acid sequence substantially the same as, or identical to, SEQ ID NO: 49; a CDR2 amino acid sequence substantially the same as, or identical to, SEQ ID NO: 50; and a CDR3 amino acid sequence substantially the same as, or identical to, SEQ ID NO: 51, and also have a heavy chain having a CDR1 amino acid sequence substantially the same as, or identical to, SEQ ID NO: 53; a CDR2 amino acid sequence substantially the same as, or identical to, SEQ ID NO: 54; and a CDR3 amino acid sequence substantially the same as, or identical to, SEQ ID NO: 55.

The described antibodies or antigen-binding fragments may include a light chain variable domain that includes an amino acid sequence substantially the same as, or identical to, SEQ ID NO: 52. In some embodiments, an isolated polynucleotide that includes a sequence substantially the same as, or identical to, SEQ ID NO: 132 may encode this light chain variable domain amino acid sequence. The described antibodies or antigen-binding fragments may include a heavy chain variable domain that includes an amino acid sequence substantially the same as, or identical to, SEQ ID NO: 56. In some embodiments, an isolated polynucleotide that includes a sequence substantially the same as, or identical to, SEQ ID NO: 136 may encode this heavy chain variable domain amino acid sequence. The described antibodies or antigen-binding fragments may include a light and a heavy chain variable domains, wherein the light chain variable domain includes an amino acid sequence substantially the same as, or identical to, SEQ ID NO: 52, and the heavy chain variable domain includes an amino acid sequence substantially the same as, or identical to, SEQ ID NO: 56.

In some embodiments, the antibodies are produced by antibody-producing cells deposited with the American Type Culture Collection (10801 University Blvd., Manassas, Va. 20110-2209) on Feb. 16, 2012 and have been assigned Accession No. PTA-12543. In some embodiments, the antibodies, or antigen-binding fragments thereof, have the binding affinity for TEM-1 of the antibodies produced by the deposited antibody-producing cells. In some embodiments, the disclosed antibodies, or antigen-binding fragments thereof, comprise the light and heavy chain CDRs of the antibodies produced by the deposited antibody-producing cells. In some embodiments, the antibodies, or antigen-binding fragments thereof, comprise the light and heavy chain variable regions of the antibodies produced by the deposited antibody-producing cells.

Also disclosed are isolated polynucleotides that encode antibodies or antigen-binding fragments that specifically bind to TEM-1. In some embodiments, the isolated polynucleotides encode an antibody or antigen-binding fragment thereof having a light chain CDR1 sequence substantially the same as, or identical to, SEQ ID NO: 49, for example SEQ ID NO: 129. In some embodiments, the isolated polynucleotides encode an antibody or antigen-binding fragment thereof having a light chain CDR2 substantially the same as, or identical to, SEQ ID NO: 50, for example SEQ ID NO: 130. In some embodiments, the isolated polynucleotides encode an antibody or antigen-binding fragment thereof having a light chain CDR3 substantially the same as, or identical to, SEQ ID NO: 51, for example SEQ ID NO: 131. In some embodiments, the isolated polynucleotides encode an antibody or antigen-binding fragment thereof having a heavy chain CDR1 substantially the same as, or identical to, SEQ ID NO: 53, for example SEQ ID NO: 133. In some embodiments, the isolated polynucleotides encode an antibody or antigen-binding fragment thereof having a heavy chain CDR2 substantially the same as, or identical to, SEQ ID NO: 54, for example SEQ ID NO: 134. In some embodiments, the isolated polynucleotides encode an antibody or antigen-binding fragment thereof having a heavy chain CDR3 substantially the same as, or identical to, SEQ ID NO: 55, for example SEQ ID NO: 135. The isolated polynucleotides may encode an antibody or antigen-binding fragment thereof having a light chain with a CDR1 substantially the same as, or identical to, SEQ ID NO: 49, for example SEQ ID NO: 129; a CDR2 substantially the same as, or identical to, SEQ ID NO: 50, for example SEQ ID NO: 130; and a CDR3 substantially the same as, or identical to, SEQ ID NO: 51, for example SEQ ID NO: 131. The isolated polynucleotides may encode an antibody or antigen-binding fragment thereof having a heavy chain CDR1 substantially the same as, or identical to, SEQ ID NO: 53, for example SEQ ID NO: 133; a CDR2 substantially the same as, or identical to, SEQ ID NO: 54, for example SEQ ID NO: 134; and a CDR3 substantially the same as, or identical to, SEQ ID NO: 55, for example SEQ ID NO: 135. The isolated polynucleotides may encode an antibody or antigen-binding fragment thereof having a light chain CDR1 substantially the same as, or identical to, SEQ ID NO: 49, for example SEQ ID NO: 129; a CDR2 encoded by a nucleotide sequence substantially the same as, or identical to, SEQ ID NO: 50, for example SEQ ID NO: 130; and a CDR3 encoded by a nucleotide sequence substantially the same as, or identical to, SEQ ID NO: 51, for example SEQ ID NO: 131; and a heavy chain CDR1 substantially the same as, or identical to, SEQ ID NO: 53, for example SEQ ID NO: 133; a CDR2 substantially the same as, or identical to, SEQ ID NO: 54, for example SEQ ID NO: 134; and a CDR3 substantially the same as, or identical to, SEQ ID NO: 55, for example SEQ ID NO: 135. Antigen-binding arrangements of CDRs may also be engineered using antibody-like proteins as CDR scaffolding. Such engineered antigen-binding proteins are within the scope of the disclosure.

Polynucleotides described herein may encode antibodies or antigen-binding fragments that have a light chain variable domain segment that includes an amino acid sequence substantially the same as, or identical to, SEQ ID NO: 52, for example SEQ ID NO: 132. In some embodiments the described isolated polynucleotides may encode antibodies or antigen-binding fragments that have a heavy chain variable domain segment that includes an amino acid sequence substantially the same as, or identical to, SEQ ID NO: 56, for example SEQ ID NO: 136. In some embodiments the described isolated polynucleotides may encode antibodies or antigen-binding fragments that have a light chain variable domain segment that includes an amino acid sequence substantially the same as, or identical to, SEQ ID NO: 52, for example SEQ ID NO: 132; and a heavy chain variable domain segment that includes an amino acid sequence substantially the same as, or identical to, SEQ ID NO: 56, for example SEQ ID NO: 136. The isolated polynucleotides capable of encoding the variable domain segments provided herein may be included on the same, or different, vectors to produce antibodies or antigen-binding fragments.

Described herein are isolated antibodies and antigen-binding fragments that specifically bind to TEM-1. In some embodiments, the antibodies or antigen-binding fragments are derived from rat IgG, or derivatives thereof. While the antibodies or antigen-binding fragments may be human, humanized, or chimeric, the antibodies or antigen-binding fragments exemplified herein are derived from rats. In some embodiments, antibodies or antigen-binding fragments may include a light chain CDR1 amino acid sequence substantially the same as, or identical to, SEQ ID NO: 57. In some embodiments, antibodies or antigen-binding fragments may include a light chain CDR2 amino acid sequence substantially the same as, or identical to, SEQ ID NO: 58. In some embodiments, antibodies or antigen-binding fragments may include a light chain CDR3 amino acid sequence substantially the same as, or identical to, SEQ ID NO: 59. In some embodiments, antibodies or antigen-binding fragments may include a heavy chain CDR1 amino acid sequence substantially the same as, or identical to, SEQ ID NO: 61. In some embodiments, antibodies or antigen-binding fragments may include a heavy chain CDR2 amino acid sequence substantially the same as, or identical to, SEQ ID NO: 62. In some embodiments, antibodies or antigen-binding fragments may include a heavy chain CDR3 amino acid sequence substantially the same as, or identical to, SEQ ID NO: 63. The antibodies or antigen-binding fragments may include a light chain having a CDR1 amino acid sequence substantially the same as, or identical to, SEQ ID NO: 57; a CDR2 amino acid sequence substantially the same as, or identical to, SEQ ID NO: 58; and a CDR3 amino acid sequence substantially the same as, or identical to, SEQ ID NO: 59. The antibodies or antigen-binding fragments may include a heavy chain having a CDR1 amino acid sequence substantially the same as, or identical to, SEQ ID NO: 61; a CDR2 amino acid sequence substantially the same as, or identical to, SEQ ID NO: 62; and a CDR3 amino acid sequence substantially the same as, or identical to, SEQ ID NO: 63. The antibodies or antigen-binding fragments may include a light chain having a CDR1 amino acid sequence substantially the same as, or identical to, SEQ ID NO: 57; a CDR2 amino acid sequence substantially the same as, or identical to, SEQ ID NO: 58; and a CDR3 amino acid sequence substantially the same as, or identical to, SEQ ID NO: 59, and also have a heavy chain having a CDR1 amino acid sequence substantially the same as, or identical to, SEQ ID NO: 61; a CDR2 amino acid sequence substantially the same as, or identical to, SEQ ID NO: 62; and a CDR3 amino acid sequence substantially the same as, or identical to, SEQ ID NO: 63.

The described antibodies or antigen-binding fragments may include a light chain variable domain that includes an amino acid sequence substantially the same as, or identical to, SEQ ID NO: 60. In some embodiments, an isolated polynucleotide that includes a sequence substantially the same as, or identical to, SEQ ID NO: 140 may encode this light chain variable domain amino acid sequence. The described antibodies or antigen-binding fragments may include a heavy chain variable domain that includes an amino acid sequence substantially the same as, or identical to, SEQ ID NO: 64. In some embodiments, an isolated polynucleotide that includes a sequence substantially the same as, or identical to, SEQ ID NO: 144 may encode this heavy chain variable domain amino acid sequence. The described antibodies or antigen-binding fragments may include a light and a heavy chain variable domains, wherein the light chain variable domain includes an amino acid sequence substantially the same as, or identical to, SEQ ID NO: 60, and the heavy chain variable domain includes an amino acid sequence substantially the same as, or identical to, SEQ ID NO: 64.

In some embodiments, the antibodies are produced by antibody-producing cells deposited with the American Type Culture Collection (10801 University Blvd., Manassas, Va. 20110-2209) on Feb. 16, 2012 and have been assigned Accession No. PTA-12540. In some embodiments, the antibodies, or antigen-binding fragments thereof, have the binding affinity for TEM-1 of the antibodies produced by the deposited antibody-producing cells. In some embodiments, the disclosed antibodies, or antigen-binding fragments thereof, comprise the light and heavy chain CDRs of the antibodies produced by the deposited antibody-producing cells. In some embodiments, the antibodies, or antigen-binding fragments thereof, comprise the light and heavy chain variable regions of the antibodies produced by the deposited antibody-producing cells.

Also disclosed are isolated polynucleotides that encode antibodies or antigen-binding fragments that specifically bind to TEM-1. In some embodiments, the isolated polynucleotides encode an antibody or antigen-binding fragment thereof having a light chain CDR1 sequence substantially the same as, or identical to, SEQ ID NO: 57, for example SEQ ID NO: 137. In some embodiments, the isolated polynucleotides encode an antibody or antigen-binding fragment thereof having a light chain CDR2 substantially the same as, or identical to, SEQ ID NO: 58, for example SEQ ID NO: 138. In some embodiments, the isolated polynucleotides encode an antibody or antigen-binding fragment thereof having a light chain CDR3 substantially the same as, or identical to, SEQ ID NO: 59, for example SEQ ID NO: 139. In some embodiments, the isolated polynucleotides encode an antibody or antigen-binding fragment thereof having a heavy chain CDR1 substantially the same as, or identical to, SEQ ID NO: 61, for example SEQ ID NO: 141. In some embodiments, the isolated polynucleotides encode an antibody or antigen-binding fragment thereof having a heavy chain CDR2 substantially the same as, or identical to, SEQ ID NO: 62, for example SEQ ID NO: 142. In some embodiments, the isolated polynucleotides encode an antibody or antigen-binding fragment thereof having a heavy chain CDR3 substantially the same as, or identical to, SEQ ID NO: 63, for example SEQ ID NO: 143. The isolated polynucleotides may encode an antibody or antigen-binding fragment thereof having a light chain with a CDR1 substantially the same as, or identical to, SEQ ID NO: 57, for example SEQ ID NO: 137; a CDR2 substantially the same as, or identical to, SEQ ID NO: 58, for example SEQ ID NO: 138; and a CDR3 substantially the same as, or identical to, SEQ ID NO: 59, for example SEQ ID NO: 139. The isolated polynucleotides may encode an antibody or antigen-binding fragment thereof having a heavy chain CDR1 substantially the same as, or identical to, SEQ ID NO: 61, for example SEQ ID NO: 141; a CDR2 substantially the same as, or identical to, SEQ ID NO: 62, for example SEQ ID NO: 142; and a CDR3 substantially the same as, or identical to, SEQ ID NO: 63, for example SEQ ID NO: 143. The isolated polynucleotides may encode an antibody or antigen-binding fragment thereof having a light chain CDR1 substantially the same as, or identical to, SEQ ID NO: 57, for example SEQ ID NO: 137; a CDR2 encoded by a nucleotide sequence substantially the same as, or identical to, SEQ ID NO: 58, for example SEQ ID NO: 138; and a CDR3 encoded by a nucleotide sequence substantially the same as, or identical to, SEQ ID NO: 59, for example SEQ ID NO: 139; and a heavy chain CDR1 substantially the same as, or identical to, SEQ ID NO: 61, for example SEQ ID NO: 141; a CDR2 substantially the same as, or identical to, SEQ ID NO: 62, for example SEQ ID NO: 142; and a CDR3 substantially the same as, or identical to, SEQ ID NO: 63, for example SEQ ID NO: 143. Antigen-binding arrangements of CDRs may also be engineered using antibody-like proteins as CDR scaffolding. Such engineered antigen-binding proteins are within the scope of the disclosure.

Polynucleotides described herein may encode antibodies or antigen-binding fragments that have a light chain variable domain segment that includes an amino acid sequence substantially the same as, or identical to, SEQ ID NO: 60, for example SEQ ID NO: 140. In some embodiments the described isolated polynucleotides may encode antibodies or antigen-binding fragments that have a heavy chain variable domain segment that includes an amino acid sequence substantially the same as, or identical to, SEQ ID NO: 64, for example SEQ ID NO: 144. In some embodiments the described isolated polynucleotides may encode antibodies or antigen-binding fragments that have a light chain variable domain segment that includes an amino acid sequence substantially the same as, or identical to, SEQ ID NO: 60, for example SEQ ID NO: 140; and a heavy chain variable domain segment that includes an amino acid sequence substantially the same as, or identical to, SEQ ID NO: 64, for example SEQ ID NO: 144. The isolated polynucleotides capable of encoding the variable domain segments provided herein may be included on the same, or different, vectors to produce antibodies or antigen-binding fragments.

Described herein are isolated antibodies and antigen-binding fragments that specifically bind to TEM-1. In some embodiments, the antibodies or antigen-binding fragments are derived from rat IgG, or derivatives thereof. While the antibodies or antigen-binding fragments may be human, humanized, or chimeric, the antibodies or antigen-binding fragments exemplified herein are derived from rats. In some embodiments, antibodies or antigen-binding fragments may include a light chain CDR1 amino acid sequence substantially the same as, or identical to, SEQ ID NO: 65. In some embodiments, antibodies or antigen-binding fragments may include a light chain CDR2 amino acid sequence substantially the same as, or identical to, SEQ ID NO: 66. In some embodiments, antibodies or antigen-binding fragments may include a light chain CDR3 amino acid sequence substantially the same as, or identical to, SEQ ID NO: 67. In some embodiments, antibodies or antigen-binding fragments may include a heavy chain CDR1 amino acid sequence substantially the same as, or identical to, SEQ ID NO: 69. In some embodiments, antibodies or antigen-binding fragments may include a heavy chain CDR2 amino acid sequence substantially the same as, or identical to, SEQ ID NO: 70. In some embodiments, antibodies or antigen-binding fragments may include a heavy chain CDR3 amino acid sequence substantially the same as, or identical to, SEQ ID NO: 71. The antibodies or antigen-binding fragments may include a light chain having a CDR1 amino acid sequence substantially the same as, or identical to, SEQ ID NO: 65; a CDR2 amino acid sequence substantially the same as, or identical to, SEQ ID NO: 66; and a CDR3 amino acid sequence substantially the same as, or identical to, SEQ ID NO: 67. The antibodies or antigen-binding fragments may include a heavy chain having a CDR1 amino acid sequence substantially the same as, or identical to, SEQ ID NO: 69; a CDR2 amino acid sequence substantially the same as, or identical to, SEQ ID NO: 70; and a CDR3 amino acid sequence substantially the same as, or identical to, SEQ ID NO: 71. The antibodies or antigen-binding fragments may include a light chain having a CDR1 amino acid sequence substantially the same as, or identical to, SEQ ID NO: 65; a CDR2 amino acid sequence substantially the same as, or identical to, SEQ ID NO: 66; and a CDR3 amino acid sequence substantially the same as, or identical to, SEQ ID NO: 67, and also have a heavy chain having a CDR1 amino acid sequence substantially the same as, or identical to, SEQ ID NO: 69; a CDR2 amino acid sequence substantially the same as, or identical to, SEQ ID NO: 70; and a CDR3 amino acid sequence substantially the same as, or identical to, SEQ ID NO: 71.

The described antibodies or antigen-binding fragments may include a light chain variable domain that includes an amino acid sequence substantially the same as, or identical to, SEQ ID NO: 68. In some embodiments, an isolated polynucleotide that includes a sequence substantially the same as, or identical to, SEQ ID NO: 148 may encode this light chain variable domain amino acid sequence. The described antibodies or antigen-binding fragments may include a heavy chain variable domain that includes an amino acid sequence substantially the same as, or identical to, SEQ ID NO: 72. In some embodiments, an isolated polynucleotide that includes a sequence substantially the same as, or identical to, SEQ ID NO: 152 may encode this heavy chain variable domain amino acid sequence. The described antibodies or antigen-binding fragments may include a light and a heavy chain variable domains, wherein the light chain variable domain includes an amino acid sequence substantially the same as, or identical to, SEQ ID NO: 68, and the heavy chain variable domain includes an amino acid sequence substantially the same as, or identical to, SEQ ID NO: 72.

In some embodiments, the antibodies are produced by antibody-producing cells deposited with the American Type Culture Collection (10801 University Blvd., Manassas, Va. 20110-2209) on Feb. 16, 2012 and have been assigned Accession No. PTA-12544. In some embodiments, the antibodies, or antigen-binding fragments thereof, have the binding affinity for TEM-1 of the antibodies produced by the deposited antibody-producing cells. In some embodiments, the disclosed antibodies, or antigen-binding fragments thereof, comprise the light and heavy chain CDRs of the antibodies produced by the deposited antibody-producing cells. In some embodiments, the antibodies, or antigen-binding fragments thereof, comprise the light and heavy chain variable regions of the antibodies produced by the deposited antibody-producing cells.

Also disclosed are isolated polynucleotides that encode antibodies or antigen-binding fragments that specifically bind to TEM-1. In some embodiments, the isolated polynucleotides encode an antibody or antigen-binding fragment thereof having a light chain CDR1 sequence substantially the same as, or identical to, SEQ ID NO: 65, for example SEQ ID NO: 145. In some embodiments, the isolated polynucleotides encode an antibody or antigen-binding fragment thereof having a light chain CDR2 substantially the same as, or identical to, SEQ ID NO: 66, for example SEQ ID NO: 146. In some embodiments, the isolated polynucleotides encode an antibody or antigen-binding fragment thereof having a light chain CDR3 substantially the same as, or identical to, SEQ ID NO: 67, for example SEQ ID NO: 147. In some embodiments, the isolated polynucleotides encode an antibody or antigen-binding fragment thereof having a heavy chain CDR1 substantially the same as, or identical to, SEQ ID NO: 69, for example SEQ ID NO: 149. In some embodiments, the isolated polynucleotides encode an antibody or antigen-binding fragment thereof having a heavy chain CDR2 substantially the same as, or identical to, SEQ ID NO: 70, for example SEQ ID NO: 150. In some embodiments, the isolated polynucleotides encode an antibody or antigen-binding fragment thereof having a heavy chain CDR3 substantially the same as, or identical to, SEQ ID NO: 71, for example SEQ ID NO: 151. The isolated polynucleotides may encode an antibody or antigen-binding fragment thereof having a light chain with a CDR1 substantially the same as, or identical to, SEQ ID NO: 65, for example SEQ ID NO: 145; a CDR2 substantially the same as, or identical to, SEQ ID NO: 66, for example SEQ ID NO: 146; and a CDR3 substantially the same as, or identical to, SEQ ID NO: 67, for example SEQ ID NO: 147. The isolated polynucleotides may encode an antibody or antigen-binding fragment thereof having a heavy chain CDR1 substantially the same as, or identical to, SEQ ID NO: 69, for example SEQ ID NO: 149; a CDR2 substantially the same as, or identical to, SEQ ID NO: 70, for example SEQ ID NO: 150; and a CDR3 substantially the same as, or identical to, SEQ ID NO: 71, for example SEQ ID NO: 151. The isolated polynucleotides may encode an antibody or antigen-binding fragment thereof having a light chain CDR1 substantially the same as, or identical to, SEQ ID NO: 65, for example SEQ ID NO: 145; a CDR2 encoded by a nucleotide sequence substantially the same as, or identical to, SEQ ID NO: 66, for example SEQ ID NO: 146; and a CDR3 encoded by a nucleotide sequence substantially the same as, or identical to, SEQ ID NO: 67, for example SEQ ID NO: 147; and a heavy chain CDR1 substantially the same as, or identical to, SEQ ID NO: 69, for example SEQ ID NO: 149; a CDR2 substantially the same as, or identical to, SEQ ID NO: 70, for example SEQ ID NO: 150; and a CDR3 substantially the same as, or identical to, SEQ ID NO: 71, for example SEQ ID NO: 151. Antigen-binding arrangements of CDRs may also be engineered using antibody-like proteins as CDR scaffolding. Such engineered antigen-binding proteins are within the scope of the disclosure.

Polynucleotides described herein may encode antibodies or antigen-binding fragments that have a light chain variable domain segment that includes an amino acid sequence substantially the same as, or identical to, SEQ ID NO: 68, for example SEQ ID NO: 148. In some embodiments the described isolated polynucleotides may encode antibodies or antigen-binding fragments that have a heavy chain variable domain segment that includes an amino acid sequence substantially the same as, or identical to, SEQ ID NO: 72, for example SEQ ID NO: 152. In some embodiments the described isolated polynucleotides may encode antibodies or antigen-binding fragments that have a light chain variable domain segment that includes an amino acid sequence substantially the same as, or identical to, SEQ ID NO: 68, for example SEQ ID NO: 148; and a heavy chain variable domain segment that includes an amino acid sequence substantially the same as, or identical to, SEQ ID NO: 72, for example SEQ ID NO: 152. The isolated polynucleotides capable of encoding the variable domain segments provided herein may be included on the same, or different, vectors to produce antibodies or antigen-binding fragments.

Described herein are isolated antibodies and antigen-binding fragments that specifically bind to TEM-1. In some embodiments, the antibodies or antigen-binding fragments are derived from rat IgG, or derivatives thereof. While the antibodies or antigen-binding fragments may be human, humanized, or chimeric, the antibodies or antigen-binding fragments exemplified herein are derived from rats. In some embodiments, antibodies or antigen-binding fragments may include a light chain CDR1 amino acid sequence substantially the same as, or identical to, SEQ ID NO: 73. In some embodiments, antibodies or antigen-binding fragments may include a light chain CDR2 amino acid sequence substantially the same as, or identical to, SEQ ID NO: 74. In some embodiments, antibodies or antigen-binding fragments may include a light chain CDR3 amino acid sequence substantially the same as, or identical to, SEQ ID NO: 75. In some embodiments, antibodies or antigen-binding fragments may include a heavy chain CDR1 amino acid sequence substantially the same as, or identical to, SEQ ID NO: 77. In some embodiments, antibodies or antigen-binding fragments may include a heavy chain CDR2 amino acid sequence substantially the same as, or identical to, SEQ ID NO: 78. In some embodiments, antibodies or antigen-binding fragments may include a heavy chain CDR3 amino acid sequence substantially the same as, or identical to, SEQ ID NO: 79. The antibodies or antigen-binding fragments may include a light chain having a CDR1 amino acid sequence substantially the same as, or identical to, SEQ ID NO: 73; a CDR2 amino acid sequence substantially the same as, or identical to, SEQ ID NO: 74; and a CDR3 amino acid sequence substantially the same as, or identical to, SEQ ID NO: 75. The antibodies or antigen-binding fragments may include a heavy chain having a CDR1 amino acid sequence substantially the same as, or identical to, SEQ ID NO: 77; a CDR2 amino acid sequence substantially the same as, or identical to, SEQ ID NO: 78; and a CDR3 amino acid sequence substantially the same as, or identical to, SEQ ID NO: 79. The antibodies or antigen-binding fragments may include a light chain having a CDR1 amino acid sequence substantially the same as, or identical to, SEQ ID NO: 73; a CDR2 amino acid sequence substantially the same as, or identical to, SEQ ID NO: 74; and a CDR3 amino acid sequence substantially the same as, or identical to, SEQ ID NO: 75, and also have a heavy chain having a CDR1 amino acid sequence substantially the same as, or identical to, SEQ ID NO: 77; a CDR2 amino acid sequence substantially the same as, or identical to, SEQ ID NO: 78; and a CDR3 amino acid sequence substantially the same as, or identical to, SEQ ID NO: 79.

The described antibodies or antigen-binding fragments may include a light chain variable domain that includes an amino acid sequence substantially the same as, or identical to, SEQ ID NO: 76. In some embodiments, an isolated polynucleotide that includes a sequence substantially the same as, or identical to, SEQ ID NO: 156 may encode this light chain variable domain amino acid sequence. The described antibodies or antigen-binding fragments may include a heavy chain variable domain that includes an amino acid sequence substantially the same as, or identical to, SEQ ID NO: 80. In some embodiments, an isolated polynucleotide that includes a sequence substantially the same as, or identical to, SEQ ID NO: 160 may encode this heavy chain variable domain amino acid sequence. The described antibodies or antigen-binding fragments may include a light and a heavy chain variable domains, wherein the light chain variable domain includes an amino acid sequence substantially the same as, or identical to, SEQ ID NO: 76, and the heavy chain variable domain includes an amino acid sequence substantially the same as, or identical to, SEQ ID NO: 80.

In some embodiments, the antibodies are produced by antibody-producing cells deposited with the American Type Culture Collection (10801 University Blvd., Manassas, Va. 20110-2209) on Feb. 16, 2012 and have been assigned Accession No. PTA-12547. In some embodiments, the antibodies, or antigen-binding fragments thereof, have the binding affinity for TEM-1 of the antibodies produced by the deposited antibody-producing cells. In some embodiments, the disclosed antibodies, or antigen-binding fragments thereof, comprise the light and heavy chain CDRs of the antibodies produced by the deposited antibody-producing cells. In some embodiments, the antibodies, or antigen-binding fragments thereof, comprise the light and heavy chain variable regions of the antibodies produced by the deposited antibody-producing cells.

Also disclosed are isolated polynucleotides that encode antibodies or antigen-binding fragments that specifically bind to TEM-1. In some embodiments, the isolated polynucleotides encode an antibody or antigen-binding fragment thereof having a light chain CDR1 sequence substantially the same as, or identical to, SEQ ID NO: 73, for example SEQ ID NO: 153. In some embodiments, the isolated polynucleotides encode an antibody or antigen-binding fragment thereof having a light chain CDR2 substantially the same as, or identical to, SEQ ID NO: 74, for example SEQ ID NO: 154. In some embodiments, the isolated polynucleotides encode an antibody or antigen-binding fragment thereof having a light chain CDR3 substantially the same as, or identical to, SEQ ID NO: 75, for example SEQ ID NO: 155. In some embodiments, the isolated polynucleotides encode an antibody or antigen-binding fragment thereof having a heavy chain CDR1 substantially the same as, or identical to, SEQ ID NO: 77, for example SEQ ID NO: 157. In some embodiments, the isolated polynucleotides encode an antibody or antigen-binding fragment thereof having a heavy chain CDR2 substantially the same as, or identical to, SEQ ID NO: 78, for example SEQ ID NO: 158. In some embodiments, the isolated polynucleotides encode an antibody or antigen-binding fragment thereof having a heavy chain CDR3 substantially the same as, or identical to, SEQ ID NO: 79, for example SEQ ID NO: 159. The isolated polynucleotides may encode an antibody or antigen-binding fragment thereof having a light chain with a CDR1 substantially the same as, or identical to, SEQ ID NO: 73, for example SEQ ID NO: 153; a CDR2 substantially the same as, or identical to, SEQ ID NO: 74, for example SEQ ID NO: 154; and a CDR3 substantially the same as, or identical to, SEQ ID NO: 75, for example SEQ ID NO: 155. The isolated polynucleotides may encode an antibody or antigen-binding fragment thereof having a heavy chain CDR1 substantially the same as, or identical to, SEQ ID NO: 77, for example SEQ ID NO: 157; a CDR2 substantially the same as, or identical to, SEQ ID NO: 78, for example SEQ ID NO: 158; and a CDR3 substantially the same as, or identical to, SEQ ID NO: 79, for example SEQ ID NO: 159. The isolated polynucleotides may encode an antibody or antigen-binding fragment thereof having a light chain CDR1 substantially the same as, or identical to, SEQ ID NO: 73, for example SEQ ID NO: 153; a CDR2 encoded by a nucleotide sequence substantially the same as, or identical to, SEQ ID NO: 74, for example SEQ ID NO: 154; and a CDR3 encoded by a nucleotide sequence substantially the same as, or identical to, SEQ ID NO: 75, for example SEQ ID NO: 155; and a heavy chain CDR1 substantially the same as, or identical to, SEQ ID NO: 77, for example SEQ ID NO: 157; a CDR2 substantially the same as, or identical to, SEQ ID NO: 78, for example SEQ ID NO: 158; and a CDR3 substantially the same as, or identical to, SEQ ID NO: 79, for example SEQ ID NO: 159. Antigen-binding arrangements of CDRs may also be engineered using antibody-like proteins as CDR scaffolding. Such engineered antigen-binding proteins are within the scope of the disclosure.

Polynucleotides described herein may encode antibodies or antigen-binding fragments that have a light chain variable domain segment that includes an amino acid sequence substantially the same as, or identical to, SEQ ID NO: 76, for example SEQ ID NO: 156. In some embodiments the described isolated polynucleotides may encode antibodies or antigen-binding fragments that have a heavy chain variable domain segment that includes an amino acid sequence substantially the same as, or identical to, SEQ ID NO: 80, for example SEQ ID NO: 160. In some embodiments the described isolated polynucleotides may encode antibodies or antigen-binding fragments that have a light chain variable domain segment that includes an amino acid sequence substantially the same as, or identical to, SEQ ID NO: 76, for example SEQ ID NO: 156; and a heavy chain variable domain segment that includes an amino acid sequence substantially the same as, or identical to, SEQ ID NO: 80, for example SEQ ID NO: 160. The isolated polynucleotides capable of encoding the variable domain segments provided herein may be included on the same, or different, vectors to produce antibodies or antigen-binding fragments.

Polynucleotides encoding recombinant antigen-binding proteins also are within the scope of the disclosure. In some embodiments, the polynucleotides described (and the peptides they encode) include a leader sequence. Any leader sequence known in the art may be employed. The leader sequence may include, but is not limited to, a restriction site or a translation start site.

The antibodies or antigen-binding fragments described herein include variants having single or multiple amino acid substitutions, deletions, or additions that retain the biological properties (e.g., binding affinity or immune effector activity) of the described antibodies or antigen-binding fragments. The skilled person may produce variants having single or multiple amino acid substitutions, deletions, or additions. These variants may include: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies or antigen-binding fragments described herein may include variants in which amino acid residues from one species are substituted for the corresponding residue in another species, either at the conserved or nonconserved positions. In other embodiments, amino acid residues at nonconserved positions are substituted with conservative or nonconservative residues. The techniques for obtaining these variants, including genetic (deletions, mutations, etc.), chemical, and enzymatic techniques, are known to persons having ordinary skill in the art.

The antibodies or antigen-binding fragments described herein may embody several antibody isotypes, such as IgM, IgD, IgG, IgA and IgE. Antibody or antigen-binding fragment thereof specificity is largely determined by the amino acid sequence, and arrangement, of the CDRs. Therefore, the CDRs of one isotype may be transferred to another isotype without altering antigen specificity. Alternatively, techniques have been established to cause hybridomas to switch from producing one antibody isotype to another (isotype switching) without altering antigen specificity. Accordingly, such antibody isotypes are within the scope of the described antibodies or antigen-binding fragments.

The antibodies or antigen-binding fragments described herein have binding affinities (in M) for TEM-1 that include a dissociation constant ($K_D$) of less than about $1 \times 10^{-8}$ M. In one embodiment the antibody 16D2 has an affinity for TEM-1 of $1.31 \times 10^{-14}$ M. In one embodiment the antibody 7H12 has an affinity for TEM-1 of $2.79 \times 10^{-14}$ M. In one embodiment the antibody 15F8 has an affinity for TEM-1 of $2.22 \times 10^{-13}$ M. In one embodiment the antibody 9A5 has an affinity for TEM-1 of $2.16 \times 10^{-11}$ M. In one embodiment the antibody 11D1 has an affinity for TEM-1 of $2.40 \times 10^{-10}$ M. In one embodiment the antibody 15D10 has an affinity for TEM-1 of $1.06 \times 10^{-10}$ M. In one embodiment the antibody 7D3 has an affinity for TEM-1 of $2.03 \times 10^{-12}$ M. In one embodiment the antibody 16D2 has an affinity for TEM-1 of about $5 \times 10^{-13}$ M to about $5 \times 10^{-14}$ M. In one embodiment the antibody 7H12 has an affinity for TEM-1 of about $8 \times 10^{-13}$ M to about $8 \times 10^{-14}$ M. In one embodiment the antibody 15F8 has an affinity for TEM-1 of about $8 \times 10^{-12}$ M to about $8 \times 10^{-13}$ M. In one embodiment the antibody 9A5 has an affinity for TEM-1 of about $7 \times 10^{-10}$ M to about $7 \times 10^{-11}$ M. In one embodiment the antibody 11D1 has an affinity for TEM-1 of about $7 \times 10^{-9}$ M to about $7 \times 10^{-10}$ M. In one embodiment the antibody 15D10 has an affinity for TEM-1 of about $6 \times 10^{-9}$ M to about $6 \times 10^{-10}$ M. In one embodiment the antibody 7D3 has an affinity for TEM-1 of about $7 \times 10^{-11}$ M to about $7 \times 10^{-12}$ M. The affinity of the described antibodies, or antigen-binding fragments, may be determined by a variety of methods know in the art, such as surface plasmon resonance or ELISA-based methods.

Also provided are vectors comprising the polynucleotides described herein. The vectors can be expression vectors. Recombinant expression vectors containing a sequence encoding a polypeptide of interest are thus contemplated as within the scope of this disclosure. The expression vector may contain one or more additional sequences such as but not limited to regulatory sequences (e.g., promoter, enhancer), a selection marker, and a polyadenylation signal. Vectors for transforming a wide variety of host cells are well known and include, but are not limited to, plasmids, phagemids, cosmids, baculoviruses, bacmids, bacterial artificial chromosomes (BACs), yeast artificial chromosomes (YACs), as well as other bacterial, yeast and viral vectors.

Recombinant expression vectors within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated.

The transcriptional and translational control sequences in expression vectors to be used in transforming vertebrate cells may be provided by viral sources. Exemplary vectors may be constructed as described by Okayama and Berg, 3 Mol. Cell. Biol. 280 (1983).

In some embodiments, the antibody- or antigen-binding fragment-coding sequence is placed under control of a powerful constitutive promoter, such as the promoters for the following genes: hypoxanthine phosphoribosyl transferase (HPRT), adenosine deaminase, pyruvate kinase, beta-actin, human myosin, human hemoglobin, human muscle creatine, and others. In addition, many viral promoters function constitutively in eukaryotic cells and are suitable for use with the described embodiments. Such viral promoters include without limitation, Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus. In one embodiment, the antibody or antigen-binding fragment thereof coding sequence is placed under control of an inducible promoter such as the metallothionein promoter, tetracycline-inducible promoter, doxycycline-inducible promoter, promoters that contain one or more interferon-stimulated response elements (ISRE) such as protein kinase R 2',5'-oligoadenylate synthetases, Mx genes, ADAR1, and the like.

Vectors described herein may contain one or more Internal Ribosome Entry Site(s) (IRES). Inclusion of an IRES sequence into fusion vectors may be beneficial for enhancing expression of some proteins. In some embodiments the vector system will include one or more polyadenylation sites (e.g., SV40), which may be upstream or downstream of any of the aforementioned nucleic acid sequences. Vector components may be contiguously linked, or arranged in a manner that provides optimal spacing for expressing the gene products (i.e., by the introduction of "spacer" nucleotides between the ORFs), or positioned in another way. Regulatory elements, such as the IRES motif, may also be arranged to provide optimal spacing for expression.

The vectors may comprise selection markers, which are well known in the art. Selection markers include positive and negative selection markers, for example, antibiotic resistance genes (e.g., neomycin resistance gene, a hygromycin resistance gene, a kanamycin resistance gene, a tetracycline resistance gene, a penicillin resistance gene), glutamate synthase genes, HSV-TK, HSV-TK derivatives for ganciclovir selection, or bacterial purine nucleoside phosphorylase gene for 6-methylpurine selection (Gadi et al., 7 Gene Ther. 1738-1743 (2000)). A nucleic acid sequence encoding a selection marker or the cloning site may be upstream or downstream of a nucleic acid sequence encoding a polypeptide of interest or cloning site.

The vectors described herein may be used to transform various cells with the genes encoding the described antibodies or antigen-binding fragments. For example, the vectors may be used to generate antibody or antigen-binding fragment-producing cells. Thus, another aspect features host cells transformed with vectors comprising a nucleic acid sequence encoding an antibody or antigen-binding fragment thereof that specifically binds TEM-1, such as the antibodies or antigen-binding fragments described and exemplified herein.

Numerous techniques are known in the art for the introduction of foreign genes into cells and may be used to construct the recombinant cells for purposes of carrying out the described methods, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline, 29 Pharmac. Ther. 69-92 (1985)). Calcium phosphate precipitation and polyethylene glycol (PEG)-induced fusion of bacterial protoplasts with mammalian cells may also be used to transform cells.

Cells suitable for use in the expression of the antibodies or antigen-binding fragments described herein are preferably eukaryotic cells, more preferably cells of plant, rodent, or human origin, for example but not limited to NSO, CHO, CHOK1, perC.6, Tk-ts13, BHK, HEK293 cells, COS-7, T98G, CV-1/EBNA, L cells, C127, 3T3, HeLa, NS1, Sp2/0 myeloma cells, and BHK cell lines, among others. In addition, expression of antibodies may be accomplished using hybridoma cells. Methods for producing hybridomas are well established in the art.

Cells transformed with expression vectors described herein may be selected or screened for recombinant expression of the antibodies or antigen-binding fragments described herein. Recombinant-positive cells are expanded and screened for subclones exhibiting a desired phenotype, such as high level expression, enhanced growth properties, or the ability to yield proteins with desired biochemical characteristics, for example, due to protein modification or altered post-translational modifications. These phenotypes may be due to inherent properties of a given subclone or to mutation. Mutations may be effected through the use of chemicals, UV-wavelength light, radiation, viruses, insertional mutagens, inhibition of DNA mismatch repair, or a combination of such methods.

Methods of Detecting TEM-1

Provided herein are methods for detecting TEM-1 in a biological sample by contacting the sample with an antibody, or antigen-binding fragment thereof, described herein. As described herein, the sample may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments the described methods include detecting TEM-1 in a biological sample by contacting the sample with:

(a) any one of antibody 14G3, antibody 9A5, antibody 7D3, antibody 7H12, antibody 9G5, antibody 10H8, antibody 11D1, antibody 15D10, antibody 15F8, antibody 16D2, or an antigen-binding fragment thereof;

(b) an antibody, or antigen-binding fragment thereof, that comprises heavy chain CDR1, CDR2, and CDR3 amino acid sequences and light chain CDR1, CDR2, and CDR3 amino acid sequences of any one of antibody 14G3, antibody 9A5, antibody 7D3, antibody 7H12, antibody 9G5, antibody 10H8, antibody 11D1, antibody 15D10, antibody 15F8, or antibody 16D2, as described in Table 2;

(c) an antibody, or antigen-binding fragment thereof, that comprises the heavy chain variable domain segment and light chain variable domain segment of any one of antibody 14G3, antibody 9A5, antibody 7D3, antibody 7H12, antibody 9G5, antibody 10H8, antibody 11D1, antibody 15D10, antibody 15F8, or antibody 16D2, as described in Table 2; or (d) an antibody having the amino acid sequence of antibody produced by any one of the cell lines deposited with the ATCC having accession number PTA-12538, PTA-12545, PTA-12542, PTA-12546, PTA-12541, PTA-12539, PTA-12543, PTA-12540, PTA-12544, or PTA-12547 or an antigen-binding fragment thereof.

In some embodiments the sample may be contacted with more than one of the antibodies or antigen-binding fragments described herein. For example, a sample may be contacted with a first antibody, or antigen-binding fragment thereof, and then contacted with a second antibody, or antigen-binding fragment thereof, wherein the first antibody or antigen-binding fragment and the second antibody or antigen-binding fragment are not the same antibody or antigen-binding fragment. In some embodiments, the first antibody, or antigen-binding fragment thereof, may be affixed to a surface, such as a multiwell plate, chip, or similar substrate prior to contacting the sample. In other embodiments the first antibody, or antigen-binding fragment thereof, may not be affixed, or attached, to anything at all prior to contacting the sample.

Various combinations of the antibodies, or antigen-binding fragments thereof, may be used to detect TEM-1 in a biological sample, as described in Table 4. In addition to MORAb-004 serving as one of two antibodies in a TEM-1 binding assay, as shown in Table 4, many of the combinations not involving MORAb-004 provided in Table 4 may be used in the presence of MORAb-004, because these antibodies do not compete with MORAb-004 for binding to TEM-1. For example, the combination of antibodies 9G5 and 15F8 may be used to detect, and quantify, TEM-1 in the presence of MORAb-004, because these antibodies do not compete with MORAb-004 for binding to TEM-1.

TABLE 4

Antibody combinations for detecting TEM-1 (in this table MORAb-004 is abbreviated as "M-004").

| | | FIRST ANTIBODY | | | | | | | | |
|---|---|---|---|---|---|---|---|---|---|---|
| | 14G3 | 9A5 | 7D3 | 7H12 | 9G5 | 10H8 | 11D1 | 15D10 | 15F8 | 16D2 |
| SECOND ANTIBODY | M-004 | 14G3 | 14G3 | 14G3 | 14G3 | 14G3 | 14G3 | 14G3 | 14G3 | 14G3 |
| | 9A5 | M-004 | 9A5 | 9A5 | 9A5 | 9A5 | 9A5 | 9A5 | 9A5 | 9A5 |
| | 7D3 | 7D3 | M-004 | 7D3 | 7D3 | 7D3 | 7D3 | 7D3 | 7D3 | 7D3 |
| | 7H12 | 7H12 | 7H12 | M-004 | 7H12 | 7H12 | 7H12 | 7H12 | 7H12 | 7H12 |

TABLE 4-continued

Antibody combinations for detecting TEM-1 (in this table MORAb-004 is abbreviated as "M-004").

| FIRST ANTIBODY | | | | | | | | | |
|---|---|---|---|---|---|---|---|---|---|
| 14G3 | 9A5 | 7D3 | 7H12 | 9G5 | 10H8 | 11D1 | 15D10 | 15F8 | 16D2 |
| 9G5 | 9G5 | 9G5 | 9G5 | M-004 | 9G5 | 9G5 | 9G5 | 9G5 | 9G5 |
| 10H8 | 10H8 | 10H8 | 10H8 | 10H8 | M-004 | 10H8 | 10H8 | 10H8 | 10H8 |
| 11D1 | 11D1 | 11D1 | 11D1 | 11D1 | 11D1 | M-004 | 11D1 | 11D1 | 11D1 |
| 15D10 | 15D10 | 15D10 | 15D10 | 15D10 | 15D10 | 15D10 | M-004 | 15D10 | 15D10 |
| 15F8 | 15F8 | 15F8 | 15F8 | 15F8 | 15F8 | 15F8 | 15F8 | M-004 | 15F8 |
| 16D2 | 16D2 | 16D2 | 16D2 | 16D2 | 16D2 | 16D2 | 16D2 | 16D2 | M-004 |

The described antibodies and antigen-binding fragments may be detectably labeled. In some embodiments labeled antibodies and antigen-binding fragments may facilitate the detection TEM-1 via the methods described herein. Many such labels are readily known to those skilled in the art. For example, suitable labels include, but should not be considered limited to, radiolabels, fluorescent labels, epitope tags, biotin, chromophore labels, ECL labels, or enzymes. More specifically, the described labels include ruthenium, $^{111}$In-DOTA, $^{111}$In-diethylenetriaminepentaacetic acid (DTPA), horseradish peroxidase, alkaline phosphatase and beta-galactosidase, poly-histidine (HIS tag), acridine dyes, cyanine dyes, fluorone dyes, oxazin dyes, phenanthridine dyes, rhodamine dyes, Alexafluor® dyes, and the like.

The described antibodies and antigen-binding fragments may be used in a variety of assays to detect TEM-1 in a biological sample. Some suitable assays include, but should not be considered limited to, western blot analysis, radioimmunoassay, surface plasmon resonance, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

In some embodiments described herein detection of TEM-1-expressing cancer cells in a subject may be used to determine that the subject may be treated with a therapeutic agent directed against TEM-1.

TEM-1 is present at detectable levels in blood and serum samples. Thus, provided herein are methods for detecting TEM-1 in a sample derived from blood, such as a serum sample, by contacting the sample with an antibody, or antigen-binding fragment thereof, or ligand that specifically binds TEM-1. The blood sample, or a derivative thereof, may be diluted, fractionated, or otherwise processed to yield a sample upon which the described method may be performed. In some embodiments, TEM-1 may be detected in a blood sample, or a derivative thereof, by any number of assays known in the art, such as, but not limited to, western blot analysis, radioimmunoassay, surface plasmon resonance, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

Methods for Diagnosing Cancer

Provided herein are methods for diagnosing TEM-1-expressing cancer in a subject. In some embodiments TEM-1-expressing cancer includes melanoma, sarcoma, bladder cancer, gastric cancer, hepatocellular cancer, or colon cancer. In some embodiments, as described above, detecting TEM-1 in a biological sample, such as a blood sample or a serum sample, provides the ability to diagnose cancer in the subject from whom the sample was obtained. Alternatively, in some embodiments other samples such as a histological sample, a fine needle aspirate sample, resected tumor tissue, circulating cells, circulating tumor cells, and the like, may also be used to assess whether the subject from whom the sample was obtained has cancer. In some embodiments, it may already be known that the subject from whom the sample was obtained has cancer, but the type of cancer afflicting the subject may not yet have been diagnosed or a preliminary diagnosis may be unclear, thus detecting TEM-1 in a biological sample obtained from the subject can allow for, or clarify, diagnosis of the cancer. For example, a subject may be known to have cancer, but it may not be known, or may be unclear, whether the subject's cancer is TEM-1-expressing.

In some embodiments the described methods involve assessing whether a subject is afflicted with TEM-1-expressing cancer by determining the amount of TEM-1 that is present in a biological sample derived from the subject; and comparing the observed amount of TEM-1 with the amount of TEM-1 in a control, or reference, sample, wherein a difference between the amount of TEM-1 in the sample derived from the subject and the amount of TEM-1 in the control, or reference, sample is an indication that the subject is afflicted with a TEM-1-expressing cancer. In another embodiment the amount of TEM-1 observed in a biological sample obtained from a subject may be compared to levels of TEM-1 known to be associated with certain forms or stages of cancer, to determine the form or stage of the subject's cancer. In some embodiments the amount of TEM-1 in the sample derived from the subject is assessed by contacting the sample with an antibody, or an antigen-binding fragment thereof, that specifically binds TEM-1, such as the antibodies described herein. The sample assessed for the presence of TEM-1 may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments TEM-1-expressing cancer includes melanoma, sarcoma, bladder cancer, gastric cancer, hepatocellular cancer, or colon cancer. In some embodiments the subject is a human.

In some embodiments the method of diagnosing a TEM-1-expressing cancer will involve: contacting a biological sample of a subject with a TEM-1-specific antibody, or an antigen-binding fragment thereof (such as those derivable from the antibodies and fragments provided in Table 2), quantifying the amount of TEM-1 present in the sample that is bound by the antibody or antigen-binding fragment thereof, comparing the amount of TEM-1 present in the sample to a known standard or reference sample; and determining whether the subject's TEM-1 levels fall within the levels of TEM-1 associated with cancer. In an additional embodiment, the diagnostic method can be followed with an additional step of administering or prescribing a cancer-specific treatment. In another embodiment, the diagnostic method can be followed with an additional step of transmitting the results of the determination to facilitate treatment of the cancer. In some embodiments the cancer-specific treatment may be directed against TEM-1-expressing cancers, such as MORAb-004.

In some embodiments the described methods involve assessing whether a subject is afflicted with TEM-1-expressing cancer by determining the amount of TEM-1 present in a blood or serum sample obtained from the subject; and comparing the observed amount of TEM-1 with the amount of TEM-1 in a control, or reference, sample, wherein a difference between the amount of TEM-1 in the sample derived from the subject and the amount of TEM-1 in the control, or reference, sample is an indication that the subject is afflicted with a TEM-1-expressing cancer.

In some embodiments the control, or reference, sample may be derived from a subject that is not afflicted with TEM-1-expressing cancer. In some embodiments the control, or reference, sample may be derived from a subject that is afflicted with TEM-1-expressing cancer. In some embodiments where the control, or reference, sample is derived from a subject that is not afflicted with TEM-1-expressing cancer, an observed increase in the amount of TEM-1 present in the test sample, relative to that observed for the control or reference sample, is an indication that the subject being assessed is afflicted with TEM-1-expressing cancer. In some embodiments where the control sample is derived from a subject that is not afflicted with TEM-1-expressing cancer, an observed decrease or similarity in the amount of TEM-1 present in the test sample, relative to that observed for the control or reference sample, is an indication that the subject being assessed is not afflicted with TEM-1-expressing cancer. In some embodiments where the control or reference sample is derived from a subject that is afflicted with TEM-1-expressing cancer, an observed similarity in the amount of TEM-1 present in the test sample, relative to that observed for the control or reference sample, is an indication that the subject being assessed is afflicted with TEM-1-expressing cancer. In some embodiments where the control or reference sample is derived from a subject that is afflicted with TEM-1-expressing cancer, an observed decrease in the amount of TEM-1 present in the test sample, relative to that observed for the control or reference sample, is an indication that the subject being assessed is not afflicted with TEM-1-expressing cancer.

In some embodiments the amount of TEM-1 in the sample derived from the subject is assessed by contacting the sample with an antibody, or an antigen-binding fragment thereof, that specifically binds TEM-1, such as the antibodies described herein. The sample assessed for the presence of TEM-1 may be derived from a blood sample, a serum sample, circulating cells, circulating tumor cells, cells that are not tissue associated (i.e., free cells), tissues (e.g., surgically resected tumor tissue, biopsies, including fine needle aspiration), histological preparations, and the like.

In various aspects, the amount of TEM-1 is determined by contacting the sample with an antibody, or antigen-binding fragment thereof, that specifically binds TEM-1. In some embodiments, the sample may be contacted by more than one type of antibody, or antigen-binding fragment thereof, that specifically binds TEM-1. In some embodiments, the sample may be contacted by a first antibody, or antigen-binding fragment thereof, that specifically binds TEM-1 and then contacted by a second antibody, or antigen-binding fragment thereof, that specifically binds TEM-1. Antibodies such as those described herein may be used in this capacity. For example, the antibody is selected from the group consisting of:

(a) any one of antibody 14G3, antibody 9A5, antibody 7D3, antibody 7H12, antibody 9G5, antibody 10H8, antibody 11D1, antibody 15D10, antibody 15F8, antibody 16D2, or an antigen-binding fragment thereof;

(b) an antibody, or antigen-binding fragment thereof, that comprises heavy chain CDR1, CDR2, and CDR3 amino acid sequences and light chain CDR1, CDR2, and CDR3 amino acid sequences of any one of antibody 14G3, antibody 9A5, antibody 7D3, antibody 7H12, antibody 9G5, antibody 10H8, antibody 11D1, antibody 15D10, antibody 15F8, or antibody 16D2, as described in Table 2;

(c) an antibody, or antigen-binding fragment thereof, that comprises the heavy chain variable domain segment and light chain variable domain segment of any one of antibody 14G3, antibody 9A5, antibody 7D3, antibody 7H12, antibody 9G5, antibody 10H8, antibody 11D1, antibody 15D10, antibody 15F8, or antibody 16D2, as described in Table 2; or (d) an antibody having the amino acid sequence of antibody produced by any one of the cell lines deposited with the ATCC having accession PTA-12538, PTA-12545, PTA-12542, PTA-12546, PTA-12541, PTA-12539, PTA-12543, PTA-12540, PTA-12544, or PTA-12547, or an antigen-binding fragment thereof.

Various combinations of the antibodies and antigen-binding fragments, as described in Table 4, can be used to provide a "first" and "second" antibody or antigen-binding fragment to carry out the described diagnostic methods. In some embodiments TEM-1-expressing cancer includes melanoma, sarcoma, bladder cancer, gastric cancer, hepatocellular cancer, or colon cancer.

In certain embodiments, the amount of TEM-1 is determined by western blot analysis, radioimmunoassay, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

In various embodiments of the described diagnostic methods a control or reference sample is used. This sample may be a positive or negative assay control that ensures the assay used is working properly; for example, an assay control of this nature might be commonly used for immunohistochemistry assays. Alternatively, the sample may be a standardized reference for the amount of TEM-1 in a biological sample from a healthy subject. In some embodiments, the observed TEM-1 levels of the tested subject may be compared with TEM-1 levels observed in samples from subjects known to have TEM-1-expressing cancer. In some embodiments, the control subject may be afflicted with a particular cancer of interest. In some embodiments, the control subject is known to have early stage cancer, which may or may not be TEM-1-expressing cancer. In some embodiments, the control subject is known to have intermediate stage cancer, which may or may not be TEM-1-expressing cancer. In some embodiments, the control subject is known to have late stage, which may or may not be TEM-1-expressing cancer.

Methods for Monitoring Cancer

Provided herein are methods for monitoring TEM-1-expressing cancer in a subject. In some embodiments TEM-1-expressing cancer includes melanoma, sarcoma, bladder cancer, gastric cancer, hepatocellular cancer, or colon cancer. In some embodiments the described methods involve assessing whether TEM-1-expressing cancer is progressing, regressing, or remaining stable by determining the amount of TEM-1 that is present in a test sample derived from the subject; and comparing the observed amount of TEM-1 with the amount of TEM-1 in a biological sample obtained, in a similar manner, from the subject at an earlier point in time, wherein a difference between the amount of TEM-1 in the test sample and the earlier sample provides an indication of whether the cancer is progressing, regressing, or remaining stable. In this regard, a test sample with an increased amount of TEM-1, relative to the amount observed for the earlier sample, may indicate progression of a TEM-1-expressing cancer. Conversely, a test sample with a decreased amount of TEM-1, relative to the amount observed for the earlier sample, may indicate regression of a TEM-1-expressing cancer. Accordingly, a test sample with an insignificant difference in the amount of TEM-1, relative to the amount observed for the earlier sample, may indicate a state of stable disease for a TEM-1-expressing cancer. In some embodiments the amount of TEM-1 in a biological sample derived from the subject is assessed by contacting the sample with an antibody, or an antibody fragment thereof, that specifically binds TEM-1, such as the antibodies described herein. The sample assessed for the presence of TEM-1 may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments the subject is a human.

In some embodiments the methods of monitoring a TEM-1-expressing cancer will involve: contacting a biological sample of a subject with a TEM-1-specific antibody, or antigen-binding fragment thereof (such as those derivable from the antibodies and fragments provided in Table 2), quantifying the amount of TEM-1 present in the sample, comparing the amount of TEM-1 present in the sample to the amount of TEM-1 determined to be in a biological sample obtained, in a similar manner, from the same subject at an earlier point in time; and determining whether the subject's TEM-1 levels have changed over time. A test sample with an increased amount of TEM-1, relative to the amount observed for the earlier sample, may indicate progression of cancer. Conversely, a test sample with a decreased amount of TEM-1, relative to the amount observed for the earlier sample, may indicate regression of a TEM-1-expressing cancer. Accordingly, a test sample with an insignificant difference in the amount of TEM-1, relative to the amount observed for the earlier sample, may indicate a state of stable disease for a TEM-1-expressing cancer. In some embodiments, the TEM-1 levels of the sample may be compared to a known standard or a reference sample, alone or in addition to the TEM-1 levels observed for a sample assessed at an earlier point in time. In an additional embodiment, the diagnostic method can be followed with an additional step of administering a cancer-specific treatment. In some embodiments the cancer-specific treatment may be directed against TEM-1-expressing cancers, such as MORAb-004.

In various aspects, the amount of TEM-1 is determined by contacting the sample with an antibody, or antigen-binding fragment thereof, that specifically binds TEM-1. In some embodiments, the sample may be contacted by more than one type of antibody, or antigen-binding fragment thereof, that specifically binds TEM-1. In some embodiments, the sample may be contacted by a first antibody, or antigen-binding fragment thereof, that specifically binds TEM-1 and then contacted by a second antibody, or antigen-binding fragment thereof, that specifically binds TEM-1. Antibodies such as those described herein may be used in this capacity. For example, the antibody may be selected from among:

(a) any one of antibody 14G3, antibody 9A5, antibody 7D3, antibody 7H12, antibody 9G5, antibody 10H8, antibody 11D1, antibody 15D10, antibody 15F8, antibody 16D2, or an antigen-binding fragment thereof;

(b) an antibody, or antigen-binding fragment thereof, that comprises heavy chain CDR1, CDR2, and CDR3 amino acid sequences and light chain CDR1, CDR2, and CDR3 amino acid sequences of any one of antibody 14G3, antibody 9A5, antibody 7D3, antibody 7H12, antibody 9G5, antibody 10H8, antibody 11D1, antibody 15D10, antibody 15F8, or antibody 16D2, as described in Table 2;

(c) an antibody, or antigen-binding fragment thereof, that comprises the heavy chain variable domain segment and light chain variable domain segment of any one of antibody 14G3, antibody 9A5, antibody 7D3, antibody 7H12, antibody 9G5, antibody 10H8, antibody 11D1, antibody 15D10, antibody 15F8, or antibody 16D2, as described in Table 2; or (d) an antibody having the amino acid sequence of antibody produced by any one of the cell lines deposited with the ATCC having accession number PTA-12538, PTA-12545, PTA-12542, PTA-12546, PTA-12541, PTA-12539, PTA-12543, PTA-12540, PTA-12544, or PTA-12547, or an antigen binding fragment thereof.

Various combinations of the antibodies and antigen-binding fragments described in (a)-(d), as detailed in Table 4, can be used to provide a "first" and "second" antibody or antigen-binding fragment to carry out the described monitoring methods. In some embodiments TEM-1-expressing cancer includes melanoma, sarcoma, bladder cancer, gastric cancer, hepatocellular cancer, or colon cancer.

In certain embodiments, the amount of TEM-1 is determined by western blot analysis, radioimmunoassay, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

Kits for Detecting the TEM-1

Provided herein are kits for detecting TEM-1 in a biological sample. These kits include one or more of the TEM-1-specific antibodies described herein, or an antigen-binding fragment thereof, and instructions for use of the kit. In some embodiments the antibody, or antigen-binding fragment, provided in the described kits may be one or more of:

(a) any one of antibody 14G3, antibody 9A5, antibody 7D3, antibody 7H12, antibody 9G5, antibody 10H8, antibody 11D1, antibody 15D10, antibody 15F8, antibody 16D2, or an antigen-binding fragment thereof;

(b) an antibody, or antigen-binding fragment thereof, that comprises heavy chain CDR1, CDR2, and CDR3 amino acid sequences and light chain CDR1, CDR2, and CDR3 amino acid sequences of any one of antibody 14G3, antibody 9A5, antibody 7D3, antibody 7H12, antibody 9G5, antibody 10H8, antibody 11D1, antibody 15D10, antibody 15F8, or antibody 16D2, as described in Table 2;

(c) an antibody, or antigen-binding fragment thereof, that comprises the heavy chain variable domain segment and light chain variable domain segment of any one of antibody 14G3, antibody 9A5, antibody 7D3, antibody 7H12, antibody 9G5, antibody 10H8, antibody 11D1, antibody 15D10, antibody 15F8, or antibody 16D2, as described in Table 2; or (d) an antibody having the amino acid sequence of antibody produced by any one of the cell lines deposited with the ATCC having accession number PTA-12538, PTA-12545, PTA-12542, PTA-12546, PTA-12541, PTA-12539, PTA-12543, PTA-12540, PTA-12544, or PTA-12547, or an antigen-binding fragment thereof.

The provided antibody, or antigen-binding fragment, may be in solution; lyophilized; affixed to a substrate, carrier, or plate; or detectably labeled.

The described kits may also include additional components useful for performing the methods described herein. By way of example, the kits may comprise means for obtaining a sample from a subject, a control or reference sample, e.g., a sample from a subject having slowly progressing cancer and/or a subject not having cancer, one or more sample compartments, and/or instructional material which describes performance of a method of the invention and tissue specific controls or standards.

The means for determining the level of TEM-1 can further include, for example, buffers or other reagents for use in an assay for determining the level of TEM-1. The instructions can be, for example, printed instructions for performing the assay and/or instructions for evaluating the level of expression of TEM-1.

The described kits may also include means for isolating a sample from a subject. These means can comprise one or more items of equipment or reagents that can be used to obtain a fluid or tissue from a subject. The means for obtaining a sample from a subject may also comprise means for isolating blood components, such as serum, from a blood sample. Preferably, the kit is designed for use with a human subject.

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

Example 1

Generation of Monoclonal Antibodies that Selectively Bind TEM-1

To generate antibodies that specifically bind TEM-1, three eight-week old female Lewis rats were immunized with a recombinant version of TEM-1 fused to the Fc portion of a murine γ heavy chain (rTEM-1-Fc) (Tomkowicz, et al., PNAS 104(46):17965-70 (2007)). On day zero rats were immunized intraperitoneally with 100 µg of rTEM-1-Fc prepared as a 1:1 (v:v) mix with complete Freund's adjuvant (Rockland Immunochemicals, Inc., Gilbertsville, Pa.). Immunized rats were boosted with intraperitoneal injections of 50 µg rTEM-1-Fc mixed 1:1 (v:v) with incomplete Freund's adjuvant (Rockland Immunochemicals Inc.) on day 14 and every 21 days thereafter. Test bleeds were collected on day 24 and every 21 days thereafter and analyzed by direct enzyme-linked immunoassay (EIA) against rTEM-1-His6. Spleens were harvested from animals exhibiting the highest antigen-specific titers and hybridomas were prepared by electrofusion (Hybrimune™ Model CEEF-50B Waveform Generator; Cellectis, Romainville, France) of splenocytes with Sp2/0 Ag14 myeloma cells (ATCC, Rockville, Md.).

Hybridoma supernatants were rescreened by EIA against rTEM-1-His6 or recombinant mesothelin protein as a negative control, to identify hybridomas producing anti-rTEM-1 antibodies. Briefly, 96-well plates were coated with 100 µL/well of a PBS solution containing 1 µg/mL rTEM-1-His6 overnight at 4° C. Wells were then washed and blocked with 3% (w/v) fish gel in PBS for 1 hr at RT. Next, 100 µL of a 3-fold dilution series of hybridoma culture supernatant was added to the wells and plates were incubated at RT for 1 hr. After washing 3 times with PBS containing 0.2% (v/v) Tween-20 (PBST), 100 µL of horseradish peroxidase-conjugated mouse anti-rat IgG (1:2500 dilution; Rockland Immunochemicals, Inc.) was added and plates were incubated for 30 min at 37° C. After washing with PBST, 100 µL of substrate (TMBE-100; Rockland Immunochemicals, Inc.) was added and the reaction stopped after 30 minutes by addition of 100 µL of 1M HCl. Plates were read at 450 nm on a Benchmark microplate reader (BioRad, Concord, Calif.). Selected parental cell lines were then subcloned by limiting dilution and re-assayed against rTEM-1 by EIA. Isotyping of selected clones was performed using the Clonetyping System (SouthernBiotech, Birmingham, Ala.).

Selected hybridoma cell lines (Table 5) were tested for mycoplasma using the mycoplasma PCR ELISA (Roche, Mannheim, Germany) Monoclonal antibodies (mABs) were produced from mycoplasma negative cells grown in 1 L roller bottle cultures. After seeding at $0.5 \times 10^5$ cells/mL, cultures were grown for 21 days in serum free medium (Invitrogen) and 5% low IgG fetal bovine serum (Gibco). At termination, culture supernatants were concentrated approximately 10-fold through a 50 kDa filtration membrane (SpectrumLabs, Rancho Dominguez, Calif.) and mAbs were purified by affinity chromatography, eluted and subsequently dialyzed against PBS using a 12-14 kDa membranous tubing (SpectrumLabs, Rancho Dominguez Calif.), sterile filtered using 0.22 µm Express™PLUS Stericups (Millipore, Billerica Mass.), aliquotted and stored at −80° C.

TABLE 5

Selected hybridoma cell lines that produce TEM-1-specific antibodies

| Cell Line | Isotype | ATCC accession number |
|---|---|---|
| 7D3.F5.E8.D8 | IgG2a/κ | PTA-12538 |
| 7H12.H5.E7 | IgG1/κ | PTA-12545 |
| 9A5.G12.B10.F8.F6 | IgG2a/κ | PTA-12542 |
| 9G5.F2.C1.F4 | IgG1/κ | PTA-12547 |
| 10H8.D7.E3 | IgG2a/κ | PTA-12546 |
| 11D1.G10.F8 | IgG2a/κ | PTA-12541 |
| 14G3.H4.F11.H7 | IgG2a/κ | PTA-12539 |
| 15D10.G4.C12 | IgG2a/κ | PTA-12543 |
| 15F8.G6.B4 | IgG2a/κ | PTA-12540 |
| 16D2.H12.E7.G9 | IgG2a/κ | PTA-12544 |

Example 2

Characterization of Monoclonal Antibodies that Selectively Bind TEM-1

Following production and isolation of the TEM-1-specific antibodies described in Example 1, experiments were performed to determine the binding characteristics of the antibodies. Initially, Western blot analyses were performed using reduced and denatured cell lysates from either aortic smooth muscle cells ("S") (Invitrogen), which are known to express TEM-1, or human umbilical vein endothelial cells (HUVEC) ("H") (ScienCell), which do not express TEM-1. Briefly, aortic smooth muscle cells and HUVECs were lysed in 1.1% OBG buffer (50 mM Tris-HCl, ph 7.5, 150 mM NaCl, 1.1% OBG) supplemented with Complete™ Mini Protease Inhibitor Cocktail (Roche Diagnostics)+PMSF (100 nM) for 15 minutes on ice, then centrifuged at 13,000×g for 15 minutes to remove cellular debris. Equal amounts of total protein (30 µg) were added to NuPAGE sample buffer (Invitrogen) containing 5% B-mercaptoethanol+20 mM DTT. Proteins were separated using SDS-polyacrylamide gel electrophoresis (SDS-PAGE) on a 4-12% Bis-Tris gel (Invitrogen) and transferred to PVDF membrane. Immunoblotting was conducted using the described rat TEM-1-specific antibodies overnight at 4 degrees Celsius, which were then detected with a goat anti-rat-HRP conjugated antibody (Jackson Immunoresearch) and visualized using SuperSignal® West Pico chemiluminescent substrate (Pierce). Signal was visualized using the Omega 12iC molecular imaging system (Ultra-Lum). As shown in FIG. 1, the majority of the tested antibodies were able to detect reduced and denatured TEM-1, indicating that these antibodies recognize an epitope of the protein that is not conformation-dependent.

FACS analyses were also performed using aortic smooth muscle cells (AoSMC) and HUVEC cells. Cells were harvested using cell dissociation buffer (Invitrogen, #13151-014), washed twice in PBS and re-suspended at 50,000 cells/100 µL FACS buffer (PBS+2% FBS) in a round bottom 96 well plate. Cells were incubated for 1 hour on ice with the described rat TEM-1-specific antibodies at a concentration of 10 µg/mL, washed and then incubated with FITC-conjugated goat-anti-rat secondary antibodies (dilution 1:100) (Southern Biotech). Prior to analysis, cells were labeled with 7-AAD (BD Biosciences) to allow for the exclusion of nonviable cells. Cells were analyzed on an EasyCyte Flow Cytometer (Guava Technologies). The data in Table 6 indicate that all of the tested antibodies bind TEM-1 in a native state.

TABLE 6

Results of FACS analysis of TEM-1-specific rat antibodies

| | Geometric mean of resulting FACS plot | | | |
|---|---|---|---|---|
| Primary Antibody | Cells only (no antibody) | AoSMC + primary antibody | HUVEC + primary antibody | Secondary antibody only |
| MORAb-004 | 2.5 | 102.9 | 8.5 | 3.9 |
| 14G3 | 2.5 | 94.2 | 7.0 | 3.5 |
| 9A5 | 2.5 | 89.9 | 7.2 | 3.5 |
| 7D3 | 2.5 | 63.4 | 7.3 | 3.5 |
| 7H12 | 2.5 | 59.9 | 6.1 | 3.5 |
| 9G5 | 2.5 | 57.4 | 6.5 | 3.5 |
| 10H8 | 2.5 | 52.7 | 6.7 | 3.5 |
| 11D1 | 2.5 | 46.3 | 7.1 | 3.5 |
| 15D10 | 2.5 | 86.4 | 6.2 | 3.5 |
| 15F8 | 2.5 | 72.5 | 6.3 | 3.5 |
| 16D2 | 2.5 | 98.0 | 6.9 | 3.5 |

Biacore analyses were also performed to determine the affinity of selected isolated TEM-1-specific rat antibodies. For these studies streptavidin-coated sensor surfaces were generated by injecting CAP reagent for 5 minutes at a flow rate of 2 µl/min. Biotinylated TEM1-Fc (10 µg/ml) was injected onto the streptavidin coated sensor surface for 20 sec (Fc2, RL=~50 RU), 40 sec (Fc3, RL=~100 RU), and 60 sec (Fc4, RL=~150 RU) at a flow rate of 25 µl/minute. Rat anti-TEM-1 MAbs were injected for 300 seconds at 0.5 nM, 2 nM, 5 nM, 20 nM, and 50 nM concentrations and the dissociations were monitored for 30 minutes at a flow rate of 25 µl/minute. The sensor surface was regenerated by injecting a CAP kit regeneration solution for 120 sec at a flow rate of 25 µl/minute. The sensorgrams were analyzed using 1:1 binding model. Results are provided in Table 7.

TABLE 7

BIAcore analysis results for selected TEM-1-specific rat antibodies

| Antibody | ka (1/Ms) | kd (1/s) | KD (M) |
|---|---|---|---|
| 16D2 | 8.10E+05 | 1.07E−08 | 1.31E−14 |
| 7H12 | 1.08E+06 | 3.01E−08 | 2.79E−14 |

TABLE 7-continued

BIAcore analysis results for selected TEM-1-specific rat antibodies

| Antibody | ka (1/Ms) | kd (1/s) | KD (M) |
|---|---|---|---|
| 15F8 | 7.42E+05 | 1.65E−07 | 2.22E−13 |
| 9A5 | 8.50E+05 | 1.84E−05 | 2.16E−11 |
| 11D1 | 4.00E+05 | 9.57E−05 | 2.40E−10 |
| 15D10 | 9.93E+05 | 1.05E−04 | 1.06E−10 |
| 7D3 | 6.59E+04 | 1.34E−07 | 2.03E−12 |

Figure 2:
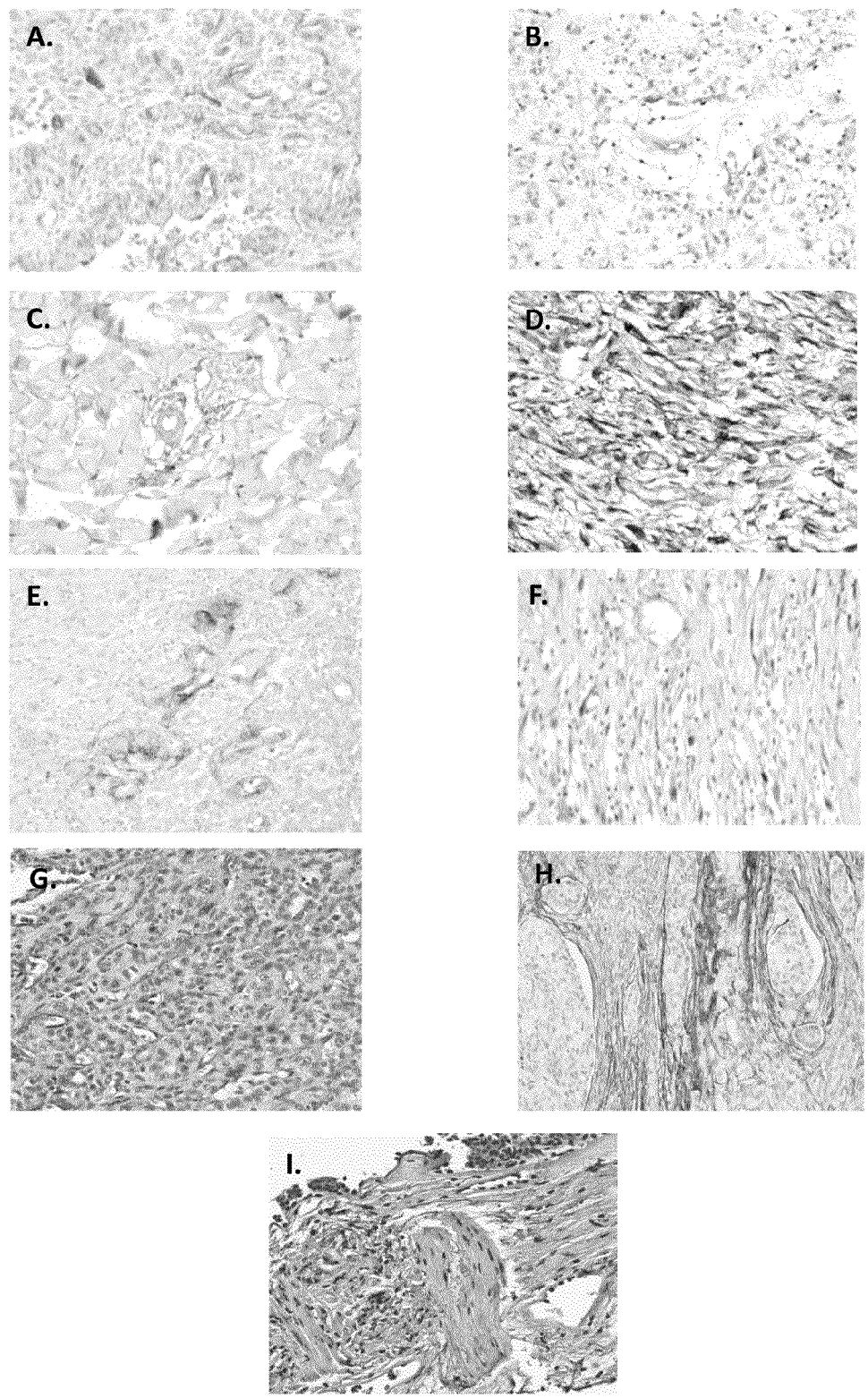
FIG. 2—Images of TEM-1 distribution, as detected by antibody 9G5, on histological samples from subjects having bladder cancer (A), liposarcoma (B), melanoma (C), fibromyxosarcoma (D), melanoma (E), leimyosarcoma (F), hepatocellular cancer (G), gastric cancer (H), or colorectal cancer (I) are shown.

Antibody 9G5, which was not observed to bind reduced and denatured TEM-1 (Western blot) but did bind native TEM-1 (FACS analysis), was also assessed for the ability to detect TEM-1 in histological sample preparations. An indirect immunohistochemical (IHC) testing method was performed for these experiments using Avidin-Biotin Complex (ABC) detection (Vector Labs; catalog #PK-6100). Formalin-fixed paraffin-embedded specimens were sectioned at 5 microns on positively-charged glass slides and heated for approximately 60 minutes at 60° C. Slides were deparaffinized in 3 sequential baths of xylene for 3 minutes each, transferred to three sequential baths of 100% alcohol for 3 minutes each, followed by three sequential baths of 95% alcohol for 3 minutes each and then rinsed for 5 minutes in deionized (DI) water. For the IHC procedure, slides were pretreated in Diva heat-induced epitope retrieval solution (Biocare Medical; catalog #DV 2004 MX) diluted to 1:10 in DI water, placed inside a pressurized decloaking chamber already filled with 500 ml of DI water, and incubated for 30 seconds at 125° C. and 15-20 PSI and then gradually cooled for 15 minutes down to 95° C. Then the slides were cooled at room temperature for 15 minutes before being gently rinsed in DI water until detergent bubbles disappeared. The slides were then washed in 3 sequential baths of Tris Buffered Saline/0.1% Tween-20 wash buffer (TBST) for 3 minutes each (all subsequent buffer washes were performed in this manner). The washed slides were placed into Peroxidase-1 blocking solution (Biocare Medical; catalog #PX 968 MM; reagent is ready to use) for 5 minutes at room temperature and then washed again with TBST. The slides were then incubated for 30 minutes in 5% goat serum and then, without washing, were incubated for 60 minutes at room temperature in a solution containing either 1.25 µg/ml (1:1200) of primary anti-TEM-1 clone 9G5 antibody diluted in Antibody Diluent (Dako; catalog #S0809) or Murine IgG1κ Negative Isotype reagent (Sigma Aldrich; catalog #M9269-1MG). After incubation the slides were washed with TBST and then incubated with biotinylated anti-rat secondary link antibody (Vector Labs; catalog #BA-9400) at 7.5 µg/ml for 30 minutes at room temperature. The slides were again washed with TBST prior to being incubated with the ABC detection reagent (Vector Labs) diluted 1:50 in TBST for 30 minutes at room temperature. After washing with TBST, the slides were incubated in 3,3'-diaminobenzidine tetrahydrochloride (DAB) substrate buffer and chromogen solution (Dako; catalog #K3468) for 5 minutes at room temperature. Following incubation, slides were thoroughly rinse slides in DI water 3 times for 30-60 seconds each prior to counterstaining the slides with hematoxylin (Harris) for 2 minutes. The slides were then dehydrated in 3 sequential baths each of 95% and 100% alcohol for 30 seconds each. The slides were cleared in 3 sequential baths of xylene for 30 seconds each before applying coverslips. Selected images are provided in FIG. 2. Additional sections that stained positive for TEM-1 expression include hepatocellular cancer metastases to the duodenal bulb, hepatocellular cancer metastases to the scalp, hepatocellular cancer metastases to the lung, hepatocellular cancer metastases to the clavicle, hepatocellular cancer metastaises to the pleura, colorectal cancer metastaises to the liver, colorectal cancer metastases to the lung, colorectal cancer metastases to the bladder, colorectal cancer metastases to lymph node, colorectal cancer metastases to the abdomen, gastric cancer metastases to the peritoneum, gastric cancer metasases to the cerebellum, gastric cancer metastases to the omentum, gastric cancer metasases to the liver, gastric cancer metasases to a lymph node, and gastric cancer metasases to the lung (data not shown).

Example 3

Detection of TEM-1 in Normal Human Serum

Figure 3:
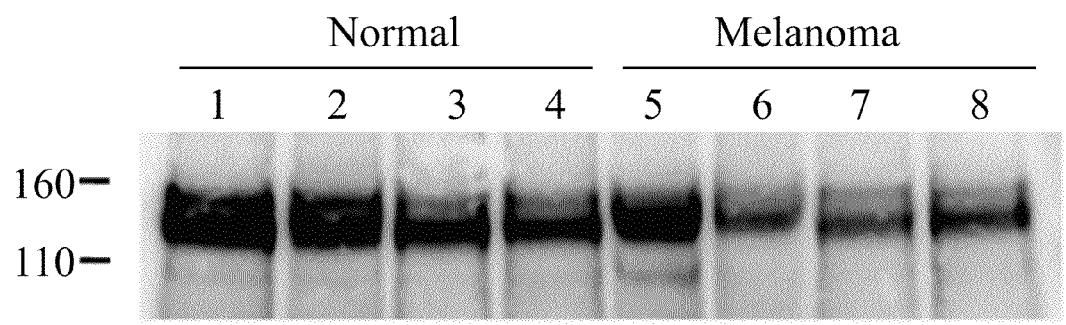
FIG. 3—Depicted is a Western blot of TEM-1 immunoprecipitated from human serum obtained from melanoma patients. The individual samples were not normalized for protein content, thus the intensities of the bands shown in the figure are not reflective of the relative concentration of TEM-1 in the samples.

Blood samples obtained from normal human subjects or melanoma patients were assessed to determine if TEM-1 could be detected in human blood. For this study, serum from normal healthy donors was pre-cleared with protein G sepharose FF beads (Amersham), followed by centrifugation to remove the sepharose beads. TEM-1 was immunoprecipitated by adding MORAb-004 (2 µg) and incubating the cleared serum samples overnight, adding washed protein G sepharose beads to the serum/antibody mixture, and rocking the mixture for an additional two hours. After incubation, the samples were centrifuged and the supernatant was removed. The samples were then washed three times with cold lysis buffer 50 mM Tris-HCl, pH 7.5, 150 mM NaCl, 1.1% OBG supplemented with Complete™ Mini Protease Inhibitor Cocktail (Roche Diagnostics)+PMSF (100 nM)). Protein was eluted using in 4× NuPAGE sample buffer (Invitrogen) containing 5% (β-mercaptoethanol and boiled for 10 minutes. Proteins were separated using SDS-polyacrylamide gel electrophoresis (SDS-PAGE) on a 4-12% Bis-Tris gel (Invitrogen) and transferred to PVDF membrane Immunoblotting was conducted using a rabbit anti-TEM-1 antibody, detected with a goat anti-rabbit-HRP conjugated antibody (Jackson Immunoresearch) and visualized using SuperSignal® West Pico chemiluminescent substrate (Pierce). Signal was visualized using the Omega 12iC molecular imaging system (Ultra-Lum). FIG. 3 illustrates that TEM-1 can be readily detected in samples derived from human blood of both normal subjects and melanoma patients.

Example 4

Electrochemiluminescence Assay for the Detection of TEM-1

An electrochemiluminescence (ECL) assay was developed for the detection of TEM-1 in the presence of TEM-1-specific antibody MORAb-004. The assay makes use of biotin labeled (20:1) anti-TEM-1 antibody 9G5 as the capture antibody and sulfo-TAG labeled (20:1) anti-TEM-1 antibody 15F8 for detection. Samples and controls diluted 1:10 in assay buffer (1% casein in PBS with 0.1% Triton X-100) were quantified using 7 standard calibrators prepared with a 250 ng/mL recombinant CHO TEM-1 Fc fusion protein (Morphotek, Inc.) titrated 5-fold to 16 µg/mL in assay buffer. The assay was carried out by adding 100 µL of complex mix containing 0.5 µg/mL biotin labeled anti-TEM-1 antibody and 0.5 µg/mL sulfo-TAG anti-TEM-1 antibody in 1% casein in PBS to 50 µL of each standard, control, and sample, prepared in the presence or absence of MORAb-004, on a polypropylene microplate, and incubating the mixture at ambient temperature for 1 hour with agitation. During complex formation, a Mesoscale Discovery (Gaithersburg, Md.) standard streptavidin plate was blocked with 150 µL/well of 1% casein in PBS for 1 hour at ambient temperature with shaking. After removal of blocking buffer, 50 µL of complex samples were incubated in duplicate wells on the streptavidin plate for 1 hour at ambient temperature with shaking. The plates were washed three times with 1×PBS with 0.1% Tween 20, and 150 µL/well 1× read buffer T was added and then read with MSD Sector Imager 2400. Table 8 shows the ability of the ECL assay to detect TEM-1 in the presence or absence of MORAb-004.

TABLE 8

Detection of TEM-1 in the presence or absence of MORAb-004.
% Recovery of TEM-1 QCs spiked with MORAb-004

| MORAb-004 spike | Quality Control (ng/mL) | | | | |
|---|---|---|---|---|---|
| (µg/mL) | 50 | 10 | 2 | 0.4 | 0.08 |
| 50 | 93.1 | 87 | 89.9 | 91.9 | 94.1 |
| 25 | 92.8 | 91.3 | 89.1 | 96.5 | 96 |
| 12.5 | 92.1 | 91.2 | 92.8 | 96.5 | 99.4 |
| 6.25 | 95.7 | 94.4 | 94.2 | 98 | 101 |
| 3.125 | 94.5 | 95.8 | 96 | 101 | 103 |
| 1.5625 | 98.9 | 97.7 | 98.9 | 102 | 103 |
| 0.78125 | 99.3 | 100 | 99.9 | 105 | 107 |
| 0 | 104 | 105 | 106 | 109 | 114 |

Figure 4:
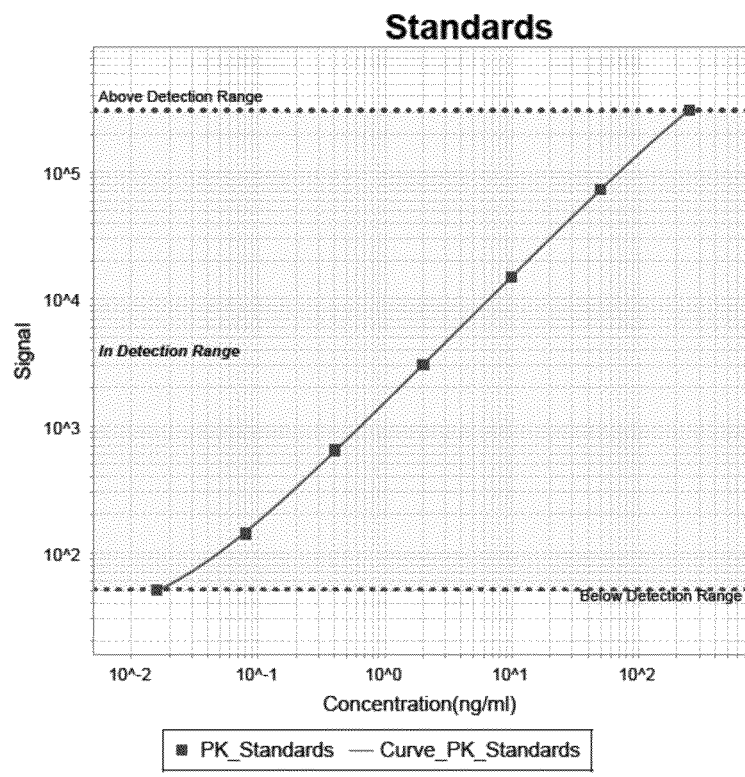
FIG. 4—The detection range for a TEM-1 ECL assay is depicted.

The described ECL assay was then assessed for the ability to detect TEM-1 accurately in human serum or plasma. The assay was carried out as described above; however, instead of assessing the ability of the detecting antibodies to perform adequately in the presence of MORAb-004, 50 ng of TEM-1-Fc was added into either diluted pooled serum or diluted pooled plasma and the degree of recovery was determined (Tables 9 and 10). For each condition tested approximately 90% or more of added TEM-1 was accounted for by the ECL method. The detection range for the assay is provided in FIG. 4.

TABLE 9

ECL-based detection of TEM-1 in pooled serum.
Pooled Serum + 0.1% Triton X

Serum Parallelism

| Dilution | Exp. Conc + Endogenous | Bac Calc. Conc (ng/mL) | Adjusted Conc. | % Diff | Endogenous |
|---|---|---|---|---|---|
| 10 | 5 | 14.3 | 143 | 286.0 | 93 |
| 20 | 2.5 | 7.15 | 143 | 286.0 | 93 |
| 40 | 1.25 | 3.64 | 145.6 | 291.2 | 96 |
| 80 | 0.625 | 1.88 | 150.4 | 300.8 | 100 |
| 160 | 0.3125 | 0.953 | 152.48 | 305.0 | 102 |
| 320 | 0.15625 | 0.508 | 162.56 | 325.1 | 113 |
| 640 | 0.078125 | 0.264 | 168.96 | 337.9 | 119 |
| 1280 | 0.0390625 | 0.133 | 170.24 | 340.5 | 120 |

Serum Parallelism + 50 ng/mL

| Dilution | Original Conc. | Conc. After Spike (ng/mL) | Spike Conc. | % Recov. Of Spike |
|---|---|---|---|---|
| 10 | 14.3 | 59.2 | 45 | 89.8 |
| 20 | 7.15 | 56 | 49 | 97.7 |
| 40 | 3.64 | 54.1 | 50 | 100.9 |
| 80 | 1.88 | 49.8 | 48 | 95.8 |
| 160 | 0.953 | 49.7 | 49 | 97.5 |
| 320 | 0.508 | 48.4 | 48 | 95.8 |
| 640 | 0.264 | 50.2 | 50 | 99.9 |
| 1280 | 0.133 | 50.9 | 51 | 101.5 |

TABLE 10

ECL-based detection of TEM-1 in pooled plasma.
Pooled Plasma + 0.1% Triton X

Plasma Parallelism

| Dilution | Exp. Conc + Endogenous | Bac Calc. Conc (ng/mL) | Adjusted Conc. | % Diff | % Endogenous |
|---|---|---|---|---|---|
| 10 | 5 | 12.5 | 125 | 250.0 | 75 |
| 20 | 2.5 | 6.53 | 130.6 | 261.2 | 81 |
| 40 | 1.25 | 3.19 | 126 | 252.0 | 76 |
| 80 | 0.625 | 1.6 | 128 | 256.0 | 78 |
| 160 | 0.3125 | 0.807 | 129.12 | 258.2 | 79 |
| 320 | 0.15625 | 0.416 | 133.12 | 266.2 | 83 |
| 640 | 0.078125 | 0.204 | 130.56 | 261.1 | 81 |
| 1280 | 0.0390625 | 0.102 | 130.56 | 261.1 | 81 |

Plasma Parallelism + 50 ng/mL

| Dilution | Original Conc. | Conc. After Spike (ng/mL) | Spike Conc. | % Recov. Of Spike |
|---|---|---|---|---|
| 10 | 12.5 | 62.1 | 50 | 99.2 |
| 20 | 6.53 | 57.6 | 51 | 102.1 |
| 40 | 3.15 | 52.7 | 50 | 99.1 |
| 80 | 1.6 | 52.7 | 51 | 102.2 |
| 160 | 0.807 | 50.3 | 49 | 99.0 |
| 320 | 0.416 | 49.9 | 49 | 99.0 |
| 640 | 0.204 | 50.7 | 50 | 101.0 |
| 1280 | 0.102 | 48 | 48 | 95.8 |

Example 5

TEM-1-Based Discrimination Between Normal Subjects and Subjects Having Cancer

Figure 5:
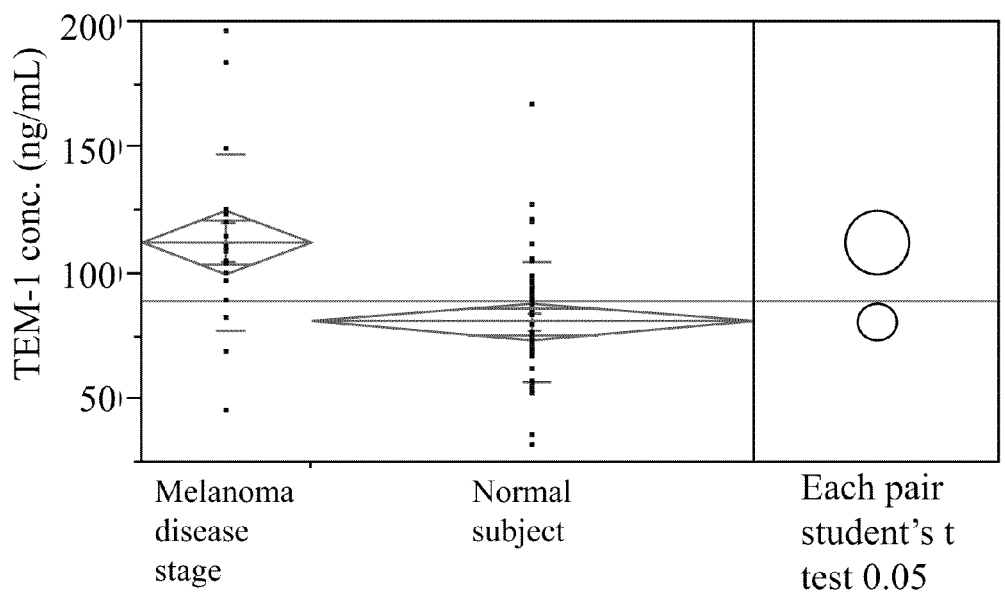
FIG. 5—A graphical representation of TEM-1 concentration in serum of normal subjects or disease-stage melanoma patients is shown. A graphical representation of the statistical variation of the samples is also provided.
Figure 6:
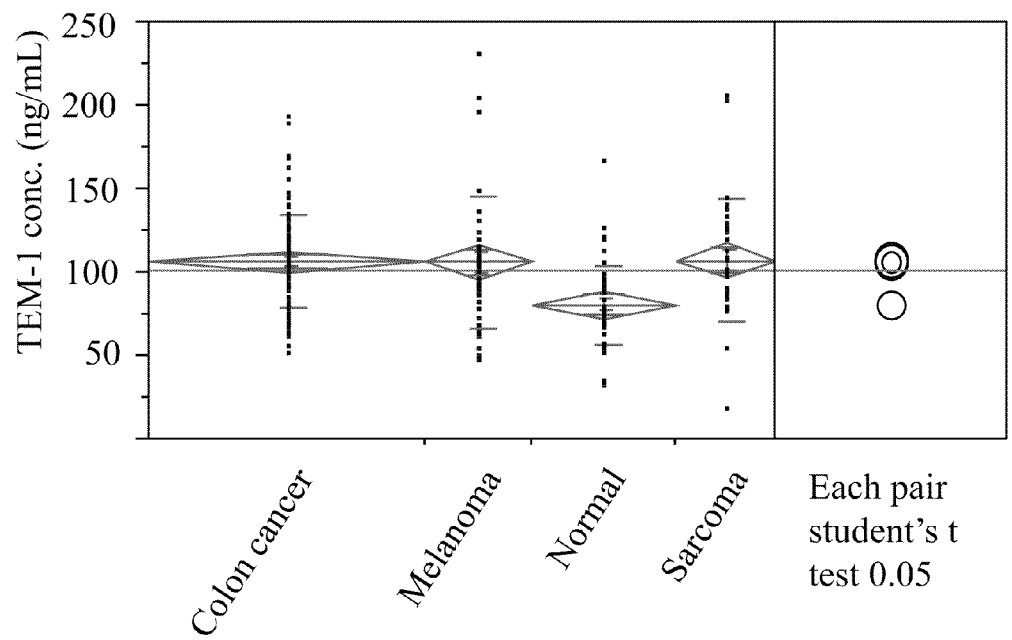
FIG. 6—A graphical representation of TEM-1 concentration in plasma of normal subjects or cancer patients is shown. A graphical representation of the statistical variation of the samples is also provided.

Studies were conducted to assess whether the concentration of TEM-1 in blood is indicative of a subject having cancer. Blood samples were obtained from normal subjects or subjects known to have cancer and the concentration of TEM-1 in plasma or serum was determined, as described in Example 4. As shown in FIG. 5, serum TEM-1 concentrations were elevated in patients having disease-stage melanoma when compared to levels observed for subjects not known to have cancer. In a broader study, the concentrations of TEM-1 in plasma samples from 50 normal individuals, 95 colon cancer patients, 36 melanoma patients, and 34 sarcoma patients were determined to assess whether elevated TEM-1 concentration correlated to disease. A statistical analysis (pair-wise t-test) demonstrates that cancer patient plasma TEM-1 levels are statistically significantly different from plasma levels of TEM-1 in normal individuals (Table 11 and FIG. 6).

TABLE 11

TEM-1 plasma concentrations for normal individuals and cancer patients

| Cancer type | Sample Number | Mean TEM-1 conc. | Standard Deviation |
|---|---|---|---|
| Colon | 95 | 106.566 | 27.5527 |
| Melanoma | 36 | 106.422 | 40.1036 |
| Sarcoma | 34 | 107.526 | 36.2904 |
| Normal | 50 | 80.956 | 23.8352 |

What is claimed:

1. An isolated antibody, or antigen-binding fragment thereof, that specifically binds TEM-1 comprising a light chain CDR1 having the amino acid sequence of SEQ ID NO: 73, a light chain CDR2 having the amino acid sequence of SEQ ID NO: 74, a light chain CDR3 having the amino acid sequence of SEQ ID NO: 75, a heavy chain CDR1 having the amino acid sequence of SEQ ID NO: 77, a heavy chain CDR2 having the amino acid sequence of SEQ ID NO: 78, and a heavy chain CDR3 having the amino acid sequence of SEQ ID NO: 79.

2. The isolated antibody or antigen-binding fragment of claim 1, wherein the antibody is a rat antibody.

3. The isolated antibody or antigen-binding fragment of claim 1 having a light chain variable region comprising the amino acid sequence of SEQ ID NO: 76.

4. The isolated antibody or antigen-binding fragment of claim 1 having a heavy chain variable region comprising the amino acid sequence of SEQ ID NO: 80.

5. An isolated antibody that specifically binds TEM-1, wherein said antibody is the antibody produced by the cell line deposited with the ATCC having accession number PTA-12547.

6. The isolated antibody of claim 1, wherein said antibody is capable of binding to TEM-1 with a dissociation constant of $1\times10^{-8}$M or less.

7. The isolated antibody of claim 1, wherein the antibody is detectably labeled.

8. The antibody of claim 7, wherein the detectable label is a radiolabel, a fluorescent label, an epitope tag, biotin, a chromophore label, an ECL label, or an enzyme.

9. The antibody of claim 8, wherein the label is ruthenium, $^{111}$In-DOTA, $^{111}$In-diethylenetriaminepentaacetic acid (DTPA), horseradish peroxidase, alkaline phosphatase and beta-galactosidase, or poly-histidine.

10. A kit for detecting the presence of TEM-1 in a biological sample, comprising the antibody of claim 1, or an antigen-binding fragment thereof, and a vessel for containing the antibody, when not in use, and instructions for use of the antibody.

11. A kit for detecting the presence of TEM-1 in a biological sample, comprising the antibody of claim 1, or an antigen-binding fragment thereof, and wherein the included antibody, or antigen-binding fragment thereof, is affixed to a solid support.

12. A kit for detecting the presence of TEM-1 in a biological sample, comprising the antibody of claim 1, or an antigen-binding fragment thereof, and wherein the included antibody, or antigen-binding fragment thereof, is detectably labeled.

* * * * *